US010987250B2

(12) United States Patent
Morehouse et al.

(10) Patent No.: US 10,987,250 B2
(45) Date of Patent: *Apr. 27, 2021

(54) SAFETY HANDLE

(71) Applicant: Try This First, Inc., Berkeley, CA (US)

(72) Inventors: Scott Morehouse, Berkeley, CA (US); Bradley Castillo, San Ramon, CA (US); Gordon L Rogers, Walnut Creek, CA (US)

(73) Assignee: Try This First, Inc., Berkeley, CA (US)

( * ) Notice: Subject to any disclaimer, the term of this patent is extended or adjusted under 35 U.S.C. 154(b) by 496 days.

This patent is subject to a terminal disclaimer.

(21) Appl. No.: 15/616,741

(22) Filed: Jun. 7, 2017

(65) Prior Publication Data

US 2017/0266050 A1  Sep. 21, 2017

Related U.S. Application Data

(63) Continuation of application No. PCT/US2015/064821, filed on Dec. 9, 2015.

(60) Provisional application No. 62/089,682, filed on Dec. 9, 2014.

(51) Int. Cl.
*A61F 11/00* (2006.01)
*A23G 3/56* (2006.01)
*A61J 7/00* (2006.01)
*A61M 31/00* (2006.01)

(52) U.S. Cl.
CPC .............. *A61F 11/00* (2013.01); *A23G 3/56* (2013.01); *A23G 3/563* (2013.01); *A61J 7/003* (2013.01); *A61M 31/00* (2013.01); *A61M 2210/0675* (2013.01)

(58) Field of Classification Search
None
See application file for complete search history.

(56) References Cited

U.S. PATENT DOCUMENTS

| | | | |
|---|---|---|---|
| 2,246,778 A | 6/1941 | Cahoon | |
| 3,264,115 A | 8/1966 | Davis | |
| 4,551,329 A | 11/1985 | Harris et al. | |
| 5,223,259 A | 6/1993 | Lackney | |
| 5,773,058 A | 6/1998 | Jones | |
| 5,955,099 A | 9/1999 | White | |
| 5,993,870 A | 11/1999 | Hoeting et al. | |
| 6,375,236 B1 | 4/2002 | Ducharme | |
| 7,147,883 B1 * | 12/2006 | Silver | A23G 1/56 426/548 |
| 8,524,300 B1 | 9/2013 | Diamond et al. | |
| 2003/0163149 A1 | 8/2003 | Heisinger, Jr. | |
| 2004/0156955 A1 | 8/2004 | Klima | |
| 2005/0142252 A1 | 6/2005 | Brown et al. | |
| 2007/0178123 A1 * | 8/2007 | Levenson | A61K 9/0053 424/400 |
| 2008/0223737 A1 | 9/2008 | Atela et al. | |
| 2008/0038414 A1 | 11/2008 | Veciana I. Membrado et al. | |
| 2009/0286448 A1 | 11/2009 | Lopez | |
| 2013/0243889 A1 | 9/2013 | Morehouse | |

FOREIGN PATENT DOCUMENTS

| | | |
|---|---|---|
| RU | 2295247 C1 * | 3/2007 |
| WO | 1995023577 A1 | 9/1995 |

OTHER PUBLICATIONS

International Search Report and Written Opinion dated Feb. 16, 2016 for PCT Application No. PCT/US2015/064821.

* cited by examiner

*Primary Examiner* — Terry A McKelvey
*Assistant Examiner* — Catheryne Chen
(74) *Attorney, Agent, or Firm* — Patterson + Sheridan LLP

(57) ABSTRACT

The present invention relates generally to devices and methods for treating ear infections and clearing excess fluid from Eustachian tubes.

18 Claims, 15 Drawing Sheets

SAFETY HANDLE

CROSS-REFERENCE TO RELATED APPLICATIONS

This application is a continuation under 35 U.S.C. § 120 of International Application No. PCT/US2015/064821, filed Dec. 9, 2015, which claims the benefit of U.S. Provisional Patent Application No. 62/089,682, filed on Dec. 9, 2014. Each of the above-referenced patent applications is incorporated by reference in its entirety.

BACKGROUND OF THE INVENTION

Provided is a lollipop handle with safety features to retain the candy on the handle while the candy is being consumed.

There are four primary types of ear infections: acute otitis media (AOM); otitis media with effusion (OME); chronic otitis media (COM); and acute otitis externa (AOE). AOM is a middle ear infection caused by bacteria that traveled to middle ear from fluid build-up in the Eustachian tube. AOM may develop during or after a cold or the flu. Middle ear infections are very common in children, but occur infrequently in adults. In children, ear infections often recur, particularly if they first develop in early infancy. OME occurs when fluid (also referred to as an "effusion") becomes trapped behind the eardrum in one or both ears, even when there is no infection. In chronic and severe cases, the fluid may become sticky and may cause a condition commonly known as "glue ear." While OME or even glue ear is typically not painful, it frequently causes an uncomfortable feeling of stuffiness in the ears that is akin to a feeling of being under water. Children who are susceptible to OME can experience frequent episodes for up to half of their first three years of life. While most episodes of OME resolve within three months, 30-40% of children experience recurrent episodes. Chronic and severe OME may impair a child's hearing. COM refers to persistent fluid behind the tympanic membrane without the presence of an infection. It is called suppurative chronic otitis when there is persistent inflammation in the middle ear or mastoids or if there is a chronic rupture of the eardrum with drainage. AOE is an inflammation or infection of the outer ear and ear canal that is triggered by water that gets trapped in the ear. The trapped water can cause bacteria and fungi to breed. AOE can also be precipitated by overly aggressively scratching or cleaning of the ears or when an object gets stuck in the ears.

The standard of care for the treatment of ear infections is either to wait until the infection clears or to treat the infection with antibiotics. Typically, pain associated with the ear infection is treated with ibuprofen or acetaminophen. For patients that experience chronic ear infections, the repeated use of antibiotics poses risks that the bacterium or bacteria that are causing the infection will become resistant to the antibiotics. Once a patient becomes resistant to a particular antibiotic, the patient must require higher doses of the antibiotic and/or switch to a different antibiotic to treat the infection.

SUMMARY

In one aspect, provided is a handle, e.g., for a lollipop, the handle comprising: a longitudinally extending handle portion comprising a main body of sufficient length to be held by a full human hand; and a curved mouthpiece portion comprising a concave surface, wherein the mouthpiece is of a size and shape to comfortably fit in a human oral cavity and immovably hold a candy while under negative pressure in the oral cavity, and wherein the handle portion is fixably attached to the flat portion.

In varying embodiments, the mouthpiece portion comprises a spoon curvature, one or more apertures or holes sufficient to allow candy syrup to pass through, and the concave surface comprises one or more grooves of a width and length sufficient to be filled with candy syrup. In varying embodiments, the one or more grooves have a curved or arc shape. In varying embodiments, the mouthpiece comprises a single aperture sufficient to allow candy syrup to pass through, and the concave surface comprises two pairs of concentric grooves arcing around or tracing the curvature of the aperture, wherein the arc angles of the concentric grooves is from about 20° to about 80°, e.g., from about 25° to about 75°, e.g., from about 30° to about 70°. In varying embodiments, the one or more apertures are beveled or tapered up to about 15°, e.g., about 10-12°, such that the opening of the aperture on the concave surface is narrower than the opening of the aperture on the convex surface. In varying embodiments, the handle is angled up to about 45°, e.g., in the range of about 5° to about 45°, e.g., in the range of about 10° to about 40°, e.g., in the range of about 15° to about 35°, e.g., about 10°, 12°, 15°, 18°, 20°, towards the concave or bottom side relative to the mouthpiece. In varying embodiments, the mouthpiece portion is oval or round. In some embodiments, the proportions of the handle portion are sufficient to be held by a full human child hand. For example, in some embodiments, the handle portion comprises a length of about 4.25 inches and an average width in the range of about 0.35 to about 1.5 inches, e.g., about 0.75 to about 1.5 inches. In some embodiments, the proportions of the handle portion are sufficient to be held by a full human adult hand. In varying embodiments, the handle comprises a bulbous end. In some embodiments, the handle is comprised of a material that does not melt at a temperature of at least about 300° F., e.g., at least about 310° F., 320° F., 325° F., 330° F., 340° F., 350° F., or higher. In varying embodiments, the handle is made of one or more polymers. In some embodiments, the polymer is selected from the group consisting of TORLON™, PEEK™, TEFLON™, RULON™, polypropylene, polyethylene, low density polyethylene, filled polypropylene, silicone, polysulfone, polyethersulfone, polyphenylsulfone, and mixtures thereof. In varying embodiments, the handle portion further comprises circumferentially or cross-sectionally aligned non-slip ribs or grooves. In varying embodiments, the handle is as depicted in FIGS. 1-15.

In a further aspect, provided are methods of orally delivering an active agent to an individual in need thereof. In some embodiments, the methods comprise providing a lollipop (e.g., a safety handle as described herein with the mouthpiece coated with candy) to the individual, wherein the individual sucks on the candy-coated mouthpiece of the handle, thereby dissolving the candy and orally delivering the active agent to the individual.

In a further aspect, provided are methods of treating an ear infection or releasing pressure in the inner ear of an individual in need thereof. In some embodiments, the methods comprise providing a lollipop (e.g., a safety handle as described herein with the mouthpiece coated with candy) to the individual, wherein the individual sucks on the candy-coated mouthpiece of the handle, thereby forming a negative pressure in the oral cavity that pulls fluid out of the Eustachian tubes, thereby releasing pressure in the inner ear and treating the ear infection. In varying embodiments, the individual sucks on the candy-coated mouthpiece of the handle while lying down with the infected or painful ear facing upwards.

In a further aspect, provided are kits comprising one or more lollipops (e.g., a safety handle as described herein with the mouthpiece coated with candy), as described herein.

BRIEF DESCRIPTION OF THE DRAWINGS

FIG. 1 illustrates top and bottom views of the safety handle, e.g., for a lollipop. The convex side of the mouthpiece (spoon-shaped portion) comprises one or more apertures or holes which can be any shape and are of a size sufficient to allow candy syrup to pass through. The concave side of the mouthpiece comprises one or more apertures or holes which can be any shape and are of a size sufficient to allow candy syrup to pass through and one or more curved grooves of a sufficient width, depth and length to allow candy syrup fill them in.

DETAILED DESCRIPTION OF CERTAIN INVENTIVE EMBODIMENTS

Definitions

Figure 1:
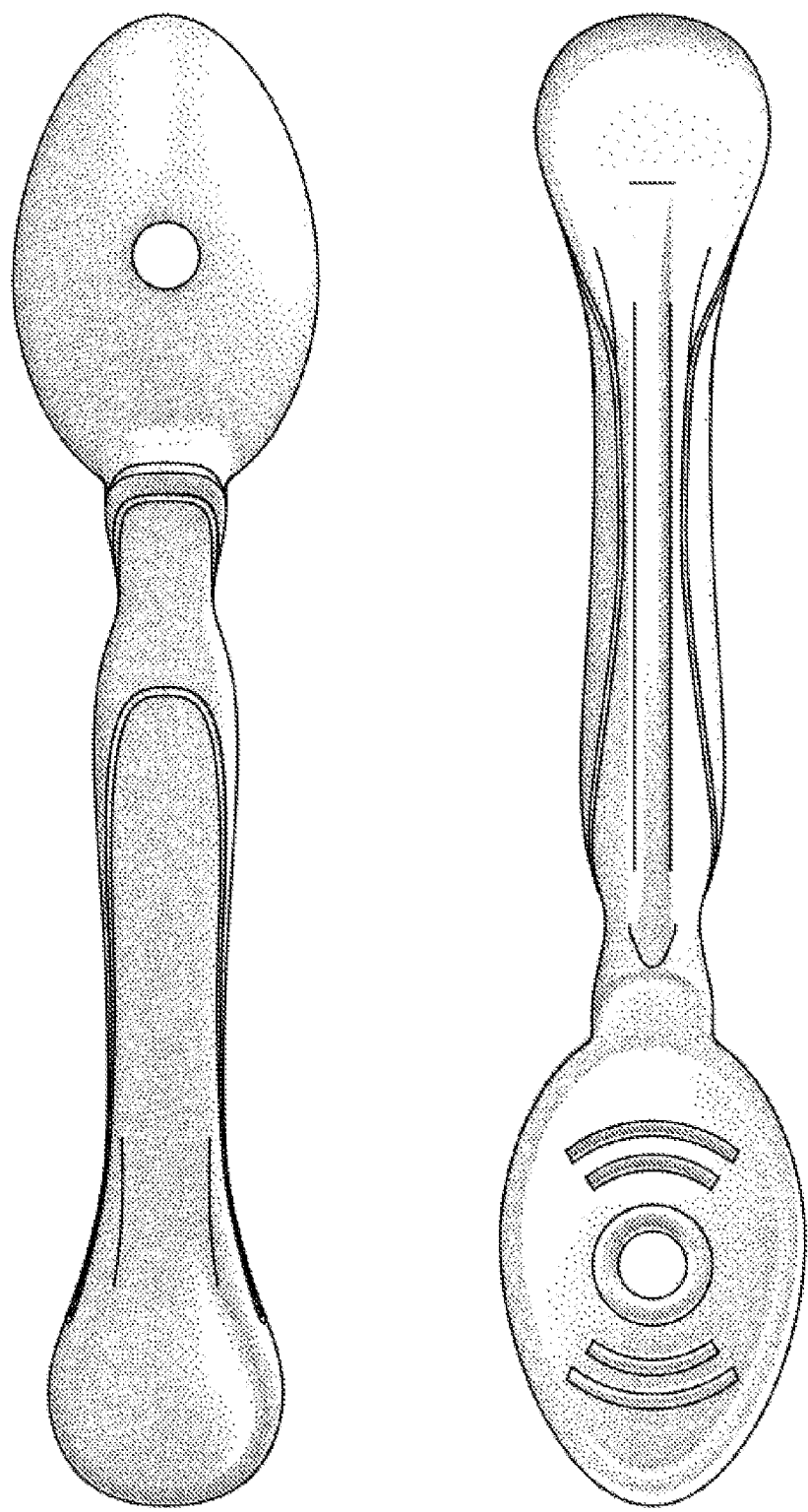
Figure 2:
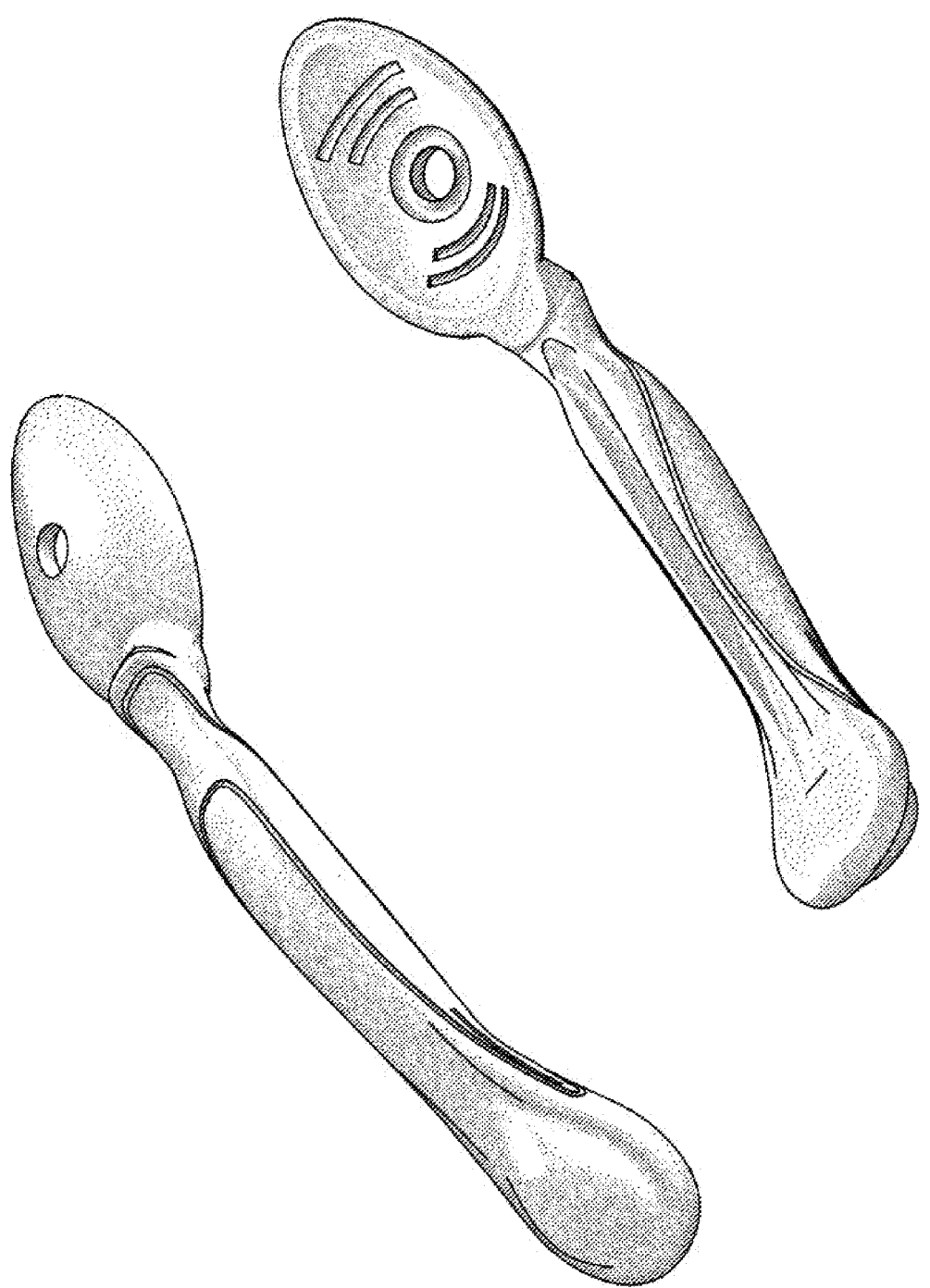
FIG. 2 illustrates angled perspective top and bottom views of the safety handle.
Figure 3:
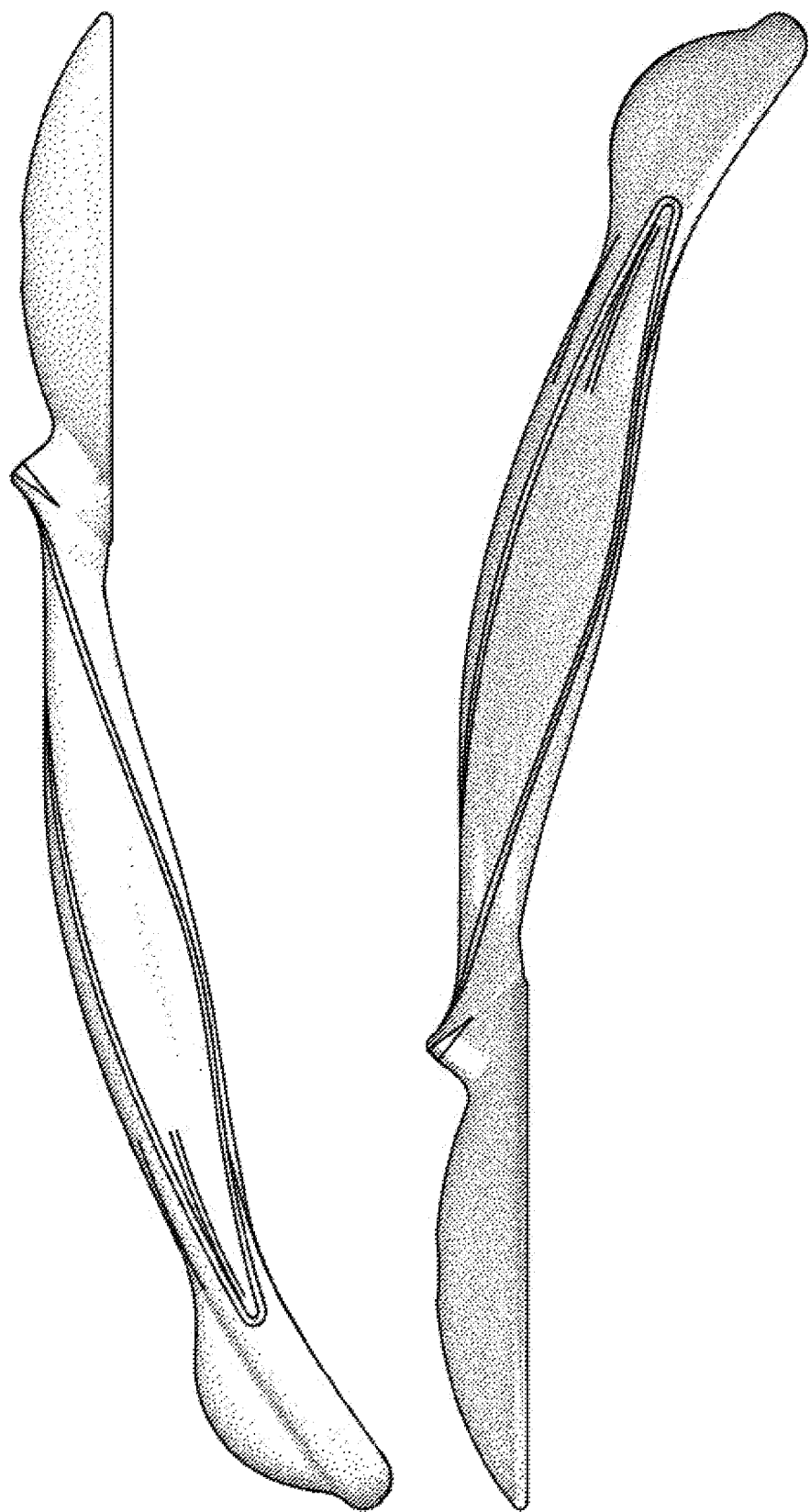
FIG. 3 illustrates side views of the safety handle.
Figure 4:
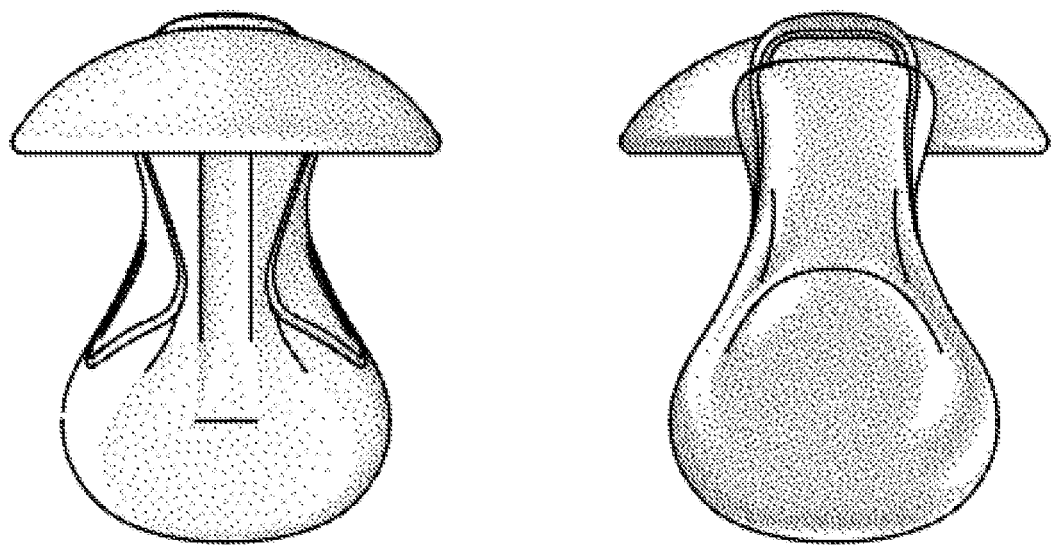
FIG. 4 illustrates front and back views of the safety handle.
Figure 5:
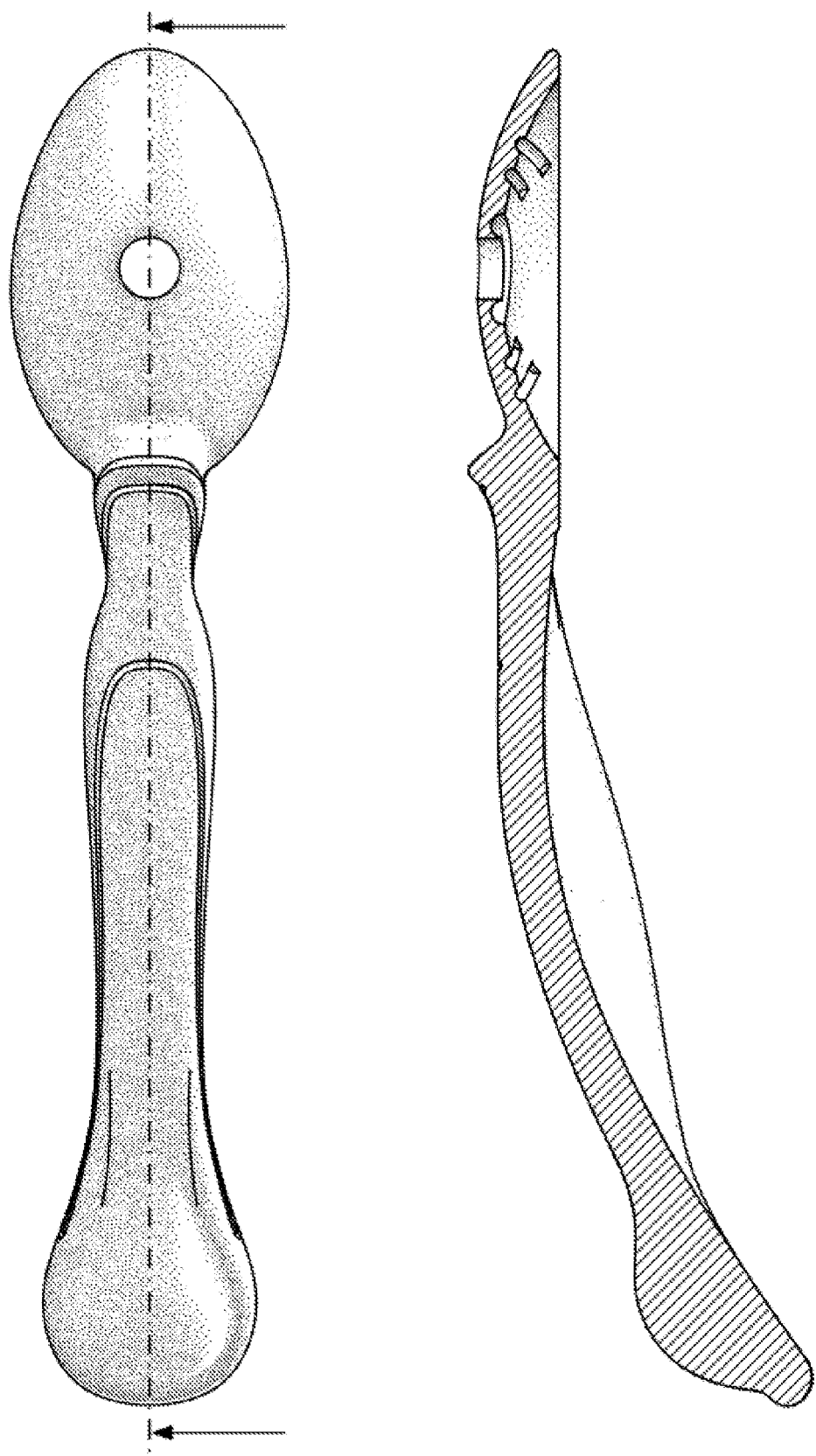
FIG. 5 illustrates a side section view of the safety handle. The inner cylindrical surface of the aperture can be beveled or tapered up to 15° (e.g., replaced with a conical surface with a cone angle of up to 15 degrees off-axis) so that the aperture in the concave side is narrower than the aperture on the convex side.
Figure 6:
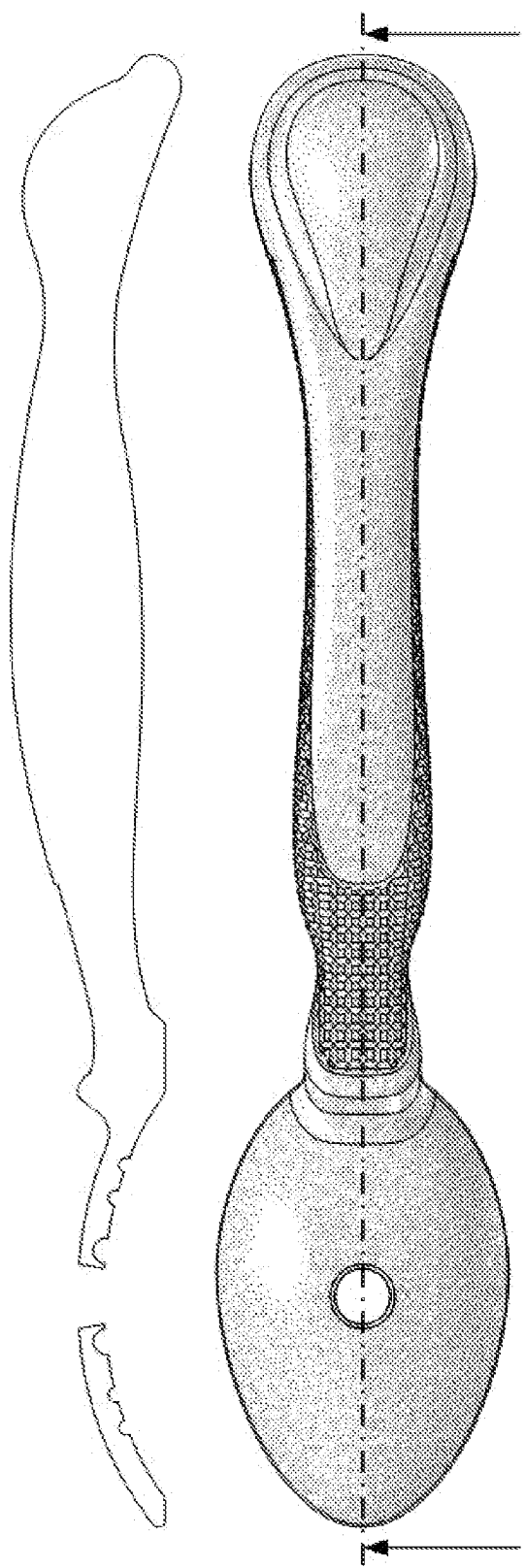
FIG. 6 illustrates a side section view of the safety handle, depicting the inner cylindrical surface of the aperture angled at 10° so that the aperture in the concave side is narrower than the aperture on the convex side. The texturing on the handle is optional.
Figure 7:
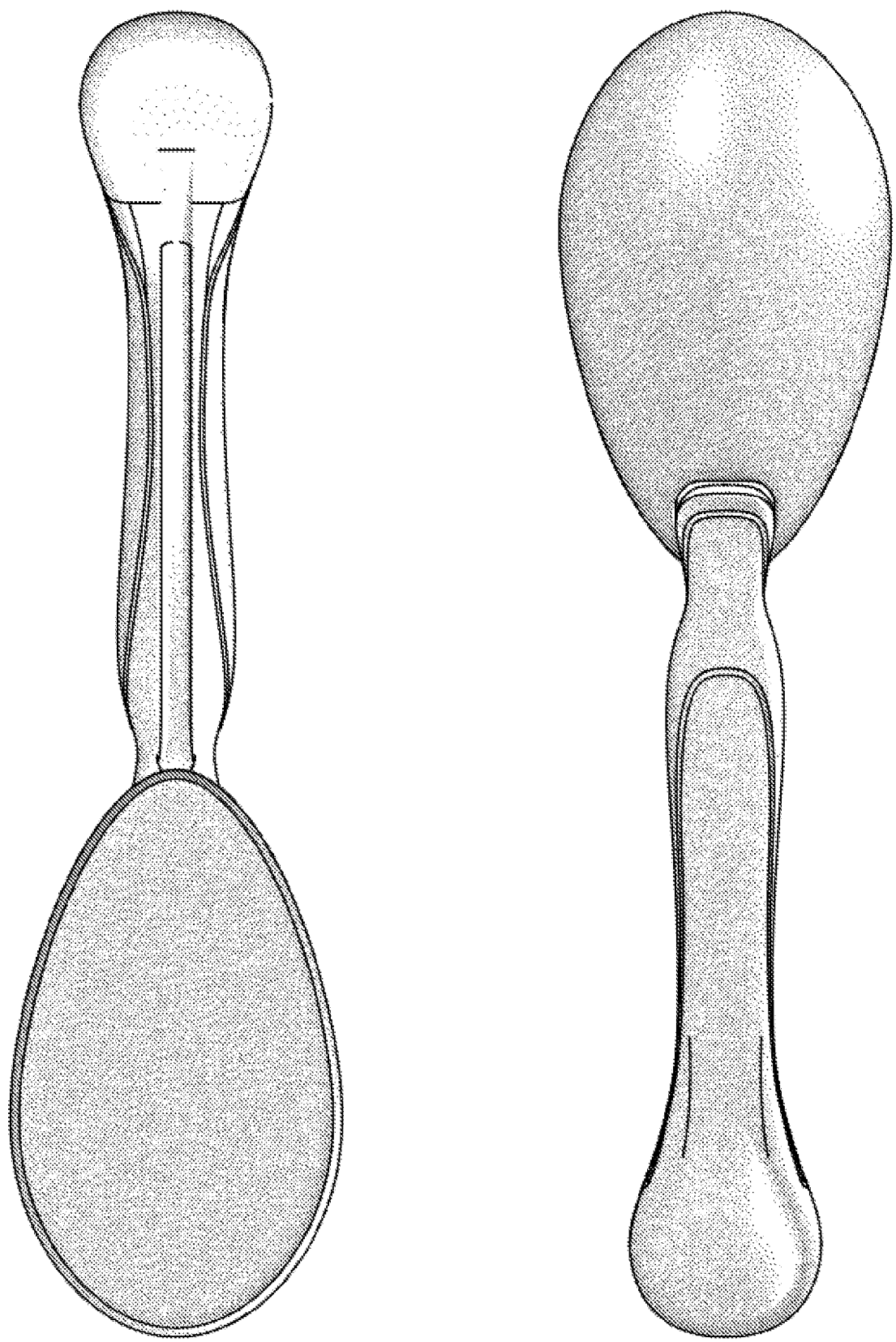
FIG. 7 illustrates a top and bottom views of the safety handle coated with or encapsulated in hard candy.
Figure 8:
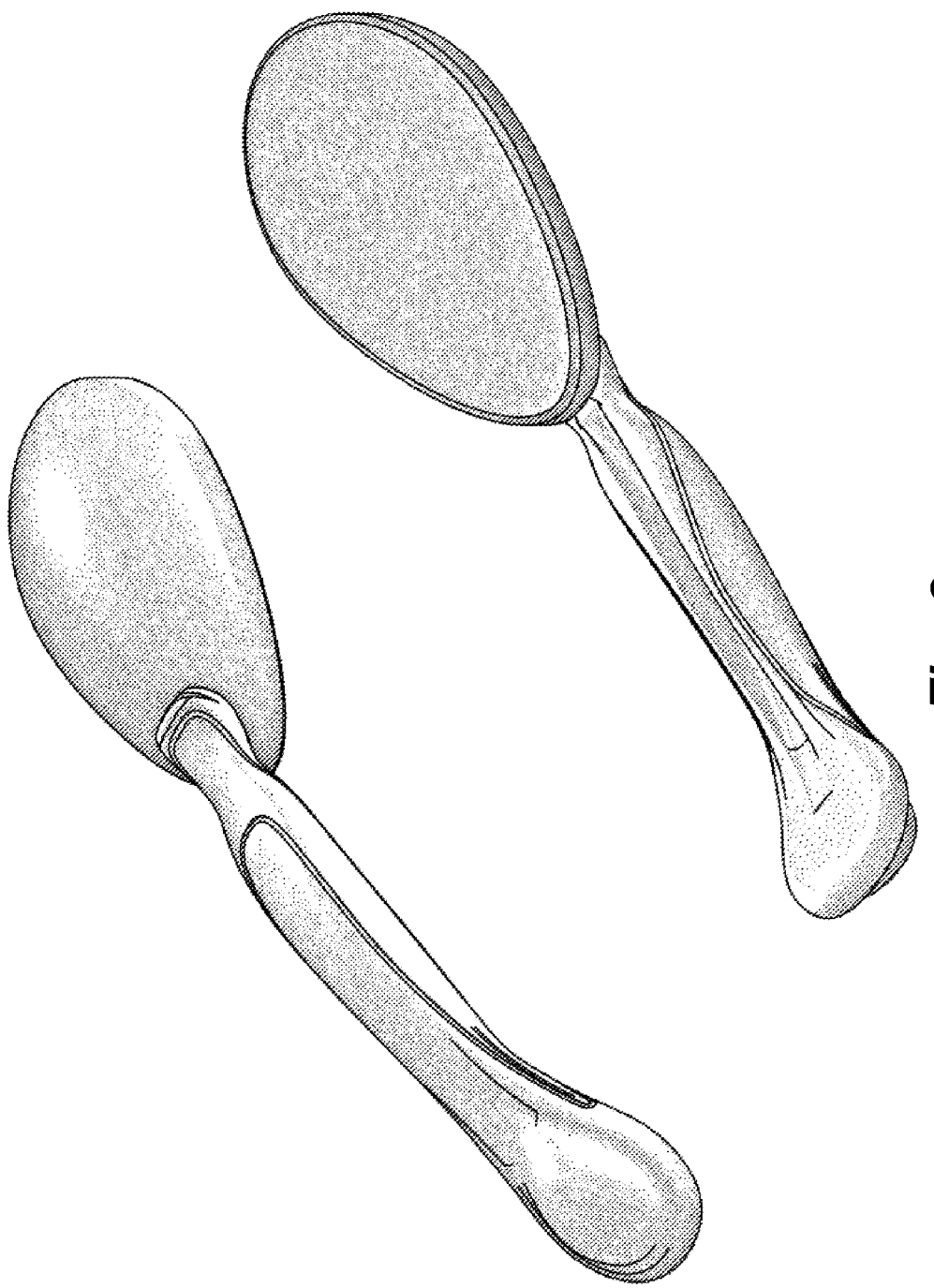
FIG. 8 illustrates angled perspective top and bottom views of the safety handle with the mouthpiece (spoon-shaped portion) coated with or encapsulated in hard candy.
Figure 9:
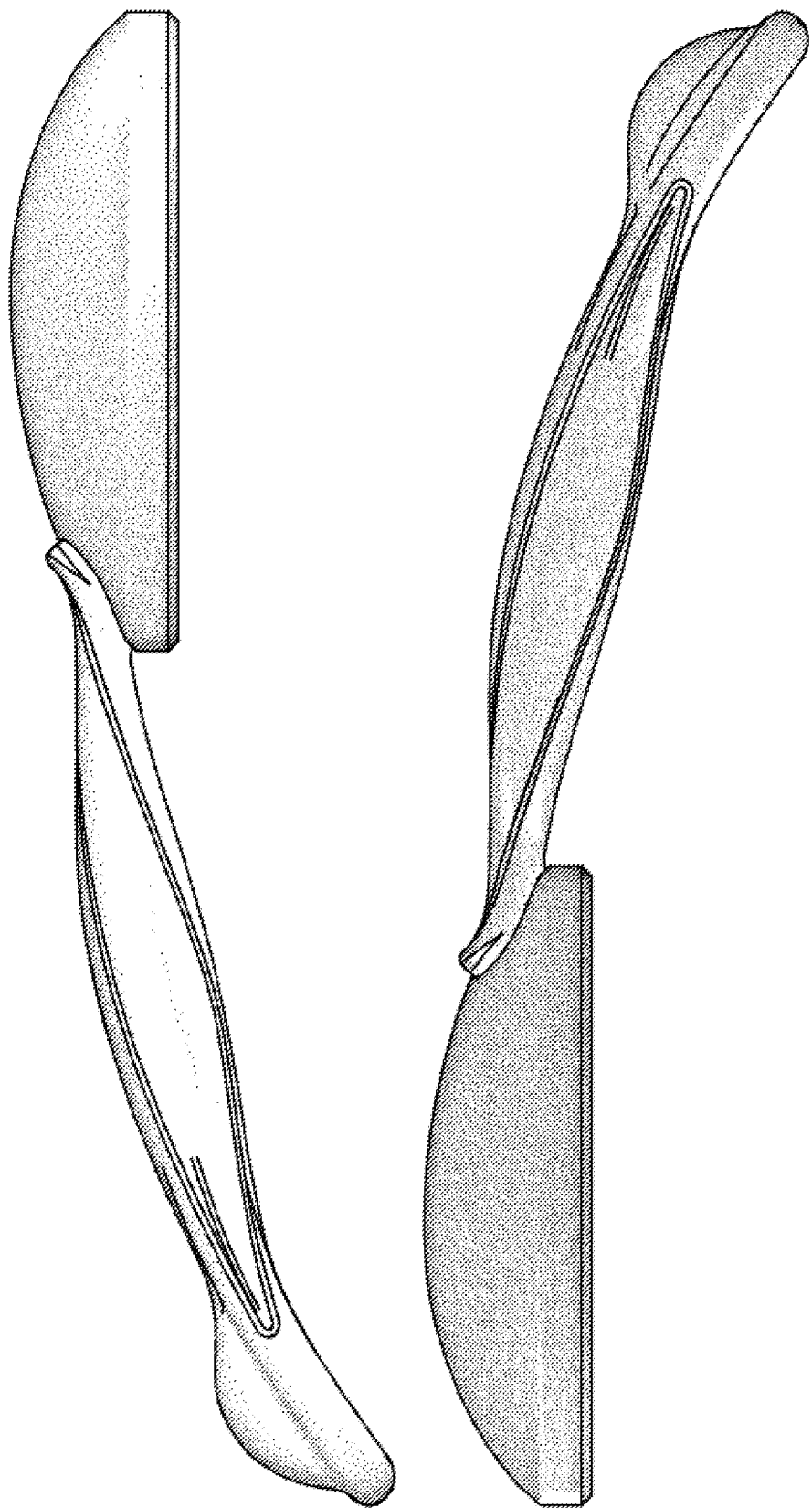
FIG. 9 illustrates side views of the safety handle with the mouthpiece coated with or encapsulated in hard candy.
Figure 10:
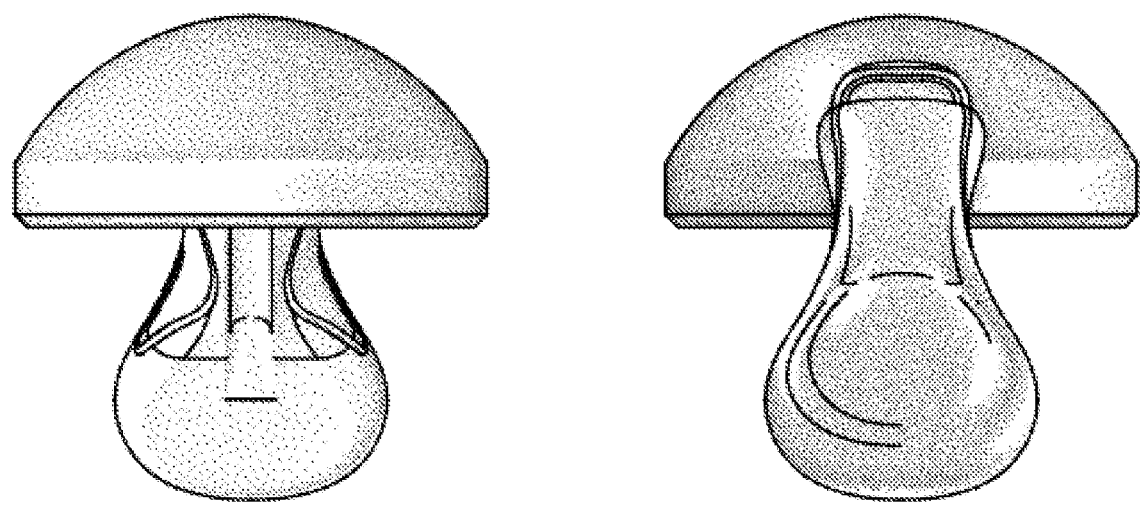
FIG. 10 illustrates front and back views of the safety handle with the mouthpiece coated with or encapsulated in hard candy.
Figure 11:
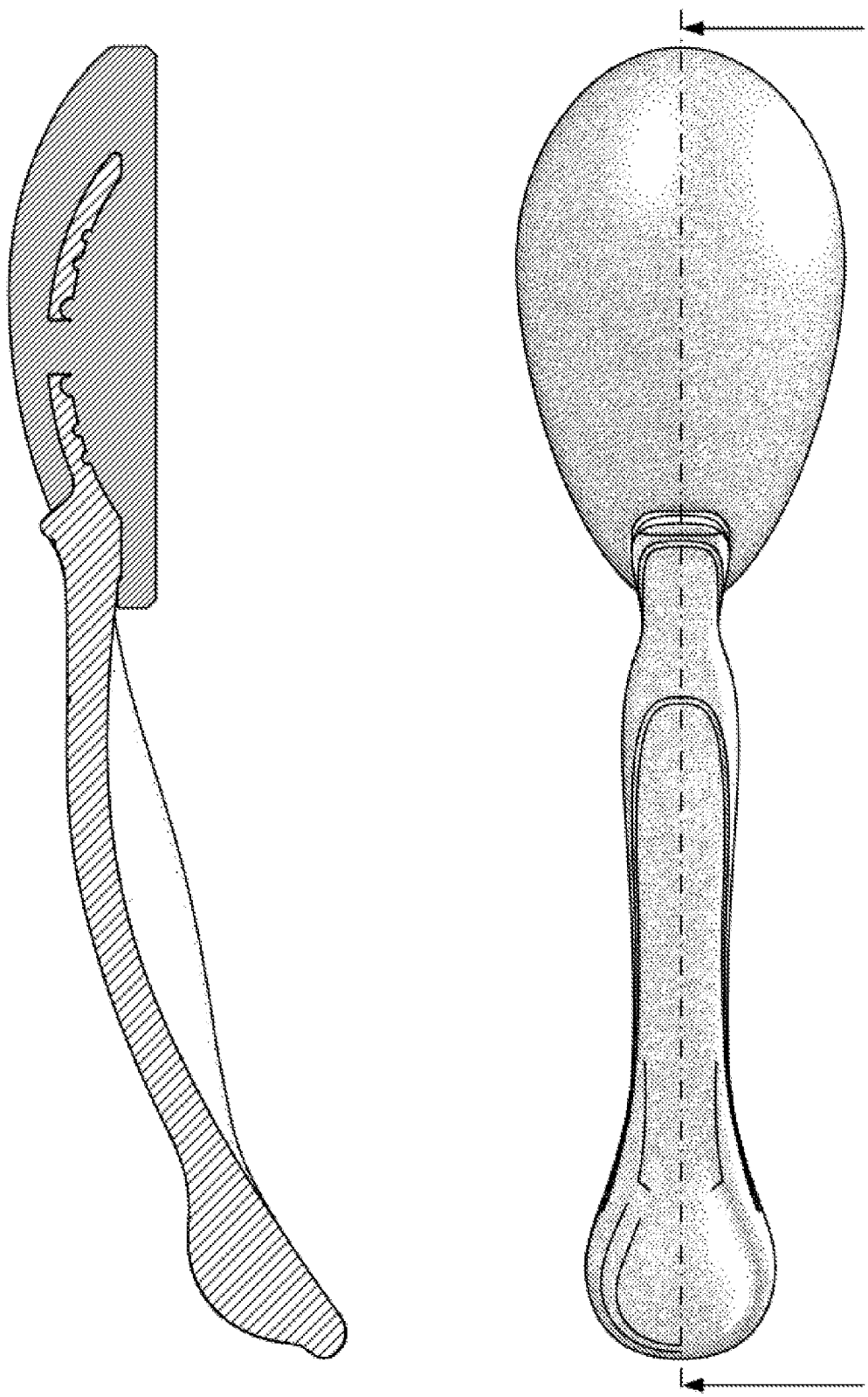
FIG. 11 illustrates side section views of the safety handle with the mouthpiece coated with or encapsulated in hard candy.
Figure 12:
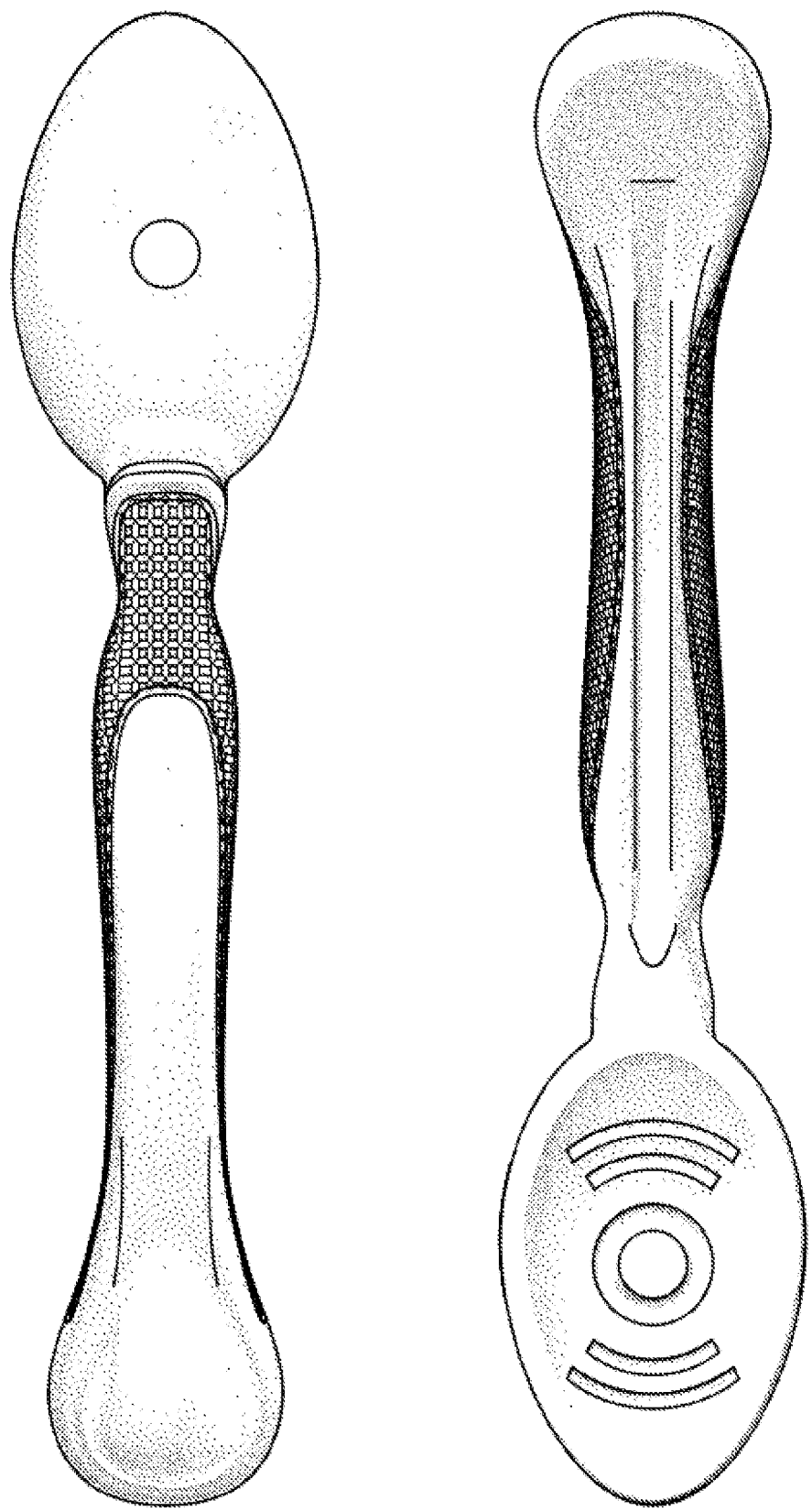
FIG. 12 illustrates top and bottom views of the safety handle depicting optional texturing.
Figure 13:
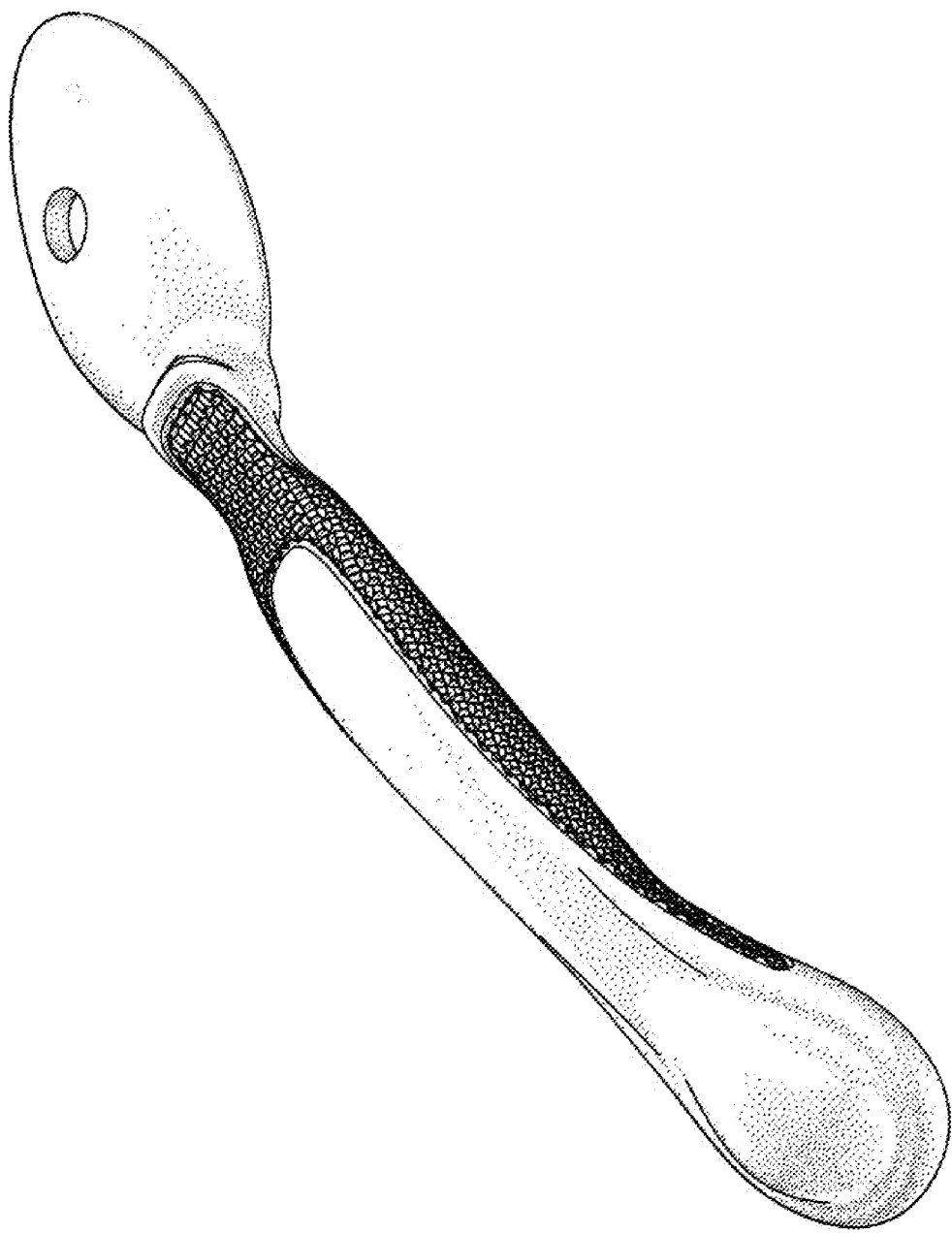
FIG. 13 illustrates an angled perspective top view of the safety handle depicting optional texturing.
Figure 14:
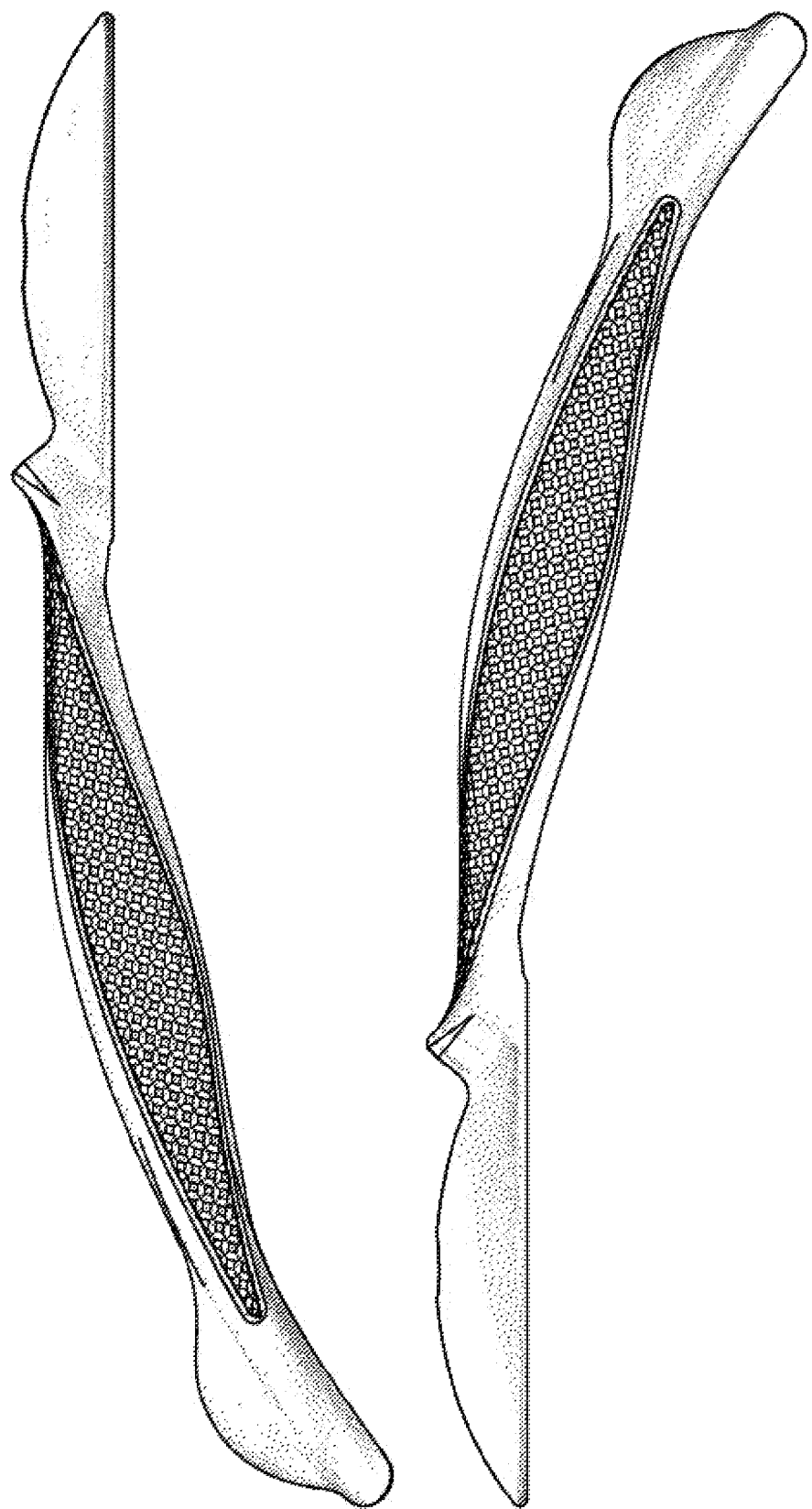
FIG. 14 illustrates side views of the safety handle depicting optional texturing.
Figure 15:
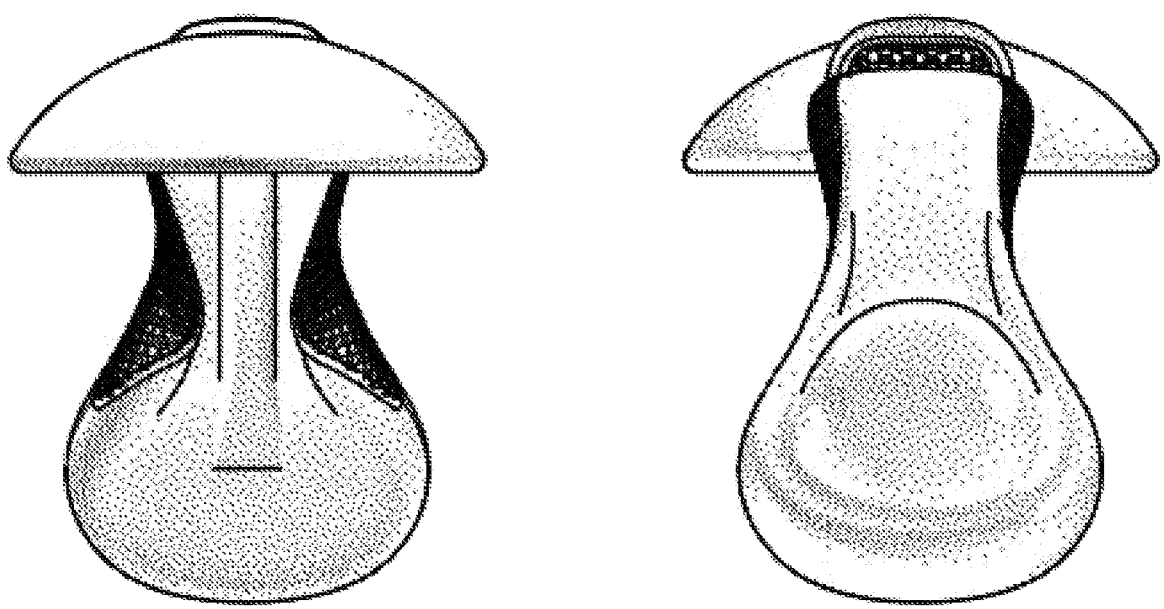
FIG. 15 illustrates front and back views of the safety handle depicting optional texturing.

As used in this specification and the appended claims, the singular forms "a," "an," and "the" include plural referents unless the context clearly dictates otherwise. The terms "comprises" and/or "comprising," as used in this specification and the appended claims, specify the presence of stated features, steps, components and/or groups, but do not preclude the presence or addition of one or more other features, steps, components, and/or groups.

As used herein, the term "individual," "subject" or "patient" refers to a human. The individual will often be a child under the age of 10 years of age; however, the individual may also be an early adolescent (10 to 13 years of age), an adolescent (14-18 years of age), or an adult (over 18 years of age).

The term "treatment" or "alleviating" as used herein refers to reduction in severity and/or frequency of symptoms associated with ear infections, including pain.

The terms "active agent" and "drug" are used interchangeably to refer to a chemical material or compound which, when administered to a patient induces a desired pharmacologic effect. Included are derivatives that include pharmacologically acceptable and pharmacologically active salts, esters and amides, as well as prodrugs and conjugates. Analogs of those compounds or classes of compounds specifically mentioned that also induce the desired pharmacologic effect, are also included.

The term "effective amount" or "pharmaceutically effective amount" refer to the amount and/or dosage, and/or dosage regime of one or more compounds necessary to bring about the desired result e.g., an amount sufficient to mitigating in a subject the pain and/or discomfort associated with excess fluid in the inner ear canal, or clogged or blocked Eustachian tubes (ET).

The term "lollipop" refers to a piece of hard candy attached to a stick or "handle."

The term "shape of a human oral cavity" refers to a solid composition or solid confection that is substantially flat on a first side (e.g., for contacting the tongue) and rounded on the remainder of the composition, e.g., as in a half-spherical or half-oval shape (e.g., for contacting the roof of the mouth). A composition of the form or shape of a human oral cavity is of a size to comfortably fit within a human oral cavity of a subject.

The term "substantially flat" in the context of a surface of a solid composition or solid confection refers to a substantially smooth, level surface with little or no slope, tilt, or curvature. In some embodiments, a substantially flat surface may be slightly concave or convex. In some embodiments, the substantially flat surface is textured, e.g., with ridges or bumps.

The term "pacifier shape" refers to any conventional or commercially available shape of a mouthpiece of a pacifier. In various embodiments, pacifier shape refers to standard nipple shape or the orthodontic pacifier shape. In some embodiments, pacifier shape refers to the shape of a NUK® pacifier.

The term "polyhedron" refers to a three-dimensional a solid bounded by usually 4 or more plane faces (i.e., flat faces) and straight edges. In various embodiments, the polyhedron is a regular polyhedron.

The term "octahedron" refers to a three-dimensional shape having eight plane faces, for example, a regular solid figure with eight equal triangular faces.

The term "octagon" or "octagonal" refers to a disk shape having two substantially flat surfaces, eight straight sides and eight side angles.

The term "consisting essentially of" refers to the genera or species of active pharmaceutical agents recited in a method or composition, and further can include other agents that, on their own do not effect substantial activity for the recited indication or purpose. In some embodiments, the phrase "consisting essentially of" expressly excludes the inclusion of one or more additional active agents not specifically recited.

Introduction

Provided is a safety handle for a lollipop with several features that can be used alone or in combination to immovably hold or retain hardened candy mounted on the mouthpiece while the candy is dissolved, e.g., under negative pressure in the oral cavity of a human Safety features on the handle portion include a bulbous end, non-slip texturing (e.g., ribs or grooves), and non-slip or soft polymer insets or overlays on harder polymer. Safety features on the mouthpiece portion include one or more apertures or holes (which can be tapered or beveled) that candy syrup can flow through, grooves or channels engraved in the concave surface of the mouthpiece that candy syrup can flow into. The handles find use in the construction of or as a mounting base of hardened candy for a lollipop, e.g., that can be used for therapeutic purposes.

Safety Handle

The present safety handle has a mouthpiece portion and a handle portion. In varying embodiments, the ratios or proportions of the length to height to width of the safety handle are 8.58 (l):1.0 (h):1.7 (w). In varying embodiments, the handle has a length in the range of about 3.35 inches to about 6.0 inches; an average width in the range of about 0.35 inches to about 1.5 inches width and an average height or thickness of about 0.15 inches to about 0.50 inches. In varying embodiments, the full length, height and width of the safety handle are 4.29 (l), 0.5 (h) and 0.85 (w), respectively. As appropriate or desired, the proportion and size of the handle can be adjusted for the end user.

In varying embodiments, the handle portion is positioned with respect to or attached to the mouthpiece at an angle of up to about 50° off of horizontal, bent towards the concave or bottom side, e.g., as depicted in FIGS. 3, 5, 8, 9, 11 and 14. In varying embodiments, the angle of the handle portion relative to the mouthpiece portion is in the range of about 5° to about 45°, e.g., in the range of about 10° to about 40°, e.g., in the range of about 15° to about 35°, e.g., about 10°, 12°, 15°, 18°, 20°.

In some embodiments, the handle is comprised of a material that does not melt at a temperature of at least about 300° F., e.g., at least about 310° F., 320° F., 325° F., 330° F., 340° F., 350° F., or higher. In varying embodiments, the handle is made of one or more polymers. In some embodiments, the polymer is selected from the group consisting of TORLON™, PEEK™, TEFLON™, RULON™, polypropylene, polyethylene, low density polyethylene, filled polypropylene, silicone, polysulfone, polyethersulfone, polyphenylsulfone, and mixtures thereof.

Handle Portion

Generally, the handle portion is of a size and proportion sufficient to be held by a whole human hand, e.g., having a length of at least the width of four fingers. In embodiments where the handle portion has a bulbous end, the handle portion can be of a length such that the bulbous end is exposed beyond the width of a gripping hand. In varying embodiments, the proportion and size of the handle portion can be adjusted for the end user, e.g., a toddler, a young child, a juvenile, a teenager, an adult. In varying embodiments, the proportion and size of the handle portion are designed to be held by the whole hand of a human child under 10 years of age, e.g., of an age of about 1 to 10 years, e.g., with the bulbous end is exposed beyond the width of the gripping hand. The exposed bulbous end, allows for the safety handle to be grabbed from the child, e.g., by an adult, a caregiver, a parent, etc., if necessary or desired.

In varying embodiments, the handle portion comprises textural features to aid in gripping the handle portion without or with reduced slippage. For example, in varying embodiments, the handle portion can have parallel ribs and/or grooves oriented circumferentially, cross-sectionally or diagonally across the handle portion. In varying embodiments, the textural features to aid in gripping the handle portion without or with reduced slippage can be made from a relatively softer polymer (e.g., a thermoplastic elastomers (TPE) or a thermoplastic rubber). The softer polymer can be inset into or overlaid onto the relatively harder polymer of the handle portion.

Mouthpiece Portion

Generally, the mouthpiece portion is curved, having a convex and concave surface, and is of a size and shape to comfortably fit in a human oral cavity. In varying embodiments, the mouthpiece portion has the shape of a spoon, e.g., has a spoon or spoon-like curvature. In varying embodiments, the mouthpiece has a thickness in the range of about 0.05 to about 0.2 inches, e.g., from about 0.075 to about 0.175 inches.

In some embodiments, the mouthpiece portion has one or more apertures or holes sufficient to allow candy syrup to pass through. The one or more apertures or holes, can be any shape (e.g., circle, oval, square, rectangle, triangle, or polygon) and multiple apertures need not be the same shape. Candy hardened through the one or more apertures and on both sides of the curved mouthpiece is immovably anchored on the mouthpiece while the candy is dissolved or consumed under negative pressure conditions in the oral cavity. In varying embodiments, the sides or edges of the one or more apertures or holes are tapered or beveled such that the opening on the concave surface is narrower than the opening on the concave surface. In varying embodiments, the taper or bevel of the sides or edges of the one or more apertures or holes is in the range of about 5° to about 20°, e.g., about 10° to about 15°, e.g., about 5°, 6°, 7°, 8°, 9°, 10°, 11°, 12°, 13°, 14°, 15°, 16°, 17°, 18°, 19° or 20° off perpendicular.

In varying embodiments, the concave surface comprises one or more grooves or open channels of a width and length sufficient to be filled with candy syrup. Candy hardened into the one or more grooves further anchors the candy onto the surface of the mouthpiece, rendering the candy immobilized and stably anchored on the mouthpiece while the candy is dissolved or consumed under negative pressure conditions in the oral cavity. In varying embodiments, the grooves have a depth of at least about 0.015 inches (e.g., at least about 0.016, 0.017, 0.018, 0.019 or 0.020 inches), e.g., in the range of about 0.015 inches to about 0.025 inches or about 0.030 inches; and a width of at least about 0.035 inches (e.g., at least about 0.036, 0.037, 0.038, 0.039 or 0.040 inches), e.g., in the range of about 0.035 inches to about 0.050 inches, e.g., in the range of about 0.037 to about 0.047 inches. The grooves can have any length greater than the width. In some embodiments, the grooves have a length (e.g., as measured down the center of the groove or channel) of about 0.3 inches to about 0.6 inches. In varying embodiments, the one or more grooves have a curved or arc shape. In varying embodiments, the arc angles of the arc-shaped grooves can be from about 20° to about 80°, e.g., from about 25° to about 75°, e.g., from about 30° to about 70°. In varying embodiments, the grooves are arranges as parallel S-curves or in a parallel sine wave formation. As appropriate or desired, the grooves can radiate out from or encircle or trace the perimeter of an aperture. In varying embodiments, two or more parallel or concentric grooves are engraved into the concave surface of the mouthpiece, forming ribs.

In one embodiment, the mouthpiece comprises a single aperture sufficient to allow candy syrup to pass through, and the concave surface comprises two pairs of concentric grooves arcing around or tracing the curvature of a circular aperture, wherein the arc angles of the arc-shaped concentric grooves is from about 20° to about 80°, e.g., from about 25° to about 75°, e.g., from about 30° to about 70° (e.g., as depicted in FIG. 1).

Lollipop Having Safety Handle

In varying embodiments, the mouthpiece of the safety handle is coated with a hardened candy to form a lollipop. Prior to hardening the candy syrup fills in the grooves in the concave surface of the mouthpiece and flows through the apertures or holes in the mouthpiece so that the candy is immobilized on the mouthpiece, even while dissolving under the negative pressure forces placed on the candy-coated mouth piece in a human oral cavity.

Methods of preparing lollipops are known in the art. Typically lollipops are prepared by mixing one or more sweeteners with water in a non-stick or enameled saucepan, e.g., with a spout, and heating the mixture with stirring until boiling. Examples of sweeteners that may be used to prepare lollipops are set forth in Table 1 and the accompanying text. Where the sweetener is prone to crystallization (such as with table sugar, i.e., sucrose), one or more interfering agents are necessary in order to ensure that the sweetener does not crystallize during the heating process. For example, where table sugar is used to prepare the lollipops, the interfering agents corn syrup and cream of tartar are suitable interfering agents. The long glucose chains in the corn syrup prevent the sucrose from crystallizing and the cream of tartar prevents the crystallization of sucrose by converting the sucrose to fructose and glucose. In order to prevent the recrystallization of the sugar, the mixture should not be stirred after it has started to boil and the sides of the pan should be free of any sucrose crystals that could reseed the sucrose crystallization process. Once the mixture has boiled, the mixture should continue to heat, without stirring, until it has reached a temperature of 300-310° F.; this temperature range is known as the hard crack stage where there is almost no water left in the mixture and the sugar concentration of the mixture is approximately 99%. Once the syrup has reached the hard crack stage, the heat should be turned off and the mixture should be allowed to cool to 275° F. at which time the lollipop flavorings and colorings should be added to the mixture; adding the flavorings and colorings prior to this stage may result in the flavorings and colorings burning off during the cooking process. Once the mixture has cooled to 275° F., the mixture is poured into the lollipop molds, allowed to cool for 10 minutes, and wrapped in appropriate wrapping, such as cellophane or waxed paper. To preserve freshness, the finished lollipops should be stored in a cool, dry place. Any additional ingredients and/or active agents should be added to the lollipop along with the flavorings and colorings when the mixture is at 275° F.

Sweeteners that may be used in the candy may be selected from a wide range of materials including water-soluble natural sweeteners, water-soluble artificial sweeteners, water-soluble sweeteners derived from naturally occurring water-soluble sweeteners, and mixtures thereof. Without being limited to particular sweeteners, representative categories and examples of sweeteners are shown in Table 1.

TABLE 1

| Water-soluble Natural Sweeteners (monosaccharides, disaccharides, and polysaccharides) | Water-soluble Artificial Sweeteners | Water-soluble Sweeteners Derived from Natural Substances |
|---|---|---|
| Dextrose (D-glucose); fructose (levulose); galactose; maltose; mannose; sucrose (table sugar); ribulose; xylose; inverted sugar (a mixture of fructose and glucose derived from sucrose); glycyrrhizin (a natural sweetener derived from licorice root); steviosides (a natural sweetener derived from the leaves of the stevia plant); and naturally-occurring sweet proteins derived from plants, such as monellin, thaumatin, pentadin, mabinlin, and brazzein. | Soluble saccharine salts (e.g., sodium or calcium saccharine salts); aspartame; sodium cyclamate, and acesulfame potassium. | Sugar alcohols (polyols), such as erythritol, lacititol, maltitol, mannitol, sorbitol and xylitol; isomalt (a sugar alcohol derived from glucose and mannitol); hydrogenated starch hydrosylates (a mixture of sugar alcohols derived from corn starch, potato starch, or wheat starch) dihydrochalcones (an artificial sweetener derived from *citrus*); chlorinated derivatives of sucrose (sucralose); and corn syrup. |

Additional natural sweeteners that may be used in the preparation of the present lollipops include, without limitation honey, maple syrup, evaporated cane juice, and one or more concentrated fruit juices. Honey gets its sweetness from a combination of the monosaccharides fructose and glucose and has the same relative sweetness level as the disaccharide sucrose (table sugar). Maple syrup consists primarily of sucrose and water, with small amounts of the fructose and glucose; the presence of malic acid makes maple syrup slightly acidic. Evaporated cane juice and concentrated fruit juices may include combinations of sugars, including fructose, glucose and sucrose.

In varying embodiments, the lollipops are prepared using one or more natural sweeteners, one or more sugar alcohols as set forth in Table 1, or a combination of one or more natural sweeteners and one or more sugar alcohols. Illustrative water-soluble sugar-based sweeteners from Table 1 that may be used for the preparation of the candy for coating the mouthpiece include, e.g., dextrose, fructose, sucrose, mannitol, sorbitol, xylitol, and mixtures thereof. In some embodiments, the sweetening agent is selected from the group consisting of aspartame, cyclamate, saccharin, stevia, sucralose, xylitol, glucose, isomalt, arabitol, erythritol, glycerol, hydrogenated Starch Hydrosylate (HSH), lactitol, maltitol, and mixtures thereof.

As noted in Table 1, water-soluble sweeteners derived from natural substances include sugar alcohols, also referred to as "polyols." Polyols contribute between approximately 0.2 and 3.0 calories per gram as opposed to sucrose, which contributes approximately 4.0 calories per gram, and contribute not only to sweetness but also to bulk; accordingly, the use of polyols can be used in some formulations of the candy for coating the mouthpiece of the handle. Further, it is to be understood that compositions that are to be administered to diabetic patients should be prepared with non-natural sugars, such sucralose, isomalt, or the sugar alcohols and artificial sweeteners set forth in Table 1. In some embodiments, the sweetening agent is a sugar alcohol, e.g., selected from the group consisting of xylitol, mannitol, sorbitol, isomalt, arabitol, erythritol, glycerol, hydrogenated Starch Hydrosylate (HSH), lactitol, maltitol, and mixtures thereof.

The natural sweeteners may be present in the candy a range of about 2% weight for weight (w/w) to about 95% w/w, e.g., with a range of about 50% w/w to about 95% w/w. Because sweeteners derived from natural sources and artificial sweeteners tend to be much sweeter than natural sugars, such non-natural sugars may be present in a range of about 0.01% w/w to about 2% w/w, e.g., with a range of about 0.05% w/w to about 1% w/w.

Any flavoring agent or combinations of flavoring agents may be used in the candy coating the mouthpiece. Examples of flavoring agents that may be used candy are natural flavors and artificial flavors, and mixtures thereof. One example of flavoring agents that may be used to prepare the candy is OTTENS® flavorings (Philadelphia, Pa., USA). Natural flavoring agents include extracts and juices obtained from natural sources. Examples of sources to obtain the natural flavors for use in the candy include, without limitation, acai berries, aloe vera, apples, bananas, blueberries, cantaloupe, caramel, carrots, cherries, chocolate, coconut, coffee, cranberries, grapefruits, grapes, guava, honeydew melons, kiwi, lemons, licorice, limes, lychee fruits, mango, nectarines, olallieberries, oranges, peaches, pears, pineapples, pomegranates, raspberries, strawberries, tangerines, vanilla, watermelon, wheat grass, peppermint oil and spearmint oil.

The natural or artificial flavorings may be present in the candy, e.g., in the range of about 0.005% w/w to about 5% w/w, e.g., with a range of about 0.05% w/w to about 3% w/w.

It is to be understood that citric acid may be a suitable natural alternative to lemon and lime fruit flavorings. The chelating properties of citric acid have the additional benefit of acting as a natural antimicrobial preservative (discussed below). Further, citric acid may also be used to adjust the pH of the candy.

In one embodiment, the candy includes a homeopathic agent. Examples of homeopathic agents that may be included in the candy coating the safety handle mouthpiece include, without limitation, *Acontum Napellus, Allium Ceia, Arnica, Mullein, Belladona, Bellis Perennis, Calendula, Calcarea Carbonica, Chamomilla, Ferum Phosphorilum, Hamamelis, Hepar Sulphuris, Hypericum Perforatum* (Saint John's Wort), *Kau Bichromicum, Kau Iodatum, Kau Muriaticum, Kau Sulphuricum, Lycopodium, Mercurius Solubilis, Mezereum, Millefolium, Natrum Sulphuricum, Phytolacca Decandra, Phosphorus, Pulsatilla, Sulphur*, and *Symphytum Officinale*. The amount of homeopathic agents to be incorporated into the candy coating the safety handle mouthpiece will range from 1 c to 30 c depending on the particular homeopathic agent, with each "c" value representing a 1/100 dilution (e.g., 1 c is 0.01 of the original tincture, 2 c is 0.0001 of the original tincture, etc.).

In another embodiment, the candy can include a vitamin and/or dietary supplement. Examples of vitamins and/or dietary supplements that may be included in the candy include, without limitation, vitamin A (retinyl palmitate, retinol, and/or retinoic acid), vitamin B1 (thiamine), vitamin B2 (riboflavin), vitamin B3 (niacin and/or niacinamide), vitamin B5 (pantothenic acid), vitamin B6 (pyridoxine, pyridoxal, pyridoxamine, and/or pyridoxine hydrochloride), vitamin B7 (biotin), vitamin B8 (inositol), vitamin B9 (folic acid), vitamin B12 (cobalamins), a B complex vitamin, vitamin C, vitamin D (ergocalciferol—vitamin D2 and/or cholecalciferol—vitamin D3), vitamin E (tocopherols and/or tocotrienols), calcium, magnesium, manganese, potassium, selenium, and sodium biocarbonate. The amount of vitamins and/or dietary supplements to be incorporated into the candy coating the safety handle mouthpiece is the standard recommended daily intake (RDI) set by the Food and Drug Administration (FDA).

In a further embodiment, the candy may include an herb, oil, or flower extract. Examples of such extracts include, without limitation, bee propolis extract, chinese vitex, *echinacea*, elder, forsythia, garlic, ginger, goldenseal root extract, horehound, hyssop, isatis, lemon balm, lemon oil, linden flowers, lonicera, mallow, menthol, mineral oil, peppermint oil, spearmint oil, sage, schizonepeta, slippery elm bark extract, and wild thyme.

In another embodiment, the candy may include an essential or non-essential amino acid. As is known to those of skill in the art, the essential amino acids are isoleucine, leucine, lysine, methionine, phenylalanine, threonine, and tryptophan. The non-essential amino acids are alanine, arginine, asparagines, aspartic acid, cysteine, glutamic acid, glycine, histidine, ornithine, proline, selenocysteine, serine, taurine, and tyrosine.

Where appropriate, the candy may contain natural antimicrobial preservatives, such as for example, citric acid and its mineral salts and/or sorbic acid and its mineral salts. Mineral salts of citric acid that may be used as preservatives include sodium citrate (monosodium citrate, disodium citrate, and trisodium citrate) and calcium citrate. Mineral salts of sorbic acid that may be used as preservatives include sodium sorbate, potassium sorbate, and calcium sorbate. The optimal pH for the antimicrobial activity of the citric acid and sorbic acid mineral salts is typically below pH 6.5 and the mineral salts are generally used at concentrations of 0.025% to 0.10% w/w. Because adding mineral salts to food may raise the pH of the food slightly, the pH of the candy may need to be adjusted subsequent to the addition of the mineral salts in order to ensure that the mineral salts are capable of maintaining their antimicrobial activity. In various embodiments, the composition further comprises an antibiotic.

The candy can also optionally include pharmaceutically acceptable buffering agents sufficient to adjust and maintain the pH of the candy in the range of about 3.0 to about 6.5, e.g., about 5.0 to about 6.5. Suitable buffering agents include, without limitation, citrate, phosphate, borate, or acetate salts, which can be derived from substances, such as citric acid, primary or secondary sodium phosphate, boric acid, sodium tetraborate, acetic acid, and sodium acetate, respectively. Other suitable buffering agents are tromethamine and glycine. Where appropriate, the pH of the candy may be adjusted with the addition of a suitable acid such as citric acid, phosphoric acid, succinic acid, or tartaric acid in a quantity suitable to achieve a pH in the range of 4.0 to 8.0. Hydrochloric acid or sodium hydroxide can also be used for pH adjustment.

In some embodiments, the candy comprises 1, 2, 3, 4, 5, or more, active ingredients selected from the group consisting of vitamin A, vitamin B1, vitamin B2, vitamin B3, vitamin B5, vitamin B6, vitamin B7, vitamin B8, vitamin B9, vitamin B12, a B complex vitamin, vitamin C, vitamin E, zinc, magnesium, selenium, *echinacea*, olive leaf (*Olea europaea*), wild indigo (*baptisia tinctoria*), goldenseal (*hydrastis canadensis*), Fenugreek, mullein (*verbascum, olympicum,* and *thapsus*), phenol, camphor, pectin, *eucalyptus* oil, peppermint oil, spearmint oil, and mixtures thereof.

For example, in some embodiments, the composition includes (e.g., comprises, consists of, or consists essentially of) two or more ingredients selected from the combinations listed in Table 2.

TABLE 2

Two Ingredient Combinations

| First Ingredient | Second Ingredient |
| --- | --- |
| Vitamin A | Vitamin B1 |
| Vitamin A | Vitamin B2 |
| Vitamin A | Vitamin B3 |
| Vitamin A | Vitamin B5 |
| Vitamin A | Vitamin B6 |
| Vitamin A | Vitamin B7 |
| Vitamin A | Vitamin B8 |
| Vitamin A | Vitamin B9 |
| Vitamin A | Vitamin B12 |
| Vitamin A | Vitamin C |
| Vitamin A | Vitamin E |
| Vitamin A | Zinc |
| Vitamin A | Magnesium |
| Vitamin A | Selenium |
| Vitamin A | *Echinacea* |
| Vitamin A | Olive leaf (*olea europaea*) |
| Vitamin A | Wild indigo (*baptisia tinctoria*) |
| Vitamin A | Goldenseal (*hydrastis canadensis*) |
| Vitamin A | Fenugreek (*trigonella foenum-graecum*) |
| Vitamin A | Mullein (*verbascum olympicum* & *thapsus*) |
| Vitamin A | Phenol |
| Vitamin A | Camphor |
| Vitamin A | Pectin |
| Vitamin A | *Eucalyptus* Oil |
| Vitamin A | Peppermint Oil |
| Vitamin A | Spearmint Oil |
| Vitamin B1 | Vitamin B2 |
| Vitamin B1 | Vitamin B3 |
| Vitamin B1 | Vitamin B5 |
| Vitamin B1 | Vitamin B6 |
| Vitamin B1 | Vitamin B7 |
| Vitamin B1 | Vitamin B8 |
| Vitamin B1 | Vitamin B9 |
| Vitamin B1 | Vitamin B12 |
| Vitamin B1 | Vitamin C |
| Vitamin B1 | Vitamin E |
| Vitamin B1 | Zinc |
| Vitamin B1 | Magnesium |
| Vitamin B1 | Selenium |
| Vitamin B1 | *Echinacea* |
| Vitamin B1 | Olive leaf (*olea europaea*) |
| Vitamin B1 | Wild indigo (*baptisia tinctoria*) |
| Vitamin B1 | Goldenseal (*hydrastis canadensis*) |
| Vitamin B1 | Fenugreek |
| Vitamin B1 | Mullein |
| Vitamin B1 | Phenol |
| Vitamin B1 | Camphor |
| Vitamin B1 | Pectin |
| Vitamin B1 | *Eucalyptus* Oil |
| Vitamin B1 | Peppermint Oil |
| Vitamin B1 | Spearmint Oil |
| Vitamin B2 | Vitamin B3 |
| Vitamin B2 | Vitamin B5 |
| Vitamin B2 | Vitamin B6 |
| Vitamin B2 | Vitamin B7 |
| Vitamin B2 | Vitamin B8 |
| Vitamin B2 | Vitamin B9 |
| Vitamin B2 | Vitamin B12 |
| Vitamin B2 | Vitamin C |
| Vitamin B2 | Vitamin E |
| Vitamin B2 | Zinc |
| Vitamin B2 | Magnesium |
| Vitamin B2 | Selenium |
| Vitamin B2 | *Echinacea* |
| Vitamin B2 | Olive leaf (*olea europaea*) |
| Vitamin B2 | Wild indigo (*baptisia tinctoria*) |
| Vitamin B2 | Goldenseal (*hydrastis canadensis*) |
| Vitamin B2 | Fenugreek |
| Vitamin B2 | Mullein |
| Vitamin B2 | Phenol |
| Vitamin B2 | Camphor |
| Vitamin B2 | Pectin |
| Vitamin B2 | *Eucalyptus* Oil |
| Vitamin B2 | Peppermint Oil |
| Vitamin B2 | Spearmint Oil |
| Vitamin B3 | Vitamin B5 |
| Vitamin B3 | Vitamin B6 |
| Vitamin B3 | Vitamin B7 |
| Vitamin B3 | Vitamin B8 |
| Vitamin B3 | Vitamin B9 |
| Vitamin B3 | Vitamin B12 |
| Vitamin B3 | Vitamin C |
| Vitamin B3 | Vitamin E |
| Vitamin B3 | Zinc |
| Vitamin B3 | Magnesium |
| Vitamin B3 | Selenium |
| Vitamin B3 | *Echinacea* |
| Vitamin B3 | Olive leaf (*olea europaea*) |
| Vitamin B3 | Wild indigo (*baptisia tinctoria*) |
| Vitamin B3 | Goldenseal (*hydrastis canadensis*) |
| Vitamin B3 | Fenugreek |
| Vitamin B3 | Mullein |
| Vitamin B3 | Phenol |
| Vitamin B3 | Camphor |
| Vitamin B3 | Pectin |
| Vitamin B3 | *Eucalyptus* Oil |
| Vitamin B3 | Peppermint Oil |
| Vitamin B3 | Spearmint Oil |
| Vitamin B5 | Vitamin B6 |
| Vitamin B5 | Vitamin B7 |
| Vitamin B5 | Vitamin B8 |
| Vitamin B5 | Vitamin B9 |
| Vitamin B5 | Vitamin B12 |
| Vitamin B5 | Vitamin C |
| Vitamin B5 | Vitamin E |
| Vitamin B5 | Zinc |
| Vitamin B5 | Magnesium |
| Vitamin B5 | Selenium |
| Vitamin B5 | *Echinacea* |
| Vitamin B5 | Olive leaf (*olea europaea*) |
| Vitamin B5 | Wild indigo (*baptisia tinctoria*) |
| Vitamin B5 | Goldenseal (*hydrastis canadensis*) |
| Vitamin B5 | Fenugreek |
| Vitamin B5 | Mullein |
| Vitamin B5 | Phenol |
| Vitamin B5 | Camphor |
| Vitamin B5 | Pectin |
| Vitamin B5 | *Eucalyptus* Oil |
| Vitamin B5 | Peppermint Oil |
| Vitamin B5 | Spearmint Oil |

TABLE 2-continued

Two Ingredient Combinations

| First Ingredient | Second Ingredient |
|---|---|
| Vitamin B6 | Vitamin B7 |
| Vitamin B6 | Vitamin B8 |
| Vitamin B6 | Vitamin B9 |
| Vitamin B6 | Vitamin B12 |
| Vitamin B6 | Vitamin C |
| Vitamin B6 | Vitamin E |
| Vitamin B6 | Zinc |
| Vitamin B6 | Magnesium |
| Vitamin B6 | Selenium |
| Vitamin B6 | Echinacea |
| Vitamin B6 | Olive leaf (*olea europaea*) |
| Vitamin B6 | Wild indigo (*baptisia tinctoria*) |
| Vitamin B6 | Goldenseal (*hydrastis canadensis*) |
| Vitamin B6 | Fenugreek |
| Vitamin B6 | Mullein |
| Vitamin B6 | Phenol |
| Vitamin B6 | Camphor |
| Vitamin B6 | Pectin |
| Vitamin B6 | *Eucalyptus* Oil |
| Vitamin B6 | Peppermint Oil |
| Vitamin B6 | Spearmint Oil |
| Vitamin B7 | Vitamin B8 |
| Vitamin B7 | Vitamin B9 |
| Vitamin B7 | Vitamin B12 |
| Vitamin B7 | Vitamin C |
| Vitamin B7 | Vitamin E |
| Vitamin B7 | Zinc |
| Vitamin B7 | Magnesium |
| Vitamin B7 | Selenium |
| Vitamin B7 | Echinacea |
| Vitamin B7 | Olive leaf (*olea europaea*) |
| Vitamin B7 | Wild indigo (*baptisia tinctoria*) |
| Vitamin B7 | Goldenseal (*hydrastis canadensis*) |
| Vitamin B7 | Fenugreek |
| Vitamin B7 | Mullein |
| Vitamin B7 | Phenol |
| Vitamin B7 | Camphor |
| Vitamin B7 | Pectin |
| Vitamin B7 | *Eucalyptus* Oil |
| Vitamin B7 | Peppermint Oil |
| Vitamin B7 | Spearmint Oil |
| Vitamin B8 | Vitamin B9 |
| Vitamin B8 | Vitamin B12 |
| Vitamin B8 | Vitamin C |
| Vitamin B8 | Vitamin E |
| Vitamin B8 | Zinc |
| Vitamin B8 | Magnesium |
| Vitamin B8 | Selenium |
| Vitamin B8 | Echinacea |
| Vitamin B8 | Olive leaf (*olea europaea*) |
| Vitamin B8 | Wild indigo (*baptisia tinctoria*) |
| Vitamin B8 | Goldenseal (*hydrastis canadensis*) |
| Vitamin B8 | Fenugreek |
| Vitamin B8 | Mullein |
| Vitamin B8 | Phenol |
| Vitamin B8 | Camphor |
| Vitamin B8 | Pectin |
| Vitamin B8 | *Eucalyptus* Oil |
| Vitamin B8 | Peppermint Oil |
| Vitamin B8 | Spearmint Oil |
| Vitamin B9 | Vitamin B12 |
| Vitamin B9 | Vitamin C |
| Vitamin B9 | Vitamin E |
| Vitamin B9 | Zinc |
| Vitamin B9 | Magnesium |
| Vitamin B9 | Selenium |
| Vitamin B9 | Echinacea |
| Vitamin B9 | Olive leaf (*olea europaea*) |
| Vitamin B9 | Wild indigo (*baptisia tinctoria*) |
| Vitamin B9 | Goldenseal (*hydrastis canadensis*) |
| Vitamin B9 | Fenugreek |
| Vitamin B9 | Mullein |
| Vitamin B9 | Phenol |
| Vitamin B9 | Camphor |
| Vitamin B9 | Pectin |
| Vitamin B9 | *Eucalyptus* Oil |
| Vitamin B9 | Peppermint Oil |
| Vitamin B9 | Spearmint Oil |
| Vitamin B12 | Vitamin C |
| Vitamin B12 | Vitamin E |
| Vitamin B12 | Zinc |
| Vitamin B12 | Magnesium |
| Vitamin B12 | Selenium |
| Vitamin B12 | Echinacea |
| Vitamin B12 | Olive leaf (*olea europaea*) |
| Vitamin B12 | Wild indigo (*baptisia tinctoria*) |
| Vitamin B12 | Goldenseal (*hydrastis canadensis*) |
| Vitamin B12 | Fenugreek |
| Vitamin B12 | Mullein |
| Vitamin B12 | Phenol |
| Vitamin B12 | Camphor |
| Vitamin B12 | Pectin |
| Vitamin B12 | *Eucalyptus* Oil |
| Vitamin B12 | Peppermint Oil |
| Vitamin B12 | Spearmint Oil |
| Vitamin C | Vitamin E |
| Vitamin C | Zinc |
| Vitamin C | Magnesium |
| Vitamin C | Selenium |
| Vitamin C | Echinacea |
| Vitamin C | Olive leaf (*olea europaea*) |
| Vitamin C | Wild indigo (*baptisia tinctoria*) |
| Vitamin C | Goldenseal (*hydrastis canadensis*) |
| Vitamin C | Fenugreek |
| Vitamin C | Mullein |
| Vitamin C | Phenol |
| Vitamin C | Camphor |
| Vitamin C | Pectin |
| Vitamin C | *Eucalyptus* Oil |
| Vitamin C | Peppermint Oil |
| Vitamin C | Spearmint Oil |
| Vitamin E | Zinc |
| Vitamin E | Magnesium |
| Vitamin E | Selenium |
| Vitamin E | Echinacea |
| Vitamin E | Olive leaf (*olea europaea*) |
| Vitamin E | Wild indigo (*baptisia tinctoria*) |
| Vitamin E | Goldenseal (*hydrastis canadensis*) |
| Vitamin E | Fenugreek |
| Vitamin E | Mullein |
| Vitamin E | Phenol |
| Vitamin E | Camphor |
| Vitamin E | Pectin |
| Vitamin E | *Eucalyptus* Oil |
| Vitamin E | Peppermint Oil |
| Vitamin E | Spearmint Oil |
| Zinc | Magnesium |
| Zinc | Selenium |
| Zinc | Echinacea |
| Zinc | Olive leaf (*olea europaea*) |
| Zinc | Wild indigo (*baptisia tinctoria*) |
| Zinc | Goldenseal (*hydrastis canadensis*) |
| Zinc | Fenugreek |
| Zinc | Mullein |
| Zinc | Phenol |
| Zinc | Camphor |
| Zinc | Pectin |
| Zinc | *Eucalyptus* Oil |
| Zinc | Peppermint Oil |
| Zinc | Spearmint Oil |
| Magnesium | Selenium |
| Magnesium | Echinacea |
| Magnesium | Olive leaf (*olea europaea*) |
| Magnesium | Wild indigo (*baptisia tinctoria*) |
| Magnesium | Goldenseal (*hydrastis canadensis*) |
| Magnesium | Fenugreek |
| Magnesium | Mullein |
| Magnesium | Phenol |
| Magnesium | Camphor |
| Magnesium | Pectin |
| Magnesium | *Eucalyptus* Oil |
| Magnesium | Peppermint Oil |

TABLE 2-continued

Two Ingredient Combinations

| First Ingredient | Second Ingredient |
| --- | --- |
| Magnesium | Spearmint Oil |
| Selenium | Echinacea |
| Selenium | Olive leaf (olea europaea) |
| Selenium | Wild indigo (baptisia tinctoria) |
| Selenium | Goldenseal (hydrastis canadensis) |
| Selenium | Fenugreek |
| Selenium | Mullein |
| Selenium | Phenol |
| Selenium | Camphor |
| Selenium | Pectin |
| Selenium | Eucalyptus Oil |
| Selenium | Peppermint Oil |
| Selenium | Spearmint Oil |
| Echinacea | Olive leaf (olea europaea) |
| Echinacea | Wild indigo (baptisia tinctoria) |
| Echinacea | Goldenseal (hydrastis canadensis) |
| Echinacea | Fenugreek |
| Echinacea | Mullein |
| Echinacea | Phenol |
| Echinacea | Camphor |
| Echinacea | Pectin |
| Echinacea | Eucalyptus Oil |
| Echinacea | Peppermint Oil |
| Echinacea | Spearmint Oil |
| Olive leaf (olea europaea) | Wild indigo (baptisia tinctoria) |
| Olive leaf (olea europaea) | Goldenseal (hydrastis canadensis) |
| Olive leaf (olea europaea) | Fenugreek |
| Olive leaf (olea europaea) | Mullein |
| Olive leaf (olea europaea) | Phenol |
| Olive leaf (olea europaea) | Camphor |
| Olive leaf (olea europaea) | Pectin |
| Olive leaf (olea europaea) | Eucalyptus Oil |
| Olive leaf (olea europaea) | Peppermint Oil |
| Olive leaf (olea europaea) | Spearmint Oil |
| Wild indigo (baptisia tinctoria) | Goldenseal (hydrastis canadensis) |
| Wild indigo (baptisia tinctoria) | Fenugreek |
| Wild indigo (baptisia tinctoria) | Mullein |
| Wild indigo (baptisia tinctoria) | Phenol |
| Wild indigo (baptisia tinctoria) | Camphor |
| Wild indigo (baptisia tinctoria) | Pectin |
| Wild indigo (baptisia tinctoria) | Eucalyptus Oil |
| Wild indigo (baptisia tinctoria) | Peppermint Oil |
| Wild indigo (baptisia tinctoria) | Spearmint Oil |
| Goldenseal (hydrastis canadensis) | Fenugreek |
| Goldenseal (hydrastis canadensis) | Mullein |
| Goldenseal (hydrastis canadensis) | Phenol |
| Goldenseal (hydrastis canadensis) | Camphor |
| Goldenseal (hydrastis canadensis) | Pectin |
| Goldenseal (hydrastis canadensis) | Eucalyptus Oil |
| Goldenseal (hydrastis canadensis) | Peppermint Oil |
| Goldenseal (hydrastis canadensis) | Spearmint Oil |
| Fenugreek | Mullein |
| Fenugreek | Phenol |
| Fenugreek | Camphor |
| Fenugreek | Pectin |
| Fenugreek | Eucalyptus Oil |
| Fenugreek | Peppermint Oil |
| Fenugreek | Spearmint Oil |
| Mullein | Phenol |
| Mullein | Camphor |
| Mullein | Pectin |
| Mullein | Eucalyptus Oil |
| Mullein | Peppermint Oil |
| Mullein | Spearmint Oil |
| Phenol | Camphor |
| Phenol | Pectin |
| Phenol | Eucalyptus Oil |
| Phenol | Peppermint Oil |
| Phenol | Spearmint Oil |
| Camphor | Pectin |
| Camphor | Eucalyptus Oil |
| Camphor | Peppermint Oil |
| Camphor | Spearmint Oil |
| Pectin | Eucalyptus Oil |
| Pectin | Peppermint Oil |
| Pectin | Spearmint Oil |
| Eucalyptus Oil | Peppermint Oil |
| Eucalyptus Oil | Spearmint Oil |
| Peppermint Oil | Spearmint Oil |

For example, in some embodiments, the composition includes (e.g., comprises, consists of, or consists essentially of) 3 or more ingredients selected from the combinations listed in Table 3.

TABLE 3

Three Ingredient Combinations

| First Ingredient | Second Ingredient | Third Ingredient |
| --- | --- | --- |
| Vitamin A | Vitamin B1 | Vitamin B2 |
| Vitamin A | Vitamin B1 | Vitamin B3 |
| Vitamin A | Vitamin B1 | Vitamin B5 |
| Vitamin A | Vitamin B1 | Vitamin B6 |
| Vitamin A | Vitamin B1 | Vitamin B7 |
| Vitamin A | Vitamin B1 | Vitamin B8 |
| Vitamin A | Vitamin B1 | Vitamin B9 |
| Vitamin A | Vitamin B1 | Vitamin B12 |
| Vitamin A | Vitamin B1 | Vitamin C |
| Vitamin A | Vitamin B1 | Vitamin E |
| Vitamin A | Vitamin B1 | Zinc |
| Vitamin A | Vitamin B1 | Magnesium |
| Vitamin A | Vitamin B1 | Selenium |
| Vitamin A | Vitamin B1 | Echinacea |
| Vitamin A | Vitamin B1 | Olive leaf (olea europaea) |
| Vitamin A | Vitamin B1 | Wild indigo (baptisia tinctoria) |
| Vitamin A | Vitamin B1 | Goldenseal (hydrastis canadensis) |
| Vitamin A | Vitamin B1 | Fenugreek |
| Vitamin A | Vitamin B1 | Mullein |
| Vitamin A | Vitamin B1 | Phenol |
| Vitamin A | Vitamin B1 | Camphor |
| Vitamin A | Vitamin B1 | Pectin |
| Vitamin A | Vitamin B1 | Eucalyptus Oil |
| Vitamin A | Vitamin B1 | Peppermint Oil |
| Vitamin A | Vitamin B1 | Spearmint Oil |

TABLE 3-continued

| Three Ingredient Combinations | | |
|---|---|---|
| First Ingredient | Second Ingredient | Third Ingredient |
| Vitamin A | Vitamin B2 | Vitamin B3 |
| Vitamin A | Vitamin B2 | Vitamin B5 |
| Vitamin A | Vitamin B2 | Vitamin B6 |
| Vitamin A | Vitamin B2 | Vitamin B7 |
| Vitamin A | Vitamin B2 | Vitamin B8 |
| Vitamin A | Vitamin B2 | Vitamin B9 |
| Vitamin A | Vitamin B2 | Vitamin B12 |
| Vitamin A | Vitamin B2 | Vitamin C |
| Vitamin A | Vitamin B2 | Vitamin E |
| Vitamin A | Vitamin B2 | Zinc |
| Vitamin A | Vitamin B2 | Magnesium |
| Vitamin A | Vitamin B2 | Selenium |
| Vitamin A | Vitamin B2 | *Echinacea* |
| Vitamin A | Vitamin B2 | Olive leaf (*olea europaea*) |
| Vitamin A | Vitamin B2 | Wild indigo (*baptisia tinctoria*) |
| Vitamin A | Vitamin B2 | Goldenseal (*hydrastis canadensis*) |
| Vitamin A | Vitamin B2 | Fenugreek |
| Vitamin A | Vitamin B2 | Mullein |
| Vitamin A | Vitamin B2 | Phenol |
| Vitamin A | Vitamin B2 | Camphor |
| Vitamin A | Vitamin B2 | Pectin |
| Vitamin A | Vitamin B2 | *Eucalyptus* Oil |
| Vitamin A | Vitamin B2 | Peppermint Oil |
| Vitamin A | Vitamin B2 | Spearmint Oil |
| Vitamin A | Vitamin B3 | Vitamin B5 |
| Vitamin A | Vitamin B3 | Vitamin B6 |
| Vitamin A | Vitamin B3 | Vitamin B7 |
| Vitamin A | Vitamin B3 | Vitamin B8 |
| Vitamin A | Vitamin B3 | Vitamin B9 |
| Vitamin A | Vitamin B3 | Vitamin B12 |
| Vitamin A | Vitamin B3 | Vitamin C |
| Vitamin A | Vitamin B3 | Vitamin E |
| Vitamin A | Vitamin B3 | Zinc |
| Vitamin A | Vitamin B3 | Magnesium |
| Vitamin A | Vitamin B3 | Selenium |
| Vitamin A | Vitamin B3 | *Echinacea* |
| Vitamin A | Vitamin B3 | Olive leaf (*olea europaea*) |
| Vitamin A | Vitamin B3 | Wild indigo (*baptisia tinctoria*) |
| Vitamin A | Vitamin B3 | Goldenseal (*hydrastis canadensis*) |
| Vitamin A | Vitamin B3 | Fenugreek |
| Vitamin A | Vitamin B3 | Mullein |
| Vitamin A | Vitamin B3 | Phenol |
| Vitamin A | Vitamin B3 | Camphor |
| Vitamin A | Vitamin B3 | Pectin |
| Vitamin A | Vitamin B3 | *Eucalyptus* Oil |
| Vitamin A | Vitamin B3 | Peppermint Oil |
| Vitamin A | Vitamin B3 | Spearmint Oil |
| Vitamin A | Vitamin B5 | Vitamin B6 |
| Vitamin A | Vitamin B5 | Vitamin B7 |
| Vitamin A | Vitamin B5 | Vitamin B8 |
| Vitamin A | Vitamin B5 | Vitamin B9 |
| Vitamin A | Vitamin B5 | Vitamin B12 |
| Vitamin A | Vitamin B5 | Vitamin C |
| Vitamin A | Vitamin B5 | Vitamin E |
| Vitamin A | Vitamin B5 | Zinc |
| Vitamin A | Vitamin B5 | Magnesium |
| Vitamin A | Vitamin B5 | Selenium |
| Vitamin A | Vitamin B5 | *Echinacea* |
| Vitamin A | Vitamin B5 | Olive leaf (*olea europaea*) |
| Vitamin A | Vitamin B5 | Wild indigo (*baptisia tinctoria*) |
| Vitamin A | Vitamin B5 | Goldenseal (*hydrastis canadensis*) |
| Vitamin A | Vitamin B5 | Fenugreek |
| Vitamin A | Vitamin B5 | Mullein |
| Vitamin A | Vitamin B5 | Phenol |
| Vitamin A | Vitamin B5 | Camphor |
| Vitamin A | Vitamin B5 | Pectin |
| Vitamin A | Vitamin B5 | *Eucalyptus* Oil |
| Vitamin A | Vitamin B5 | Peppermint Oil |
| Vitamin A | Vitamin B5 | Spearmint Oil |
| Vitamin A | Vitamin B6 | Vitamin B7 |
| Vitamin A | Vitamin B6 | Vitamin B8 |
| Vitamin A | Vitamin B6 | Vitamin B9 |
| Vitamin A | Vitamin B6 | Vitamin B12 |
| Vitamin A | Vitamin B6 | Vitamin C |
| Vitamin A | Vitamin B6 | Vitamin E |
| Vitamin A | Vitamin B6 | Zinc |

TABLE 3-continued

Three Ingredient Combinations

| First Ingredient | Second Ingredient | Third Ingredient |
| --- | --- | --- |
| Vitamin A | Vitamin B6 | Magnesium |
| Vitamin A | Vitamin B6 | Selenium |
| Vitamin A | Vitamin B6 | *Echinacea* |
| Vitamin A | Vitamin B6 | Olive leaf (*olea europaea*) |
| Vitamin A | Vitamin B6 | Wild indigo (*baptisia tinctoria*) |
| Vitamin A | Vitamin B6 | Goldenseal (*hydrastis canadensis*) |
| Vitamin A | Vitamin B6 | Fenugreek |
| Vitamin A | Vitamin B6 | Mullein |
| Vitamin A | Vitamin B6 | Phenol |
| Vitamin A | Vitamin B6 | Camphor |
| Vitamin A | Vitamin B6 | Pectin |
| Vitamin A | Vitamin B6 | *Eucalyptus* Oil |
| Vitamin A | Vitamin B6 | Peppermint Oil |
| Vitamin A | Vitamin B6 | Spearmint Oil |
| Vitamin A | Vitamin B7 | Vitamin B8 |
| Vitamin A | Vitamin B7 | Vitamin B9 |
| Vitamin A | Vitamin B7 | Vitamin B12 |
| Vitamin A | Vitamin B7 | Vitamin C |
| Vitamin A | Vitamin B7 | Vitamin E |
| Vitamin A | Vitamin B7 | Zinc |
| Vitamin A | Vitamin B7 | Magnesium |
| Vitamin A | Vitamin B7 | Selenium |
| Vitamin A | Vitamin B7 | *Echinacea* |
| Vitamin A | Vitamin B7 | Olive leaf (*olea europaea*) |
| Vitamin A | Vitamin B7 | Wild indigo (*baptisia tinctoria*) |
| Vitamin A | Vitamin B7 | Goldenseal (*hydrastis canadensis*) |
| Vitamin A | Vitamin B7 | Fenugreek |
| Vitamin A | Vitamin B7 | Mullein |
| Vitamin A | Vitamin B7 | Phenol |
| Vitamin A | Vitamin B7 | Camphor |
| Vitamin A | Vitamin B7 | Pectin |
| Vitamin A | Vitamin B7 | *Eucalyptus* Oil |
| Vitamin A | Vitamin B7 | Peppermint Oil |
| Vitamin A | Vitamin B7 | Spearmint Oil |
| Vitamin A | Vitamin B8 | Vitamin B9 |
| Vitamin A | Vitamin B8 | Vitamin B12 |
| Vitamin A | Vitamin B8 | Vitamin C |
| Vitamin A | Vitamin B8 | Vitamin E |
| Vitamin A | Vitamin B8 | Zinc |
| Vitamin A | Vitamin B8 | Magnesium |
| Vitamin A | Vitamin B8 | Selenium |
| Vitamin A | Vitamin B8 | *Echinacea* |
| Vitamin A | Vitamin B8 | Olive leaf (*olea europaea*) |
| Vitamin A | Vitamin B8 | Wild indigo (*baptisia tinctoria*) |
| Vitamin A | Vitamin B8 | Goldenseal (*hydrastis canadensis*) |
| Vitamin A | Vitamin B8 | Fenugreek |
| Vitamin A | Vitamin B8 | Mullein |
| Vitamin A | Vitamin B8 | Phenol |
| Vitamin A | Vitamin B8 | Camphor |
| Vitamin A | Vitamin B8 | Pectin |
| Vitamin A | Vitamin B8 | *Eucalyptus* Oil |
| Vitamin A | Vitamin B8 | Peppermint Oil |
| Vitamin A | Vitamin B8 | Spearmint Oil |
| Vitamin A | Vitamin B9 | Vitamin B12 |
| Vitamin A | Vitamin B9 | Vitamin C |
| Vitamin A | Vitamin B9 | Vitamin E |
| Vitamin A | Vitamin B9 | Zinc |
| Vitamin A | Vitamin B9 | Magnesium |
| Vitamin A | Vitamin B9 | Selenium |
| Vitamin A | Vitamin B9 | *Echinacea* |
| Vitamin A | Vitamin B9 | Olive leaf (*olea europaea*) |
| Vitamin A | Vitamin B9 | Wild indigo (*baptisia tinctoria*) |
| Vitamin A | Vitamin B9 | Goldenseal (*hydrastis canadensis*) |
| Vitamin A | Vitamin B9 | Fenugreek |
| Vitamin A | Vitamin B9 | Mullein |
| Vitamin A | Vitamin B9 | Phenol |
| Vitamin A | Vitamin B9 | Camphor |
| Vitamin A | Vitamin B9 | Pectin |
| Vitamin A | Vitamin B9 | *Eucalyptus* Oil |
| Vitamin A | Vitamin B9 | Peppermint Oil |
| Vitamin A | Vitamin B9 | Spearmint Oil |
| Vitamin A | Vitamin B12 | Vitamin C |
| Vitamin A | Vitamin B12 | Vitamin E |
| Vitamin A | Vitamin B12 | Zinc |
| Vitamin A | Vitamin B12 | Magnesium |
| Vitamin A | Vitamin B12 | Selenium |

TABLE 3-continued

Three Ingredient Combinations

| First Ingredient | Second Ingredient | Third Ingredient |
| --- | --- | --- |
| Vitamin A | Vitamin B12 | *Echinacea* |
| Vitamin A | Vitamin B12 | Olive leaf (*olea europaea*) |
| Vitamin A | Vitamin B12 | Wild indigo (*baptisia tinctoria*) |
| Vitamin A | Vitamin B12 | Goldenseal (*hydrastis canadensis*) |
| Vitamin A | Vitamin B12 | Fenugreek |
| Vitamin A | Vitamin B12 | Mullein |
| Vitamin A | Vitamin B12 | Phenol |
| Vitamin A | Vitamin B12 | Camphor |
| Vitamin A | Vitamin B12 | Pectin |
| Vitamin A | Vitamin B12 | *Eucalyptus* Oil |
| Vitamin A | Vitamin B12 | Peppermint Oil |
| Vitamin A | Vitamin B12 | Spearmint Oil |
| Vitamin A | Vitamin C | Vitamin E |
| Vitamin A | Vitamin C | Zinc |
| Vitamin A | Vitamin C | Magnesium |
| Vitamin A | Vitamin C | Selenium |
| Vitamin A | Vitamin C | *Echinacea* |
| Vitamin A | Vitamin C | Olive leaf (*olea europaea*) |
| Vitamin A | Vitamin C | Wild indigo (*baptisia tinctoria*) |
| Vitamin A | Vitamin C | Goldenseal (*hydrastis canadensis*) |
| Vitamin A | Vitamin C | Fenugreek |
| Vitamin A | Vitamin C | Mullein |
| Vitamin A | Vitamin C | Phenol |
| Vitamin A | Vitamin C | Camphor |
| Vitamin A | Vitamin C | Pectin |
| Vitamin A | Vitamin C | *Eucalyptus* Oil |
| Vitamin A | Vitamin C | Peppermint Oil |
| Vitamin A | Vitamin C | Spearmint Oil |
| Vitamin A | Vitamin E | Zinc |
| Vitamin A | Vitamin E | Magnesium |
| Vitamin A | Vitamin E | Selenium |
| Vitamin A | Vitamin E | *Echinacea* |
| Vitamin A | Vitamin E | Olive leaf (*olea europaea*) |
| Vitamin A | Vitamin E | Wild indigo (*baptisia tinctoria*) |
| Vitamin A | Vitamin E | Goldenseal (*hydrastis canadensis*) |
| Vitamin A | Vitamin E | Fenugreek |
| Vitamin A | Vitamin E | Mullein |
| Vitamin A | Vitamin E | Phenol |
| Vitamin A | Vitamin E | Camphor |
| Vitamin A | Vitamin E | Pectin |
| Vitamin A | Vitamin E | *Eucalyptus* Oil |
| Vitamin A | Vitamin E | Peppermint Oil |
| Vitamin A | Vitamin E | Spearmint Oil |
| Vitamin A | Zinc | Magnesium |
| Vitamin A | Zinc | Selenium |
| Vitamin A | Zinc | *Echinacea* |
| Vitamin A | Zinc | Olive leaf (*olea europaea*) |
| Vitamin A | Zinc | Wild indigo (*baptisia tinctoria*) |
| Vitamin A | Zinc | Goldenseal (*hydrastis canadensis*) |
| Vitamin A | Zinc | Fenugreek |
| Vitamin A | Zinc | Mullein |
| Vitamin A | Zinc | Phenol |
| Vitamin A | Zinc | Camphor |
| Vitamin A | Zinc | Pectin |
| Vitamin A | Zinc | *Eucalyptus* Oil |
| Vitamin A | Zinc | Peppermint Oil |
| Vitamin A | Zinc | Spearmint Oil |
| Vitamin A | Magnesium | Selenium |
| Vitamin A | Magnesium | *Echinacea* |
| Vitamin A | Magnesium | Olive leaf (*olea europaea*) |
| Vitamin A | Magnesium | Wild indigo (*baptisia tinctoria*) |
| Vitamin A | Magnesium | Goldenseal (*hydrastis canadensis*) |
| Vitamin A | Magnesium | Fenugreek |
| Vitamin A | Magnesium | Mullein |
| Vitamin A | Magnesium | Phenol |
| Vitamin A | Magnesium | Camphor |
| Vitamin A | Magnesium | Pectin |
| Vitamin A | Magnesium | *Eucalyptus* Oil |
| Vitamin A | Magnesium | Peppermint Oil |
| Vitamin A | Magnesium | Spearmint Oil |
| Vitamin A | Selenium | *Echinacea* |
| Vitamin A | Selenium | Olive leaf (*olea europaea*) |
| Vitamin A | Selenium | Wild indigo (*baptisia tinctoria*) |
| Vitamin A | Selenium | Goldenseal (*hydrastis canadensis*) |
| Vitamin A | Selenium | Fenugreek |
| Vitamin A | Selenium | Mullein |

TABLE 3-continued

Three Ingredient Combinations

| First Ingredient | Second Ingredient | Third Ingredient |
| --- | --- | --- |
| Vitamin A | Selenium | Phenol |
| Vitamin A | Selenium | Camphor |
| Vitamin A | Selenium | Pectin |
| Vitamin A | Selenium | Eucalyptus Oil |
| Vitamin A | Selenium | Peppermint Oil |
| Vitamin A | Selenium | Spearmint Oil |
| Vitamin A | Echinacea | Olive leaf (olea europaea) |
| Vitamin A | Echinacea | Wild indigo (baptisia tinctoria) |
| Vitamin A | Echinacea | Goldenseal (hydrastis canadensis) |
| Vitamin A | Echinacea | Fenugreek |
| Vitamin A | Echinacea | Mullein |
| Vitamin A | Echinacea | Phenol |
| Vitamin A | Echinacea | Camphor |
| Vitamin A | Echinacea | Pectin |
| Vitamin A | Echinacea | Eucalyptus Oil |
| Vitamin A | Echinacea | Peppermint Oil |
| Vitamin A | Echinacea | Spearmint Oil |
| Vitamin A | Olive leaf (olea europaea) | Wild indigo (baptisia tinctoria) |
| Vitamin A | Olive leaf (olea europaea) | Goldenseal (hydrastis canadensis) |
| Vitamin A | Olive leaf (olea europaea) | Fenugreek |
| Vitamin A | Olive leaf (olea europaea) | Mullein |
| Vitamin A | Olive leaf (olea europaea) | Phenol |
| Vitamin A | Olive leaf (olea europaea) | Camphor |
| Vitamin A | Olive leaf (olea europaea) | Pectin |
| Vitamin A | Olive leaf (olea europaea) | Eucalyptus Oil |
| Vitamin A | Olive leaf (olea europaea) | Peppermint Oil |
| Vitamin A | Olive leaf (olea europaea) | Spearmint Oil |
| Vitamin A | Wild indigo (baptisia tinctoria) | Goldenseal (hydrastis canadensis) |
| Vitamin A | Wild indigo (baptisia tinctoria) | Fenugreek |
| Vitamin A | Wild indigo (baptisia tinctoria) | Mullein |
| Vitamin A | Wild indigo (baptisia tinctoria) | Phenol |
| Vitamin A | Wild indigo (baptisia tinctoria) | Camphor |
| Vitamin A | Wild indigo (baptisia tinctoria) | Pectin |
| Vitamin A | Wild indigo (baptisia tinctoria) | Eucalyptus Oil |
| Vitamin A | Wild indigo (baptisia tinctoria) | Peppermint Oil |
| Vitamin A | Wild indigo (baptisia tinctoria) | Spearmint Oil |
| Vitamin A | Goldenseal (hydrastis canadensis) | Fenugreek |
| Vitamin A | Goldenseal (hydrastis canadensis) | Mullein |
| Vitamin A | Goldenseal (hydrastis canadensis) | Phenol |
| Vitamin A | Goldenseal (hydrastis canadensis) | Camphor |
| Vitamin A | Goldenseal (hydrastis canadensis) | Pectin |
| Vitamin A | Goldenseal (hydrastis canadensis) | Eucalyptus Oil |
| Vitamin A | Goldenseal (hydrastis canadensis) | Peppermint Oil |
| Vitamin A | Goldenseal (hydrastis canadensis) | Spearmint Oil |
| Vitamin A | Fenugreek | Mullein |
| Vitamin A | Fenugreek | Phenol |
| Vitamin A | Fenugreek | Camphor |
| Vitamin A | Fenugreek | Pectin |
| Vitamin A | Fenugreek | Eucalyptus Oil |
| Vitamin A | Fenugreek | Peppermint Oil |
| Vitamin A | Fenugreek | Spearmint Oil |
| Vitamin A | Mullein | Phenol |
| Vitamin A | Mullein | Camphor |
| Vitamin A | Mullein | Pectin |
| Vitamin A | Mullein | Eucalyptus Oil |
| Vitamin A | Mullein | Peppermint Oil |
| Vitamin A | Mullein | Spearmint Oil |
| Vitamin A | Phenol | Camphor |
| Vitamin A | Phenol | Pectin |
| Vitamin A | Phenol | Eucalyptus Oil |
| Vitamin A | Phenol | Peppermint Oil |
| Vitamin A | Phenol | Spearmint Oil |
| Vitamin A | Camphor | Pectin |
| Vitamin A | Camphor | Eucalyptus Oil |
| Vitamin A | Camphor | Peppermint Oil |
| Vitamin A | Camphor | Spearmint Oil |
| Vitamin A | Pectin | Eucalyptus Oil |
| Vitamin A | Pectin | Peppermint Oil |
| Vitamin A | Pectin | Spearmint Oil |
| Vitamin A | Eucalyptus Oil | Peppermint Oil |
| Vitamin A | Eucalyptus Oil | Spearmint Oil |
| Vitamin A | Peppermint Oil | Spearmint Oil |
| Vitamin B1 | Vitamin B2 | Vitamin B3 |
| Vitamin B1 | Vitamin B2 | Vitamin B5 |
| Vitamin B1 | Vitamin B2 | Vitamin B6 |
| Vitamin B1 | Vitamin B2 | Vitamin B7 |

TABLE 3-continued

Three Ingredient Combinations

| First Ingredient | Second Ingredient | Third Ingredient |
| --- | --- | --- |
| Vitamin B1 | Vitamin B2 | Vitamin B8 |
| Vitamin B1 | Vitamin B2 | Vitamin B9 |
| Vitamin B1 | Vitamin B2 | Vitamin B12 |
| Vitamin B1 | Vitamin B2 | Vitamin C |
| Vitamin B1 | Vitamin B2 | Vitamin E |
| Vitamin B1 | Vitamin B2 | Zinc |
| Vitamin B1 | Vitamin B2 | Magnesium |
| Vitamin B1 | Vitamin B2 | Selenium |
| Vitamin B1 | Vitamin B2 | *Echinacea* |
| Vitamin B1 | Vitamin B2 | Olive leaf (*olea europaea*) |
| Vitamin B1 | Vitamin B2 | Wild indigo (*baptisia tinctoria*) |
| Vitamin B1 | Vitamin B2 | Goldenseal (*hydrastis canadensis*) |
| Vitamin B1 | Vitamin B2 | Fenugreek |
| Vitamin B1 | Vitamin B2 | Mullein |
| Vitamin B1 | Vitamin B2 | Phenol |
| Vitamin B1 | Vitamin B2 | Camphor |
| Vitamin B1 | Vitamin B2 | Pectin |
| Vitamin B1 | Vitamin B2 | *Eucalyptus* Oil |
| Vitamin B1 | Vitamin B2 | Peppermint Oil |
| Vitamin B1 | Vitamin B2 | Spearmint Oil |
| Vitamin B1 | Vitamin B3 | Vitamin B5 |
| Vitamin B1 | Vitamin B3 | Vitamin B6 |
| Vitamin B1 | Vitamin B3 | Vitamin B7 |
| Vitamin B1 | Vitamin B3 | Vitamin B8 |
| Vitamin B1 | Vitamin B3 | Vitamin B9 |
| Vitamin B1 | Vitamin B3 | Vitamin B12 |
| Vitamin B1 | Vitamin B3 | Vitamin C |
| Vitamin B1 | Vitamin B3 | Vitamin E |
| Vitamin B1 | Vitamin B3 | Zinc |
| Vitamin B1 | Vitamin B3 | Magnesium |
| Vitamin B1 | Vitamin B3 | Selenium |
| Vitamin B1 | Vitamin B3 | *Echinacea* |
| Vitamin B1 | Vitamin B3 | Olive leaf (*olea europaea*) |
| Vitamin B1 | Vitamin B3 | Wild indigo (*baptisia tinctoria*) |
| Vitamin B1 | Vitamin B3 | Goldenseal (*hydrastis canadensis*) |
| Vitamin B1 | Vitamin B3 | Fenugreek |
| Vitamin B1 | Vitamin B3 | Mullein |
| Vitamin B1 | Vitamin B3 | Phenol |
| Vitamin B1 | Vitamin B3 | Camphor |
| Vitamin B1 | Vitamin B3 | Pectin |
| Vitamin B1 | Vitamin B3 | *Eucalyptus* Oil |
| Vitamin B1 | Vitamin B3 | Peppermint Oil |
| Vitamin B1 | Vitamin B3 | Spearmint Oil |
| Vitamin B1 | Vitamin B5 | Vitamin B6 |
| Vitamin B1 | Vitamin B5 | Vitamin B7 |
| Vitamin B1 | Vitamin B5 | Vitamin B8 |
| Vitamin B1 | Vitamin B5 | Vitamin B9 |
| Vitamin B1 | Vitamin B5 | Vitamin B12 |
| Vitamin B1 | Vitamin B5 | Vitamin C |
| Vitamin B1 | Vitamin B5 | Vitamin E |
| Vitamin B1 | Vitamin B5 | Zinc |
| Vitamin B1 | Vitamin B5 | Magnesium |
| Vitamin B1 | Vitamin B5 | Selenium |
| Vitamin B1 | Vitamin B5 | *Echinacea* |
| Vitamin B1 | Vitamin B5 | Olive leaf (*olea europaea*) |
| Vitamin B1 | Vitamin B5 | Wild indigo (*baptisia tinctoria*) |
| Vitamin B1 | Vitamin B5 | Goldenseal (*hydrastis canadensis*) |
| Vitamin B1 | Vitamin B5 | Fenugreek |
| Vitamin B1 | Vitamin B5 | Mullein |
| Vitamin B1 | Vitamin B5 | Phenol |
| Vitamin B1 | Vitamin B5 | Camphor |
| Vitamin B1 | Vitamin B5 | Pectin |
| Vitamin B1 | Vitamin B5 | *Eucalyptus* Oil |
| Vitamin B1 | Vitamin B5 | Peppermint Oil |
| Vitamin B1 | Vitamin B5 | Spearmint Oil |
| Vitamin B1 | Vitamin B6 | Vitamin B7 |
| Vitamin B1 | Vitamin B6 | Vitamin B8 |
| Vitamin B1 | Vitamin B6 | Vitamin B9 |
| Vitamin B1 | Vitamin B6 | Vitamin B12 |
| Vitamin B1 | Vitamin B6 | Vitamin C |
| Vitamin B1 | Vitamin B6 | Vitamin E |
| Vitamin B1 | Vitamin B6 | Zinc |
| Vitamin B1 | Vitamin B6 | Magnesium |
| Vitamin B1 | Vitamin B6 | Selenium |
| Vitamin B1 | Vitamin B6 | *Echinacea* |
| Vitamin B1 | Vitamin B6 | Olive leaf (*olea europaea*) |

TABLE 3-continued

Three Ingredient Combinations

| First Ingredient | Second Ingredient | Third Ingredient |
| --- | --- | --- |
| Vitamin B1 | Vitamin B6 | Wild indigo (*baptisia tinctoria*) |
| Vitamin B1 | Vitamin B6 | Goldenseal (*hydrastis canadensis*) |
| Vitamin B1 | Vitamin B6 | Fenugreek |
| Vitamin B1 | Vitamin B6 | Mullein |
| Vitamin B1 | Vitamin B6 | Phenol |
| Vitamin B1 | Vitamin B6 | Camphor |
| Vitamin B1 | Vitamin B6 | Pectin |
| Vitamin B1 | Vitamin B6 | *Eucalyptus* Oil |
| Vitamin B1 | Vitamin B6 | Peppermint Oil |
| Vitamin B1 | Vitamin B6 | Spearmint Oil |
| Vitamin B1 | Vitamin B7 | Vitamin B8 |
| Vitamin B1 | Vitamin B7 | Vitamin B9 |
| Vitamin B1 | Vitamin B7 | Vitamin B12 |
| Vitamin B1 | Vitamin B7 | Vitamin C |
| Vitamin B1 | Vitamin B7 | Vitamin E |
| Vitamin B1 | Vitamin B7 | Zinc |
| Vitamin B1 | Vitamin B7 | Magnesium |
| Vitamin B1 | Vitamin B7 | Selenium |
| Vitamin B1 | Vitamin B7 | Echinacea |
| Vitamin B1 | Vitamin B7 | Olive leaf (*olea europaea*) |
| Vitamin B1 | Vitamin B7 | Wild indigo (*baptisia tinctoria*) |
| Vitamin B1 | Vitamin B7 | Goldenseal (*hydrastis canadensis*) |
| Vitamin B1 | Vitamin B7 | Fenugreek |
| Vitamin B1 | Vitamin B7 | Mullein |
| Vitamin B1 | Vitamin B7 | Phenol |
| Vitamin B1 | Vitamin B7 | Camphor |
| Vitamin B1 | Vitamin B7 | Pectin |
| Vitamin B1 | Vitamin B7 | *Eucalyptus* Oil |
| Vitamin B1 | Vitamin B7 | Peppermint Oil |
| Vitamin B1 | Vitamin B7 | Spearmint Oil |
| Vitamin B1 | Vitamin B8 | Vitamin B9 |
| Vitamin B1 | Vitamin B8 | Vitamin B12 |
| Vitamin B1 | Vitamin B8 | Vitamin C |
| Vitamin B1 | Vitamin B8 | Vitamin E |
| Vitamin B1 | Vitamin B8 | Zinc |
| Vitamin B1 | Vitamin B8 | Magnesium |
| Vitamin B1 | Vitamin B8 | Selenium |
| Vitamin B1 | Vitamin B8 | Echinacea |
| Vitamin B1 | Vitamin B8 | Olive leaf (*olea europaea*) |
| Vitamin B1 | Vitamin B8 | Wild indigo (*baptisia tinctoria*) |
| Vitamin B1 | Vitamin B8 | Goldenseal (*hydrastis canadensis*) |
| Vitamin B1 | Vitamin B8 | Fenugreek |
| Vitamin B1 | Vitamin B8 | Mullein |
| Vitamin B1 | Vitamin B8 | Phenol |
| Vitamin B1 | Vitamin B8 | Camphor |
| Vitamin B1 | Vitamin B8 | Pectin |
| Vitamin B1 | Vitamin B8 | *Eucalyptus* Oil |
| Vitamin B1 | Vitamin B8 | Peppermint Oil |
| Vitamin B1 | Vitamin B8 | Spearmint Oil |
| Vitamin B1 | Vitamin B9 | Vitamin B12 |
| Vitamin B1 | Vitamin B9 | Vitamin C |
| Vitamin B1 | Vitamin B9 | Vitamin E |
| Vitamin B1 | Vitamin B9 | Zinc |
| Vitamin B1 | Vitamin B9 | Magnesium |
| Vitamin B1 | Vitamin B9 | Selenium |
| Vitamin B1 | Vitamin B9 | Echinacea |
| Vitamin B1 | Vitamin B9 | Olive leaf (*olea europaea*) |
| Vitamin B1 | Vitamin B9 | Wild indigo (*baptisia tinctoria*) |
| Vitamin B1 | Vitamin B9 | Goldenseal (*hydrastis canadensis*) |
| Vitamin B1 | Vitamin B9 | Fenugreek |
| Vitamin B1 | Vitamin B9 | Mullein |
| Vitamin B1 | Vitamin B9 | Phenol |
| Vitamin B1 | Vitamin B9 | Camphor |
| Vitamin B1 | Vitamin B9 | Pectin |
| Vitamin B1 | Vitamin B9 | *Eucalyptus* Oil |
| Vitamin B1 | Vitamin B9 | Peppermint Oil |
| Vitamin B1 | Vitamin B9 | Spearmint Oil |
| Vitamin B1 | Vitamin B12 | Vitamin C |
| Vitamin B1 | Vitamin B12 | Vitamin E |
| Vitamin B1 | Vitamin B12 | Zinc |
| Vitamin B1 | Vitamin B12 | Magnesium |
| Vitamin B1 | Vitamin B12 | Selenium |
| Vitamin B1 | Vitamin B12 | Echinacea |
| Vitamin B1 | Vitamin B12 | Olive leaf (*olea europaea*) |
| Vitamin B1 | Vitamin B12 | Wild indigo (*baptisia tinctoria*) |
| Vitamin B1 | Vitamin B12 | Goldenseal (*hydrastis canadensis*) |

TABLE 3-continued

Three Ingredient Combinations

| First Ingredient | Second Ingredient | Third Ingredient |
| --- | --- | --- |
| Vitamin B1 | Vitamin B12 | Fenugreek |
| Vitamin B1 | Vitamin B12 | Mullein |
| Vitamin B1 | Vitamin B12 | Phenol |
| Vitamin B1 | Vitamin B12 | Camphor |
| Vitamin B1 | Vitamin B12 | Pectin |
| Vitamin B1 | Vitamin B12 | *Eucalyptus* Oil |
| Vitamin B1 | Vitamin B12 | Peppermint Oil |
| Vitamin B1 | Vitamin B12 | Spearmint Oil |
| Vitamin B1 | Vitamin C | Vitamin E |
| Vitamin B1 | Vitamin C | Zinc |
| Vitamin B1 | Vitamin C | Magnesium |
| Vitamin B1 | Vitamin C | Selenium |
| Vitamin B1 | Vitamin C | *Echinacea* |
| Vitamin B1 | Vitamin C | Olive leaf (*olea europaea*) |
| Vitamin B1 | Vitamin C | Wild indigo (*baptisia tinctoria*) |
| Vitamin B1 | Vitamin C | Goldenseal (*hydrastis canadensis*) |
| Vitamin B1 | Vitamin C | Fenugreek |
| Vitamin B1 | Vitamin C | Mullein |
| Vitamin B1 | Vitamin C | Phenol |
| Vitamin B1 | Vitamin C | Camphor |
| Vitamin B1 | Vitamin C | Pectin |
| Vitamin B1 | Vitamin C | *Eucalyptus* Oil |
| Vitamin B1 | Vitamin C | Peppermint Oil |
| Vitamin B1 | Vitamin C | Spearmint Oil |
| Vitamin B1 | Vitamin E | Zinc |
| Vitamin B1 | Vitamin E | Magnesium |
| Vitamin B1 | Vitamin E | Selenium |
| Vitamin B1 | Vitamin E | *Echinacea* |
| Vitamin B1 | Vitamin E | Olive leaf (*olea europaea*) |
| Vitamin B1 | Vitamin E | Wild indigo (*baptisia tinctoria*) |
| Vitamin B1 | Vitamin E | Goldenseal (*hydrastis canadensis*) |
| Vitamin B1 | Vitamin E | Fenugreek |
| Vitamin B1 | Vitamin E | Mullein |
| Vitamin B1 | Vitamin E | Phenol |
| Vitamin B1 | Vitamin E | Camphor |
| Vitamin B1 | Vitamin E | Pectin |
| Vitamin B1 | Vitamin E | *Eucalyptus* Oil |
| Vitamin B1 | Vitamin E | Peppermint Oil |
| Vitamin B1 | Vitamin E | Spearmint Oil |
| Vitamin B1 | Zinc | Magnesium |
| Vitamin B1 | Zinc | Selenium |
| Vitamin B1 | Zinc | *Echinacea* |
| Vitamin B1 | Zinc | Olive leaf (*olea europaea*) |
| Vitamin B1 | Zinc | Wild indigo (*baptisia tinctoria*) |
| Vitamin B1 | Zinc | Goldenseal (*hydrastis canadensis*) |
| Vitamin B1 | Zinc | Fenugreek |
| Vitamin B1 | Zinc | Mullein |
| Vitamin B1 | Zinc | Phenol |
| Vitamin B1 | Zinc | Camphor |
| Vitamin B1 | Zinc | Pectin |
| Vitamin B1 | Zinc | *Eucalyptus* Oil |
| Vitamin B1 | Zinc | Peppermint Oil |
| Vitamin B1 | Zinc | Spearmint Oil |
| Vitamin B1 | Magnesium | Selenium |
| Vitamin B1 | Magnesium | *Echinacea* |
| Vitamin B1 | Magnesium | Olive leaf (*olea europaea*) |
| Vitamin B1 | Magnesium | Wild indigo (*baptisia tinctoria*) |
| Vitamin B1 | Magnesium | Goldenseal (*hydrastis canadensis*) |
| Vitamin B1 | Magnesium | Fenugreek |
| Vitamin B1 | Magnesium | Mullein |
| Vitamin B1 | Magnesium | Phenol |
| Vitamin B1 | Magnesium | Camphor |
| Vitamin B1 | Magnesium | Pectin |
| Vitamin B1 | Magnesium | *Eucalyptus* Oil |
| Vitamin B1 | Magnesium | Peppermint Oil |
| Vitamin B1 | Magnesium | Spearmint Oil |
| Vitamin B1 | Selenium | *Echinacea* |
| Vitamin B1 | Selenium | Olive leaf (*olea europaea*) |
| Vitamin B1 | Selenium | Wild indigo (*baptisia tinctoria*) |
| Vitamin B1 | Selenium | Goldenseal (*hydrastis canadensis*) |
| Vitamin B1 | Selenium | Fenugreek |
| Vitamin B1 | Selenium | Mullein |
| Vitamin B1 | Selenium | Phenol |
| Vitamin B1 | Selenium | Camphor |
| Vitamin B1 | Selenium | Pectin |
| Vitamin B1 | Selenium | *Eucalyptus* Oil |

TABLE 3-continued

Three Ingredient Combinations

| First Ingredient | Second Ingredient | Third Ingredient |
| --- | --- | --- |
| Vitamin B1 | Selenium | Peppermint Oil |
| Vitamin B1 | Selenium | Spearmint Oil |
| Vitamin B1 | *Echinacea* | Olive leaf (*olea europaea*) |
| Vitamin B1 | *Echinacea* | Wild indigo (*baptisia tinctoria*) |
| Vitamin B1 | *Echinacea* | Goldenseal (*hydrastis canadensis*) |
| Vitamin B1 | *Echinacea* | Fenugreek |
| Vitamin B1 | *Echinacea* | Mullein |
| Vitamin B1 | *Echinacea* | Phenol |
| Vitamin B1 | *Echinacea* | Camphor |
| Vitamin B1 | *Echinacea* | Pectin |
| Vitamin B1 | *Echinacea* | *Eucalyptus* Oil |
| Vitamin B1 | *Echinacea* | Peppermint Oil |
| Vitamin B1 | *Echinacea* | Spearmint Oil |
| Vitamin B1 | Olive leaf (*olea europaea*) | Wild indigo (*baptisia tinctoria*) |
| Vitamin B1 | Olive leaf (*olea europaea*) | Goldenseal (*hydrastis canadensis*) |
| Vitamin B1 | Olive leaf (*olea europaea*) | Fenugreek |
| Vitamin B1 | Olive leaf (*olea europaea*) | Mullein |
| Vitamin B1 | Olive leaf (*olea europaea*) | Phenol |
| Vitamin B1 | Olive leaf (*olea europaea*) | Camphor |
| Vitamin B1 | Olive leaf (*olea europaea*) | Pectin |
| Vitamin B1 | Olive leaf (*olea europaea*) | *Eucalyptus* Oil |
| Vitamin B1 | Olive leaf (*olea europaea*) | Peppermint Oil |
| Vitamin B1 | Olive leaf (*olea europaea*) | Spearmint Oil |
| Vitamin B1 | Wild indigo (*baptisia tinctoria*) | Goldenseal (*hydrastis canadensis*) |
| Vitamin B1 | Wild indigo (*baptisia tinctoria*) | Fenugreek |
| Vitamin B1 | Wild indigo (*baptisia tinctoria*) | Mullein |
| Vitamin B1 | Wild indigo (*baptisia tinctoria*) | Phenol |
| Vitamin B1 | Wild indigo (*baptisia tinctoria*) | Camphor |
| Vitamin B1 | Wild indigo (*baptisia tinctoria*) | Pectin |
| Vitamin B1 | Wild indigo (*baptisia tinctoria*) | *Eucalyptus* Oil |
| Vitamin B1 | Wild indigo (*baptisia tinctoria*) | Peppermint Oil |
| Vitamin B1 | Wild indigo (*baptisia tinctoria*) | Spearmint Oil |
| Vitamin B1 | Goldenseal (*hydrastis canadensis*) | Fenugreek |
| Vitamin B1 | Goldenseal (*hydrastis canadensis*) | Mullein |
| Vitamin B1 | Goldenseal (*hydrastis canadensis*) | Phenol |
| Vitamin B1 | Goldenseal (*hydrastis canadensis*) | Camphor |
| Vitamin B1 | Goldenseal (*hydrastis canadensis*) | Pectin |
| Vitamin B1 | Goldenseal (*hydrastis canadensis*) | *Eucalyptus* Oil |
| Vitamin B1 | Goldenseal (*hydrastis canadensis*) | Peppermint Oil |
| Vitamin B1 | Goldenseal (*hydrastis canadensis*) | Spearmint Oil |
| Vitamin B1 | Fenugreek | Mullein |
| Vitamin B1 | Fenugreek | Phenol |
| Vitamin B1 | Fenugreek | Camphor |
| Vitamin B1 | Fenugreek | Pectin |
| Vitamin B1 | Fenugreek | *Eucalyptus* Oil |
| Vitamin B1 | Fenugreek | Peppermint Oil |
| Vitamin B1 | Fenugreek | Spearmint Oil |
| Vitamin B1 | Mullein | Phenol |
| Vitamin B1 | Mullein | Camphor |
| Vitamin B1 | Mullein | Pectin |
| Vitamin B1 | Mullein | *Eucalyptus* Oil |
| Vitamin B1 | Mullein | Peppermint Oil |
| Vitamin B1 | Mullein | Spearmint Oil |
| Vitamin B1 | Phenol | Camphor |
| Vitamin B1 | Phenol | Pectin |
| Vitamin B1 | Phenol | *Eucalyptus* Oil |
| Vitamin B1 | Phenol | Peppermint Oil |
| Vitamin B1 | Phenol | Spearmint Oil |
| Vitamin B1 | Camphor | Pectin |
| Vitamin B1 | Camphor | *Eucalyptus* Oil |
| Vitamin B1 | Camphor | Peppermint Oil |
| Vitamin B1 | Camphor | Spearmint Oil |
| Vitamin B1 | Pectin | *Eucalyptus* Oil |
| Vitamin B1 | Pectin | Peppermint Oil |
| Vitamin B1 | Pectin | Spearmint Oil |
| Vitamin B1 | *Eucalyptus* Oil | Peppermint Oil |
| Vitamin B1 | *Eucalyptus* Oil | Spearmint Oil |
| Vitamin B1 | Peppermint Oil | Spearmint Oil |
| Vitamin B2 | Vitamin B3 | Vitamin B5 |
| Vitamin B2 | Vitamin B3 | Vitamin B6 |
| Vitamin B2 | Vitamin B3 | Vitamin B7 |
| Vitamin B2 | Vitamin B3 | Vitamin B8 |
| Vitamin B2 | Vitamin B3 | Vitamin B9 |
| Vitamin B2 | Vitamin B3 | Vitamin B12 |
| Vitamin B2 | Vitamin B3 | Vitamin C |
| Vitamin B2 | Vitamin B3 | Vitamin E |

TABLE 3-continued

Three Ingredient Combinations

| First Ingredient | Second Ingredient | Third Ingredient |
| --- | --- | --- |
| Vitamin B2 | Vitamin B3 | Zinc |
| Vitamin B2 | Vitamin B3 | Magnesium |
| Vitamin B2 | Vitamin B3 | Selenium |
| Vitamin B2 | Vitamin B3 | *Echinacea* |
| Vitamin B2 | Vitamin B3 | Olive leaf (*olea europaea*) |
| Vitamin B2 | Vitamin B3 | Wild indigo (*baptisia tinctoria*) |
| Vitamin B2 | Vitamin B3 | Goldenseal (*hydrastis canadensis*) |
| Vitamin B2 | Vitamin B3 | Fenugreek |
| Vitamin B2 | Vitamin B3 | Mullein |
| Vitamin B2 | Vitamin B3 | Phenol |
| Vitamin B2 | Vitamin B3 | Camphor |
| Vitamin B2 | Vitamin B3 | Pectin |
| Vitamin B2 | Vitamin B3 | *Eucalyptus* Oil |
| Vitamin B2 | Vitamin B3 | Peppermint Oil |
| Vitamin B2 | Vitamin B3 | Spearmint Oil |
| Vitamin B2 | Vitamin B5 | Vitamin B6 |
| Vitamin B2 | Vitamin B5 | Vitamin B7 |
| Vitamin B2 | Vitamin B5 | Vitamin B8 |
| Vitamin B2 | Vitamin B5 | Vitamin B9 |
| Vitamin B2 | Vitamin B5 | Vitamin B12 |
| Vitamin B2 | Vitamin B5 | Vitamin C |
| Vitamin B2 | Vitamin B5 | Vitamin E |
| Vitamin B2 | Vitamin B5 | Zinc |
| Vitamin B2 | Vitamin B5 | Magnesium |
| Vitamin B2 | Vitamin B5 | Selenium |
| Vitamin B2 | Vitamin B5 | *Echinacea* |
| Vitamin B2 | Vitamin B5 | Olive leaf (*olea europaea*) |
| Vitamin B2 | Vitamin B5 | Wild indigo (*baptisia tinctoria*) |
| Vitamin B2 | Vitamin B5 | Goldenseal (*hydrastis canadensis*) |
| Vitamin B2 | Vitamin B5 | Fenugreek |
| Vitamin B2 | Vitamin B5 | Mullein |
| Vitamin B2 | Vitamin B5 | Phenol |
| Vitamin B2 | Vitamin B5 | Camphor |
| Vitamin B2 | Vitamin B5 | Pectin |
| Vitamin B2 | Vitamin B5 | *Eucalyptus* Oil |
| Vitamin B2 | Vitamin B5 | Peppermint Oil |
| Vitamin B2 | Vitamin B5 | Spearmint Oil |
| Vitamin B2 | Vitamin B6 | Vitamin B7 |
| Vitamin B2 | Vitamin B6 | Vitamin B8 |
| Vitamin B2 | Vitamin B6 | Vitamin B9 |
| Vitamin B2 | Vitamin B6 | Vitamin B12 |
| Vitamin B2 | Vitamin B6 | Vitamin C |
| Vitamin B2 | Vitamin B6 | Vitamin E |
| Vitamin B2 | Vitamin B6 | Zinc |
| Vitamin B2 | Vitamin B6 | Magnesium |
| Vitamin B2 | Vitamin B6 | Selenium |
| Vitamin B2 | Vitamin B6 | *Echinacea* |
| Vitamin B2 | Vitamin B6 | Olive leaf (*olea europaea*) |
| Vitamin B2 | Vitamin B6 | Wild indigo (*baptisia tinctoria*) |
| Vitamin B2 | Vitamin B6 | Goldenseal (*hydrastis canadensis*) |
| Vitamin B2 | Vitamin B6 | Fenugreek |
| Vitamin B2 | Vitamin B6 | Mullein |
| Vitamin B2 | Vitamin B6 | Phenol |
| Vitamin B2 | Vitamin B6 | Camphor |
| Vitamin B2 | Vitamin B6 | Pectin |
| Vitamin B2 | Vitamin B6 | *Eucalyptus* Oil |
| Vitamin B2 | Vitamin B6 | Peppermint Oil |
| Vitamin B2 | Vitamin B6 | Spearmint Oil |
| Vitamin B2 | Vitamin B7 | Vitamin B8 |
| Vitamin B2 | Vitamin B7 | Vitamin B9 |
| Vitamin B2 | Vitamin B7 | Vitamin B12 |
| Vitamin B2 | Vitamin B7 | Vitamin C |
| Vitamin B2 | Vitamin B7 | Vitamin E |
| Vitamin B2 | Vitamin B7 | Zinc |
| Vitamin B2 | Vitamin B7 | Magnesium |
| Vitamin B2 | Vitamin B7 | Selenium |
| Vitamin B2 | Vitamin B7 | *Echinacea* |
| Vitamin B2 | Vitamin B7 | Olive leaf (*olea europaea*) |
| Vitamin B2 | Vitamin B7 | Wild indigo (*baptisia tinctoria*) |
| Vitamin B2 | Vitamin B7 | Goldenseal (*hydrastis canadensis*) |
| Vitamin B2 | Vitamin B7 | Fenugreek |
| Vitamin B2 | Vitamin B7 | Mullein |
| Vitamin B2 | Vitamin B7 | Phenol |
| Vitamin B2 | Vitamin B7 | Camphor |
| Vitamin B2 | Vitamin B7 | Pectin |
| Vitamin B2 | Vitamin B7 | *Eucalyptus* Oil |

TABLE 3-continued

Three Ingredient Combinations

| First Ingredient | Second Ingredient | Third Ingredient |
| --- | --- | --- |
| Vitamin B2 | Vitamin B7 | Peppermint Oil |
| Vitamin B2 | Vitamin B7 | Spearmint Oil |
| Vitamin B2 | Vitamin B8 | Vitamin B9 |
| Vitamin B2 | Vitamin B8 | Vitamin B12 |
| Vitamin B2 | Vitamin B8 | Vitamin C |
| Vitamin B2 | Vitamin B8 | Vitamin E |
| Vitamin B2 | Vitamin B8 | Zinc |
| Vitamin B2 | Vitamin B8 | Magnesium |
| Vitamin B2 | Vitamin B8 | Selenium |
| Vitamin B2 | Vitamin B8 | *Echinacea* |
| Vitamin B2 | Vitamin B8 | Olive leaf (*olea europaea*) |
| Vitamin B2 | Vitamin B8 | Wild indigo (*baptisia tinctoria*) |
| Vitamin B2 | Vitamin B8 | Goldenseal (*hydrastis canadensis*) |
| Vitamin B2 | Vitamin B8 | Fenugreek |
| Vitamin B2 | Vitamin B8 | Mullein |
| Vitamin B2 | Vitamin B8 | Phenol |
| Vitamin B2 | Vitamin B8 | Camphor |
| Vitamin B2 | Vitamin B8 | Pectin |
| Vitamin B2 | Vitamin B8 | *Eucalyptus* Oil |
| Vitamin B2 | Vitamin B8 | Peppermint Oil |
| Vitamin B2 | Vitamin B8 | Spearmint Oil |
| Vitamin B2 | Vitamin B9 | Vitamin B12 |
| Vitamin B2 | Vitamin B9 | Vitamin C |
| Vitamin B2 | Vitamin B9 | Vitamin E |
| Vitamin B2 | Vitamin B9 | Zinc |
| Vitamin B2 | Vitamin B9 | Magnesium |
| Vitamin B2 | Vitamin B9 | Selenium |
| Vitamin B2 | Vitamin B9 | *Echinacea* |
| Vitamin B2 | Vitamin B9 | Olive leaf (*olea europaea*) |
| Vitamin B2 | Vitamin B9 | Wild indigo (*baptisia tinctoria*) |
| Vitamin B2 | Vitamin B9 | Goldenseal (*hydrastis canadensis*) |
| Vitamin B2 | Vitamin B9 | Fenugreek |
| Vitamin B2 | Vitamin B9 | Mullein |
| Vitamin B2 | Vitamin B9 | Phenol |
| Vitamin B2 | Vitamin B9 | Camphor |
| Vitamin B2 | Vitamin B9 | Pectin |
| Vitamin B2 | Vitamin B9 | *Eucalyptus* Oil |
| Vitamin B2 | Vitamin B9 | Peppermint Oil |
| Vitamin B2 | Vitamin B9 | Spearmint Oil |
| Vitamin B2 | Vitamin B12 | Vitamin C |
| Vitamin B2 | Vitamin B12 | Vitamin E |
| Vitamin B2 | Vitamin B12 | Zinc |
| Vitamin B2 | Vitamin B12 | Magnesium |
| Vitamin B2 | Vitamin B12 | Selenium |
| Vitamin B2 | Vitamin B12 | *Echinacea* |
| Vitamin B2 | Vitamin B12 | Olive leaf (*olea europaea*) |
| Vitamin B2 | Vitamin B12 | Wild indigo (*baptisia tinctoria*) |
| Vitamin B2 | Vitamin B12 | Goldenseal (*hydrastis canadensis*) |
| Vitamin B2 | Vitamin B12 | Fenugreek |
| Vitamin B2 | Vitamin B12 | Mullein |
| Vitamin B2 | Vitamin B12 | Phenol |
| Vitamin B2 | Vitamin B12 | Camphor |
| Vitamin B2 | Vitamin B12 | Pectin |
| Vitamin B2 | Vitamin B12 | *Eucalyptus* Oil |
| Vitamin B2 | Vitamin B12 | Peppermint Oil |
| Vitamin B2 | Vitamin B12 | Spearmint Oil |
| Vitamin B2 | Vitamin C | Vitamin E |
| Vitamin B2 | Vitamin C | Zinc |
| Vitamin B2 | Vitamin C | Magnesium |
| Vitamin B2 | Vitamin C | Selenium |
| Vitamin B2 | Vitamin C | *Echinacea* |
| Vitamin B2 | Vitamin C | Olive leaf (*olea europaea*) |
| Vitamin B2 | Vitamin C | Wild indigo (*baptisia tinctoria*) |
| Vitamin B2 | Vitamin C | Goldenseal (*hydrastis canadensis*) |
| Vitamin B2 | Vitamin C | Fenugreek |
| Vitamin B2 | Vitamin C | Mullein |
| Vitamin B2 | Vitamin C | Phenol |
| Vitamin B2 | Vitamin C | Camphor |
| Vitamin B2 | Vitamin C | Pectin |
| Vitamin B2 | Vitamin C | *Eucalyptus* Oil |
| Vitamin B2 | Vitamin C | Peppermint Oil |
| Vitamin B2 | Vitamin C | Spearmint Oil |
| Vitamin B2 | Vitamin E | Zinc |
| Vitamin B2 | Vitamin E | Magnesium |
| Vitamin B2 | Vitamin E | Selenium |
| Vitamin B2 | Vitamin E | *Echinacea* |

TABLE 3-continued

Three Ingredient Combinations

| First Ingredient | Second Ingredient | Third Ingredient |
| --- | --- | --- |
| Vitamin B2 | Vitamin E | Olive leaf (*olea europaea*) |
| Vitamin B2 | Vitamin E | Wild indigo (*baptisia tinctoria*) |
| Vitamin B2 | Vitamin E | Goldenseal (*hydrastis canadensis*) |
| Vitamin B2 | Vitamin E | Fenugreek |
| Vitamin B2 | Vitamin E | Mullein |
| Vitamin B2 | Vitamin E | Phenol |
| Vitamin B2 | Vitamin E | Camphor |
| Vitamin B2 | Vitamin E | Pectin |
| Vitamin B2 | Vitamin E | *Eucalyptus* Oil |
| Vitamin B2 | Vitamin E | Peppermint Oil |
| Vitamin B2 | Vitamin E | Spearmint Oil |
| Vitamin B2 | Zinc | Magnesium |
| Vitamin B2 | Zinc | Selenium |
| Vitamin B2 | Zinc | *Echinacea* |
| Vitamin B2 | Zinc | Olive leaf (*olea europaea*) |
| Vitamin B2 | Zinc | Wild indigo (*baptisia tinctoria*) |
| Vitamin B2 | Zinc | Goldenseal (*hydrastis canadensis*) |
| Vitamin B2 | Zinc | Fenugreek |
| Vitamin B2 | Zinc | Mullein |
| Vitamin B2 | Zinc | Phenol |
| Vitamin B2 | Zinc | Camphor |
| Vitamin B2 | Zinc | Pectin |
| Vitamin B2 | Zinc | *Eucalyptus* Oil |
| Vitamin B2 | Zinc | Peppermint Oil |
| Vitamin B2 | Zinc | Spearmint Oil |
| Vitamin B2 | Magnesium | Selenium |
| Vitamin B2 | Magnesium | *Echinacea* |
| Vitamin B2 | Magnesium | Olive leaf (*olea europaea*) |
| Vitamin B2 | Magnesium | Wild indigo (*baptisia tinctoria*) |
| Vitamin B2 | Magnesium | Goldenseal (*hydrastis canadensis*) |
| Vitamin B2 | Magnesium | Fenugreek |
| Vitamin B2 | Magnesium | Mullein |
| Vitamin B2 | Magnesium | Phenol |
| Vitamin B2 | Magnesium | Camphor |
| Vitamin B2 | Magnesium | Pectin |
| Vitamin B2 | Magnesium | *Eucalyptus* Oil |
| Vitamin B2 | Magnesium | Peppermint Oil |
| Vitamin B2 | Magnesium | Spearmint Oil |
| Vitamin B2 | Selenium | *Echinacea* |
| Vitamin B2 | Selenium | Olive leaf (*olea europaea*) |
| Vitamin B2 | Selenium | Wild indigo (*baptisia tinctoria*) |
| Vitamin B2 | Selenium | Goldenseal (*hydrastis canadensis*) |
| Vitamin B2 | Selenium | Fenugreek |
| Vitamin B2 | Selenium | Mullein |
| Vitamin B2 | Selenium | Phenol |
| Vitamin B2 | Selenium | Camphor |
| Vitamin B2 | Selenium | Pectin |
| Vitamin B2 | Selenium | *Eucalyptus* Oil |
| Vitamin B2 | Selenium | Peppermint Oil |
| Vitamin B2 | Selenium | Spearmint Oil |
| Vitamin B2 | *Echinacea* | Olive leaf (*olea europaea*) |
| Vitamin B2 | *Echinacea* | Wild indigo (*baptisia tinctoria*) |
| Vitamin B2 | *Echinacea* | Goldenseal (*hydrastis canadensis*) |
| Vitamin B2 | *Echinacea* | Fenugreek |
| Vitamin B2 | *Echinacea* | Mullein |
| Vitamin B2 | *Echinacea* | Phenol |
| Vitamin B2 | *Echinacea* | Camphor |
| Vitamin B2 | *Echinacea* | Pectin |
| Vitamin B2 | *Echinacea* | *Eucalyptus* Oil |
| Vitamin B2 | *Echinacea* | Peppermint Oil |
| Vitamin B2 | *Echinacea* | Spearmint Oil |
| Vitamin B2 | Olive leaf (*olea europaea*) | Wild indigo (*baptisia tinctoria*) |
| Vitamin B2 | Olive leaf (*olea europaea*) | Goldenseal (*hydrastis canadensis*) |
| Vitamin B2 | Olive leaf (*olea europaea*) | Fenugreek |
| Vitamin B2 | Olive leaf (*olea europaea*) | Mullein |
| Vitamin B2 | Olive leaf (*olea europaea*) | Phenol |
| Vitamin B2 | Olive leaf (*olea europaea*) | Camphor |
| Vitamin B2 | Olive leaf (*olea europaea*) | Pectin |
| Vitamin B2 | Olive leaf (*olea europaea*) | *Eucalyptus* Oil |
| Vitamin B2 | Olive leaf (*olea europaea*) | Peppermint Oil |
| Vitamin B2 | Olive leaf (*olea europaea*) | Spearmint Oil |
| Vitamin B2 | Wild indigo (*baptisia tinctoria*) | Goldenseal (*hydrastis canadensis*) |
| Vitamin B2 | Wild indigo (*baptisia tinctoria*) | Fenugreek |
| Vitamin B2 | Wild indigo (*baptisia tinctoria*) | Mullein |
| Vitamin B2 | Wild indigo (*baptisia tinctoria*) | Phenol |
| Vitamin B2 | Wild indigo (*baptisia tinctoria*) | Camphor |

TABLE 3-continued

Three Ingredient Combinations

| First Ingredient | Second Ingredient | Third Ingredient |
| --- | --- | --- |
| Vitamin B2 | Wild indigo (*baptisia tinctoria*) | Pectin |
| Vitamin B2 | Wild indigo (*baptisia tinctoria*) | *Eucalyptus* Oil |
| Vitamin B2 | Wild indigo (*baptisia tinctoria*) | Peppermint Oil |
| Vitamin B2 | Wild indigo (*baptisia tinctoria*) | Spearmint Oil |
| Vitamin B2 | Goldenseal (*hydrastis canadensis*) | Fenugreek |
| Vitamin B2 | Goldenseal (*hydrastis canadensis*) | Mullein |
| Vitamin B2 | Goldenseal (*hydrastis canadensis*) | Phenol |
| Vitamin B2 | Goldenseal (*hydrastis canadensis*) | Camphor |
| Vitamin B2 | Goldenseal (*hydrastis canadensis*) | Pectin |
| Vitamin B2 | Goldenseal (*hydrastis canadensis*) | *Eucalyptus* Oil |
| Vitamin B2 | Goldenseal (*hydrastis canadensis*) | Peppermint Oil |
| Vitamin B2 | Goldenseal (*hydrastis canadensis*) | Spearmint Oil |
| Vitamin B2 | Fenugreek | Mullein |
| Vitamin B2 | Fenugreek | Phenol |
| Vitamin B2 | Fenugreek | Camphor |
| Vitamin B2 | Fenugreek | Pectin |
| Vitamin B2 | Fenugreek | *Eucalyptus* Oil |
| Vitamin B2 | Fenugreek | Peppermint Oil |
| Vitamin B2 | Fenugreek | Spearmint Oil |
| Vitamin B2 | Mullein | Phenol |
| Vitamin B2 | Mullein | Camphor |
| Vitamin B2 | Mullein | Pectin |
| Vitamin B2 | Mullein | *Eucalyptus* Oil |
| Vitamin B2 | Mullein | Peppermint Oil |
| Vitamin B2 | Mullein | Spearmint Oil |
| Vitamin B2 | Phenol | Camphor |
| Vitamin B2 | Phenol | Pectin |
| Vitamin B2 | Phenol | *Eucalyptus* Oil |
| Vitamin B2 | Phenol | Peppermint Oil |
| Vitamin B2 | Phenol | Spearmint Oil |
| Vitamin B2 | Camphor | Pectin |
| Vitamin B2 | Camphor | *Eucalyptus* Oil |
| Vitamin B2 | Camphor | Peppermint Oil |
| Vitamin B2 | Camphor | Spearmint Oil |
| Vitamin B2 | Pectin | *Eucalyptus* Oil |
| Vitamin B2 | Pectin | Peppermint Oil |
| Vitamin B2 | Pectin | Spearmint Oil |
| Vitamin B2 | *Eucalyptus* Oil | Peppermint Oil |
| Vitamin B2 | *Eucalyptus* Oil | Spearmint Oil |
| Vitamin B2 | Peppermint Oil | Spearmint Oil |
| Vitamin B3 | Vitamin B5 | Vitamin B6 |
| Vitamin B3 | Vitamin B5 | Vitamin B7 |
| Vitamin B3 | Vitamin B5 | Vitamin B8 |
| Vitamin B3 | Vitamin B5 | Vitamin B9 |
| Vitamin B3 | Vitamin B5 | Vitamin B12 |
| Vitamin B3 | Vitamin B5 | Vitamin C |
| Vitamin B3 | Vitamin B5 | Vitamin E |
| Vitamin B3 | Vitamin B5 | Zinc |
| Vitamin B3 | Vitamin B5 | Magnesium |
| Vitamin B3 | Vitamin B5 | Selenium |
| Vitamin B3 | Vitamin B5 | *Echinacea* |
| Vitamin B3 | Vitamin B5 | Olive leaf (*olea europaea*) |
| Vitamin B3 | Vitamin B5 | Wild indigo (*baptisia tinctoria*) |
| Vitamin B3 | Vitamin B5 | Goldenseal (*hydrastis canadensis*) |
| Vitamin B3 | Vitamin B5 | Fenugreek |
| Vitamin B3 | Vitamin B5 | Mullein |
| Vitamin B3 | Vitamin B5 | Phenol |
| Vitamin B3 | Vitamin B5 | Camphor |
| Vitamin B3 | Vitamin B5 | Pectin |
| Vitamin B3 | Vitamin B5 | *Eucalyptus* Oil |
| Vitamin B3 | Vitamin B5 | Peppermint Oil |
| Vitamin B3 | Vitamin B5 | Spearmint Oil |
| Vitamin B3 | Vitamin B6 | Vitamin B7 |
| Vitamin B3 | Vitamin B6 | Vitamin B8 |
| Vitamin B3 | Vitamin B6 | Vitamin B9 |
| Vitamin B3 | Vitamin B6 | Vitamin B12 |
| Vitamin B3 | Vitamin B6 | Vitamin C |
| Vitamin B3 | Vitamin B6 | Vitamin E |
| Vitamin B3 | Vitamin B6 | Zinc |
| Vitamin B3 | Vitamin B6 | Magnesium |
| Vitamin B3 | Vitamin B6 | Selenium |
| Vitamin B3 | Vitamin B6 | *Echinacea* |
| Vitamin B3 | Vitamin B6 | Olive leaf (*olea europaea*) |
| Vitamin B3 | Vitamin B6 | Wild indigo (*baptisia tinctoria*) |
| Vitamin B3 | Vitamin B6 | Goldenseal (*hydrastis canadensis*) |
| Vitamin B3 | Vitamin B6 | Fenugreek |

TABLE 3-continued

Three Ingredient Combinations

| First Ingredient | Second Ingredient | Third Ingredient |
| --- | --- | --- |
| Vitamin B3 | Vitamin B6 | Mullein |
| Vitamin B3 | Vitamin B6 | Phenol |
| Vitamin B3 | Vitamin B6 | Camphor |
| Vitamin B3 | Vitamin B6 | Pectin |
| Vitamin B3 | Vitamin B6 | *Eucalyptus* Oil |
| Vitamin B3 | Vitamin B6 | Peppermint Oil |
| Vitamin B3 | Vitamin B6 | Spearmint Oil |
| Vitamin B3 | Vitamin B7 | Vitamin B8 |
| Vitamin B3 | Vitamin B7 | Vitamin B9 |
| Vitamin B3 | Vitamin B7 | Vitamin B12 |
| Vitamin B3 | Vitamin B7 | Vitamin C |
| Vitamin B3 | Vitamin B7 | Vitamin E |
| Vitamin B3 | Vitamin B7 | Zinc |
| Vitamin B3 | Vitamin B7 | Magnesium |
| Vitamin B3 | Vitamin B7 | Selenium |
| Vitamin B3 | Vitamin B7 | *Echinacea* |
| Vitamin B3 | Vitamin B7 | Olive leaf (*olea europaea*) |
| Vitamin B3 | Vitamin B7 | Wild indigo (*baptisia tinctoria*) |
| Vitamin B3 | Vitamin B7 | Goldenseal (*hydrastis canadensis*) |
| Vitamin B3 | Vitamin B7 | Fenugreek |
| Vitamin B3 | Vitamin B7 | Mullein |
| Vitamin B3 | Vitamin B7 | Phenol |
| Vitamin B3 | Vitamin B7 | Camphor |
| Vitamin B3 | Vitamin B7 | Pectin |
| Vitamin B3 | Vitamin B7 | *Eucalyptus* Oil |
| Vitamin B3 | Vitamin B7 | Peppermint Oil |
| Vitamin B3 | Vitamin B7 | Spearmint Oil |
| Vitamin B3 | Vitamin B8 | Vitamin B9 |
| Vitamin B3 | Vitamin B8 | Vitamin B12 |
| Vitamin B3 | Vitamin B8 | Vitamin C |
| Vitamin B3 | Vitamin B8 | Vitamin E |
| Vitamin B3 | Vitamin B8 | Zinc |
| Vitamin B3 | Vitamin B8 | Magnesium |
| Vitamin B3 | Vitamin B8 | Selenium |
| Vitamin B3 | Vitamin B8 | *Echinacea* |
| Vitamin B3 | Vitamin B8 | Olive leaf (*olea europaea*) |
| Vitamin B3 | Vitamin B8 | Wild indigo (*baptisia tinctoria*) |
| Vitamin B3 | Vitamin B8 | Goldenseal (*hydrastis canadensis*) |
| Vitamin B3 | Vitamin B8 | Fenugreek |
| Vitamin B3 | Vitamin B8 | Mullein |
| Vitamin B3 | Vitamin B8 | Phenol |
| Vitamin B3 | Vitamin B8 | Camphor |
| Vitamin B3 | Vitamin B8 | Pectin |
| Vitamin B3 | Vitamin B8 | *Eucalyptus* Oil |
| Vitamin B3 | Vitamin B8 | Peppermint Oil |
| Vitamin B3 | Vitamin B8 | Spearmint Oil |
| Vitamin B3 | Vitamin B9 | Vitamin B12 |
| Vitamin B3 | Vitamin B9 | Vitamin C |
| Vitamin B3 | Vitamin B9 | Vitamin E |
| Vitamin B3 | Vitamin B9 | Zinc |
| Vitamin B3 | Vitamin B9 | Magnesium |
| Vitamin B3 | Vitamin B9 | Selenium |
| Vitamin B3 | Vitamin B9 | *Echinacea* |
| Vitamin B3 | Vitamin B9 | Olive leaf (*olea europaea*) |
| Vitamin B3 | Vitamin B9 | Wild indigo (*baptisia tinctoria*) |
| Vitamin B3 | Vitamin B9 | Goldenseal (*hydrastis canadensis*) |
| Vitamin B3 | Vitamin B9 | Fenugreek |
| Vitamin B3 | Vitamin B9 | Mullein |
| Vitamin B3 | Vitamin B9 | Phenol |
| Vitamin B3 | Vitamin B9 | Camphor |
| Vitamin B3 | Vitamin B9 | Pectin |
| Vitamin B3 | Vitamin B9 | *Eucalyptus* Oil |
| Vitamin B3 | Vitamin B9 | Peppermint Oil |
| Vitamin B3 | Vitamin B9 | Spearmint Oil |
| Vitamin B3 | Vitamin B12 | Vitamin C |
| Vitamin B3 | Vitamin B12 | Vitamin E |
| Vitamin B3 | Vitamin B12 | Zinc |
| Vitamin B3 | Vitamin B12 | Magnesium |
| Vitamin B3 | Vitamin B12 | Selenium |
| Vitamin B3 | Vitamin B12 | *Echinacea* |
| Vitamin B3 | Vitamin B12 | Olive leaf (*olea europaea*) |
| Vitamin B3 | Vitamin B12 | Wild indigo (*baptisia tinctoria*) |
| Vitamin B3 | Vitamin B12 | Goldenseal (*hydrastis canadensis*) |
| Vitamin B3 | Vitamin B12 | Fenugreek |
| Vitamin B3 | Vitamin B12 | Mullein |
| Vitamin B3 | Vitamin B12 | Phenol |

TABLE 3-continued

| Three Ingredient Combinations | | |
|---|---|---|
| First Ingredient | Second Ingredient | Third Ingredient |
| Vitamin B3 | Vitamin B12 | Camphor |
| Vitamin B3 | Vitamin B12 | Pectin |
| Vitamin B3 | Vitamin B12 | *Eucalyptus* Oil |
| Vitamin B3 | Vitamin B12 | Peppermint Oil |
| Vitamin B3 | Vitamin B12 | Spearmint Oil |
| Vitamin B3 | Vitamin C | Vitamin E |
| Vitamin B3 | Vitamin C | Zinc |
| Vitamin B3 | Vitamin C | Magnesium |
| Vitamin B3 | Vitamin C | Selenium |
| Vitamin B3 | Vitamin C | *Echinacea* |
| Vitamin B3 | Vitamin C | Olive leaf (*olea europaea*) |
| Vitamin B3 | Vitamin C | Wild indigo (*baptisia tinctoria*) |
| Vitamin B3 | Vitamin C | Goldenseal (*hydrastis canadensis*) |
| Vitamin B3 | Vitamin C | Fenugreek |
| Vitamin B3 | Vitamin C | Mullein |
| Vitamin B3 | Vitamin C | Phenol |
| Vitamin B3 | Vitamin C | Camphor |
| Vitamin B3 | Vitamin C | Pectin |
| Vitamin B3 | Vitamin C | *Eucalyptus* Oil |
| Vitamin B3 | Vitamin C | Peppermint Oil |
| Vitamin B3 | Vitamin C | Spearmint Oil |
| Vitamin B3 | Vitamin E | Zinc |
| Vitamin B3 | Vitamin E | Magnesium |
| Vitamin B3 | Vitamin E | Selenium |
| Vitamin B3 | Vitamin E | *Echinacea* |
| Vitamin B3 | Vitamin E | Olive leaf (*olea europaea*) |
| Vitamin B3 | Vitamin E | Wild indigo (*baptisia tinctoria*) |
| Vitamin B3 | Vitamin E | Goldenseal (*hydrastis canadensis*) |
| Vitamin B3 | Vitamin E | Fenugreek |
| Vitamin B3 | Vitamin E | Mullein |
| Vitamin B3 | Vitamin E | Phenol |
| Vitamin B3 | Vitamin E | Camphor |
| Vitamin B3 | Vitamin E | Pectin |
| Vitamin B3 | Vitamin E | *Eucalyptus* Oil |
| Vitamin B3 | Vitamin E | Peppermint Oil |
| Vitamin B3 | Vitamin E | Spearmint Oil |
| Vitamin B3 | Zinc | Magnesium |
| Vitamin B3 | Zinc | Selenium |
| Vitamin B3 | Zinc | *Echinacea* |
| Vitamin B3 | Zinc | Olive leaf (*olea europaea*) |
| Vitamin B3 | Zinc | Wild indigo (*baptisia tinctoria*) |
| Vitamin B3 | Zinc | Goldenseal (*hydrastis canadensis*) |
| Vitamin B3 | Zinc | Fenugreek |
| Vitamin B3 | Zinc | Mullein |
| Vitamin B3 | Zinc | Phenol |
| Vitamin B3 | Zinc | Camphor |
| Vitamin B3 | Zinc | Pectin |
| Vitamin B3 | Zinc | *Eucalyptus* Oil |
| Vitamin B3 | Zinc | Peppermint Oil |
| Vitamin B3 | Zinc | Spearmint Oil |
| Vitamin B3 | Magnesium | Selenium |
| Vitamin B3 | Magnesium | *Echinacea* |
| Vitamin B3 | Magnesium | Olive leaf (*olea europaea*) |
| Vitamin B3 | Magnesium | Wild indigo (*baptisia tinctoria*) |
| Vitamin B3 | Magnesium | Goldenseal (*hydrastis canadensis*) |
| Vitamin B3 | Magnesium | Fenugreek |
| Vitamin B3 | Magnesium | Mullein |
| Vitamin B3 | Magnesium | Phenol |
| Vitamin B3 | Magnesium | Camphor |
| Vitamin B3 | Magnesium | Pectin |
| Vitamin B3 | Magnesium | *Eucalyptus* Oil |
| Vitamin B3 | Magnesium | Peppermint Oil |
| Vitamin B3 | Magnesium | Spearmint Oil |
| Vitamin B3 | Selenium | *Echinacea* |
| Vitamin B3 | Selenium | Olive leaf (*olea europaea*) |
| Vitamin B3 | Selenium | Wild indigo (*baptisia tinctoria*) |
| Vitamin B3 | Selenium | Goldenseal (*hydrastis canadensis*) |
| Vitamin B3 | Selenium | Fenugreek |
| Vitamin B3 | Selenium | Mullein |
| Vitamin B3 | Selenium | Phenol |
| Vitamin B3 | Selenium | Camphor |
| Vitamin B3 | Selenium | Pectin |
| Vitamin B3 | Selenium | *Eucalyptus* Oil |
| Vitamin B3 | Selenium | Peppermint Oil |
| Vitamin B3 | Selenium | Spearmint Oil |
| Vitamin B3 | *Echinacea* | Olive leaf (*olea europaea*) |

TABLE 3-continued

Three Ingredient Combinations

| First Ingredient | Second Ingredient | Third Ingredient |
|---|---|---|
| Vitamin B3 | *Echinacea* | Wild indigo (*baptisia tinctoria*) |
| Vitamin B3 | *Echinacea* | Goldenseal (*hydrastis canadensis*) |
| Vitamin B3 | *Echinacea* | Fenugreek |
| Vitamin B3 | *Echinacea* | Mullein |
| Vitamin B3 | *Echinacea* | Phenol |
| Vitamin B3 | *Echinacea* | Camphor |
| Vitamin B3 | *Echinacea* | Pectin |
| Vitamin B3 | *Echinacea* | *Eucalyptus* Oil |
| Vitamin B3 | *Echinacea* | Peppermint Oil |
| Vitamin B3 | *Echinacea* | Spearmint Oil |
| Vitamin B3 | Olive leaf (*olea europaea*) | Wild indigo (*baptisia tinctoria*) |
| Vitamin B3 | Olive leaf (*olea europaea*) | Goldenseal (*hydrastis canadensis*) |
| Vitamin B3 | Olive leaf (*olea europaea*) | Fenugreek |
| Vitamin B3 | Olive leaf (*olea europaea*) | Mullein |
| Vitamin B3 | Olive leaf (*olea europaea*) | Phenol |
| Vitamin B3 | Olive leaf (*olea europaea*) | Camphor |
| Vitamin B3 | Olive leaf (*olea europaea*) | Pectin |
| Vitamin B3 | Olive leaf (*olea europaea*) | *Eucalyptus* Oil |
| Vitamin B3 | Olive leaf (*olea europaea*) | Peppermint Oil |
| Vitamin B3 | Olive leaf (*olea europaea*) | Spearmint Oil |
| Vitamin B3 | Wild indigo (*baptisia tinctoria*) | Goldenseal (*hydrastis canadensis*) |
| Vitamin B3 | Wild indigo (*baptisia tinctoria*) | Fenugreek |
| Vitamin B3 | Wild indigo (*baptisia tinctoria*) | Mullein |
| Vitamin B3 | Wild indigo (*baptisia tinctoria*) | Phenol |
| Vitamin B3 | Wild indigo (*baptisia tinctoria*) | Camphor |
| Vitamin B3 | Wild indigo (*baptisia tinctoria*) | Pectin |
| Vitamin B3 | Wild indigo (*baptisia tinctoria*) | *Eucalyptus* Oil |
| Vitamin B3 | Wild indigo (*baptisia tinctoria*) | Peppermint Oil |
| Vitamin B3 | Wild indigo (*baptisia tinctoria*) | Spearmint Oil |
| Vitamin B3 | Goldenseal (*hydrastis canadensis*) | Fenugreek |
| Vitamin B3 | Goldenseal (*hydrastis canadensis*) | Mullein |
| Vitamin B3 | Goldenseal (*hydrastis canadensis*) | Phenol |
| Vitamin B3 | Goldenseal (*hydrastis canadensis*) | Camphor |
| Vitamin B3 | Goldenseal (*hydrastis canadensis*) | Pectin |
| Vitamin B3 | Goldenseal (*hydrastis canadensis*) | *Eucalyptus* Oil |
| Vitamin B3 | Goldenseal (*hydrastis canadensis*) | Peppermint Oil |
| Vitamin B3 | Goldenseal (*hydrastis canadensis*) | Spearmint Oil |
| Vitamin B3 | Fenugreek | Mullein |
| Vitamin B3 | Fenugreek | Phenol |
| Vitamin B3 | Fenugreek | Camphor |
| Vitamin B3 | Fenugreek | Pectin |
| Vitamin B3 | Fenugreek | *Eucalyptus* Oil |
| Vitamin B3 | Fenugreek | Peppermint Oil |
| Vitamin B3 | Fenugreek | Spearmint Oil |
| Vitamin B3 | Mullein | Phenol |
| Vitamin B3 | Mullein | Camphor |
| Vitamin B3 | Mullein | Pectin |
| Vitamin B3 | Mullein | *Eucalyptus* Oil |
| Vitamin B3 | Mullein | Peppermint Oil |
| Vitamin B3 | Mullein | Spearmint Oil |
| Vitamin B3 | Phenol | Camphor |
| Vitamin B3 | Phenol | Pectin |
| Vitamin B3 | Phenol | *Eucalyptus* Oil |
| Vitamin B3 | Phenol | Peppermint Oil |
| Vitamin B3 | Phenol | Spearmint Oil |
| Vitamin B3 | Camphor | Pectin |
| Vitamin B3 | Camphor | *Eucalyptus* Oil |
| Vitamin B3 | Camphor | Peppermint Oil |
| Vitamin B3 | Camphor | Spearmint Oil |
| Vitamin B3 | Pectin | *Eucalyptus* Oil |
| Vitamin B3 | Pectin | Peppermint Oil |
| Vitamin B3 | Pectin | Spearmint Oil |
| Vitamin B3 | *Eucalyptus* Oil | Peppermint Oil |
| Vitamin B3 | *Eucalyptus* Oil | Spearmint Oil |
| Vitamin B3 | Peppermint Oil | Spearmint Oil |
| Vitamin B5 | Vitamin B6 | Vitamin B7 |
| Vitamin B5 | Vitamin B6 | Vitamin B8 |
| Vitamin B5 | Vitamin B6 | Vitamin B9 |
| Vitamin B5 | Vitamin B6 | Vitamin B12 |
| Vitamin B5 | Vitamin B6 | Vitamin C |
| Vitamin B5 | Vitamin B6 | Vitamin E |
| Vitamin B5 | Vitamin B6 | Zinc |
| Vitamin B5 | Vitamin B6 | Magnesium |
| Vitamin B5 | Vitamin B6 | Selenium |
| Vitamin B5 | Vitamin B6 | *Echinacea* |
| Vitamin B5 | Vitamin B6 | Olive leaf (*olea europaea*) |

TABLE 3-continued

Three Ingredient Combinations

| First Ingredient | Second Ingredient | Third Ingredient |
| --- | --- | --- |
| Vitamin B5 | Vitamin B6 | Wild indigo (*baptisia tinctoria*) |
| Vitamin B5 | Vitamin B6 | Goldenseal (*hydrastis canadensis*) |
| Vitamin B5 | Vitamin B6 | Fenugreek |
| Vitamin B5 | Vitamin B6 | Mullein |
| Vitamin B5 | Vitamin B6 | Phenol |
| Vitamin B5 | Vitamin B6 | Camphor |
| Vitamin B5 | Vitamin B6 | Pectin |
| Vitamin B5 | Vitamin B6 | *Eucalyptus* Oil |
| Vitamin B5 | Vitamin B6 | Peppermint Oil |
| Vitamin B5 | Vitamin B6 | Spearmint Oil |
| Vitamin B5 | Vitamin B7 | Vitamin B8 |
| Vitamin B5 | Vitamin B7 | Vitamin B9 |
| Vitamin B5 | Vitamin B7 | Vitamin B12 |
| Vitamin B5 | Vitamin B7 | Vitamin C |
| Vitamin B5 | Vitamin B7 | Vitamin E |
| Vitamin B5 | Vitamin B7 | Zinc |
| Vitamin B5 | Vitamin B7 | Magnesium |
| Vitamin B5 | Vitamin B7 | Selenium |
| Vitamin B5 | Vitamin B7 | Echinacea |
| Vitamin B5 | Vitamin B7 | Olive leaf (*olea europaea*) |
| Vitamin B5 | Vitamin B7 | Wild indigo (*baptisia tinctoria*) |
| Vitamin B5 | Vitamin B7 | Goldenseal (*hydrastis canadensis*) |
| Vitamin B5 | Vitamin B7 | Fenugreek |
| Vitamin B5 | Vitamin B7 | Mullein |
| Vitamin B5 | Vitamin B7 | Phenol |
| Vitamin B5 | Vitamin B7 | Camphor |
| Vitamin B5 | Vitamin B7 | Pectin |
| Vitamin B5 | Vitamin B7 | *Eucalyptus* Oil |
| Vitamin B5 | Vitamin B7 | Peppermint Oil |
| Vitamin B5 | Vitamin B7 | Spearmint Oil |
| Vitamin B5 | Vitamin B8 | Vitamin B9 |
| Vitamin B5 | Vitamin B8 | Vitamin B12 |
| Vitamin B5 | Vitamin B8 | Vitamin C |
| Vitamin B5 | Vitamin B8 | Vitamin E |
| Vitamin B5 | Vitamin B8 | Zinc |
| Vitamin B5 | Vitamin B8 | Magnesium |
| Vitamin B5 | Vitamin B8 | Selenium |
| Vitamin B5 | Vitamin B8 | Echinacea |
| Vitamin B5 | Vitamin B8 | Olive leaf (*olea europaea*) |
| Vitamin B5 | Vitamin B8 | Wild indigo (*baptisia tinctoria*) |
| Vitamin B5 | Vitamin B8 | Goldenseal (*hydrastis canadensis*) |
| Vitamin B5 | Vitamin B8 | Fenugreek |
| Vitamin B5 | Vitamin B8 | Mullein |
| Vitamin B5 | Vitamin B8 | Phenol |
| Vitamin B5 | Vitamin B8 | Camphor |
| Vitamin B5 | Vitamin B8 | Pectin |
| Vitamin B5 | Vitamin B8 | *Eucalyptus* Oil |
| Vitamin B5 | Vitamin B8 | Peppermint Oil |
| Vitamin B5 | Vitamin B8 | Spearmint Oil |
| Vitamin B5 | Vitamin B9 | Vitamin B12 |
| Vitamin B5 | Vitamin B9 | Vitamin C |
| Vitamin B5 | Vitamin B9 | Vitamin E |
| Vitamin B5 | Vitamin B9 | Zinc |
| Vitamin B5 | Vitamin B9 | Magnesium |
| Vitamin B5 | Vitamin B9 | Selenium |
| Vitamin B5 | Vitamin B9 | Echinacea |
| Vitamin B5 | Vitamin B9 | Olive leaf (*olea europaea*) |
| Vitamin B5 | Vitamin B9 | Wild indigo (*baptisia tinctoria*) |
| Vitamin B5 | Vitamin B9 | Goldenseal (*hydrastis canadensis*) |
| Vitamin B5 | Vitamin B9 | Fenugreek |
| Vitamin B5 | Vitamin B9 | Mullein |
| Vitamin B5 | Vitamin B9 | Phenol |
| Vitamin B5 | Vitamin B9 | Camphor |
| Vitamin B5 | Vitamin B9 | Pectin |
| Vitamin B5 | Vitamin B9 | *Eucalyptus* Oil |
| Vitamin B5 | Vitamin B9 | Peppermint Oil |
| Vitamin B5 | Vitamin B9 | Spearmint Oil |
| Vitamin B5 | Vitamin B12 | Vitamin C |
| Vitamin B5 | Vitamin B12 | Vitamin E |
| Vitamin B5 | Vitamin B12 | Zinc |
| Vitamin B5 | Vitamin B12 | Magnesium |
| Vitamin B5 | Vitamin B12 | Selenium |
| Vitamin B5 | Vitamin B12 | Echinacea |
| Vitamin B5 | Vitamin B12 | Olive leaf (*olea europaea*) |
| Vitamin B5 | Vitamin B12 | Wild indigo (*baptisia tinctoria*) |
| Vitamin B5 | Vitamin B12 | Goldenseal (*hydrastis canadensis*) |

TABLE 3-continued

Three Ingredient Combinations

| First Ingredient | Second Ingredient | Third Ingredient |
| --- | --- | --- |
| Vitamin B5 | Vitamin B12 | Fenugreek |
| Vitamin B5 | Vitamin B12 | Mullein |
| Vitamin B5 | Vitamin B12 | Phenol |
| Vitamin B5 | Vitamin B12 | Camphor |
| Vitamin B5 | Vitamin B12 | Pectin |
| Vitamin B5 | Vitamin B12 | *Eucalyptus* Oil |
| Vitamin B5 | Vitamin B12 | Peppermint Oil |
| Vitamin B5 | Vitamin B12 | Spearmint Oil |
| Vitamin B5 | Vitamin C | Vitamin E |
| Vitamin B5 | Vitamin C | Zinc |
| Vitamin B5 | Vitamin C | Magnesium |
| Vitamin B5 | Vitamin C | Selenium |
| Vitamin B5 | Vitamin C | *Echinacea* |
| Vitamin B5 | Vitamin C | Olive leaf (*olea europaea*) |
| Vitamin B5 | Vitamin C | Wild indigo (*baptisia tinctoria*) |
| Vitamin B5 | Vitamin C | Goldenseal (*hydrastis canadensis*) |
| Vitamin B5 | Vitamin C | Fenugreek |
| Vitamin B5 | Vitamin C | Mullein |
| Vitamin B5 | Vitamin C | Phenol |
| Vitamin B5 | Vitamin C | Camphor |
| Vitamin B5 | Vitamin C | Pectin |
| Vitamin B5 | Vitamin C | *Eucalyptus* Oil |
| Vitamin B5 | Vitamin C | Peppermint Oil |
| Vitamin B5 | Vitamin C | Spearmint Oil |
| Vitamin B5 | Vitamin E | Zinc |
| Vitamin B5 | Vitamin E | Magnesium |
| Vitamin B5 | Vitamin E | Selenium |
| Vitamin B5 | Vitamin E | *Echinacea* |
| Vitamin B5 | Vitamin E | Olive leaf (*olea europaea*) |
| Vitamin B5 | Vitamin E | Wild indigo (*baptisia tinctoria*) |
| Vitamin B5 | Vitamin E | Goldenseal (*hydrastis canadensis*) |
| Vitamin B5 | Vitamin E | Fenugreek |
| Vitamin B5 | Vitamin E | Mullein |
| Vitamin B5 | Vitamin E | Phenol |
| Vitamin B5 | Vitamin E | Camphor |
| Vitamin B5 | Vitamin E | Pectin |
| Vitamin B5 | Vitamin E | *Eucalyptus* Oil |
| Vitamin B5 | Vitamin E | Peppermint Oil |
| Vitamin B5 | Vitamin E | Spearmint Oil |
| Vitamin B5 | Zinc | Magnesium |
| Vitamin B5 | Zinc | Selenium |
| Vitamin B5 | Zinc | *Echinacea* |
| Vitamin B5 | Zinc | Olive leaf (*olea europaea*) |
| Vitamin B5 | Zinc | Wild indigo (*baptisia tinctoria*) |
| Vitamin B5 | Zinc | Goldenseal (*hydrastis canadensis*) |
| Vitamin B5 | Zinc | Fenugreek |
| Vitamin B5 | Zinc | Mullein |
| Vitamin B5 | Zinc | Phenol |
| Vitamin B5 | Zinc | Camphor |
| Vitamin B5 | Zinc | Pectin |
| Vitamin B5 | Zinc | *Eucalyptus* Oil |
| Vitamin B5 | Zinc | Peppermint Oil |
| Vitamin B5 | Zinc | Spearmint Oil |
| Vitamin B5 | Magnesium | Selenium |
| Vitamin B5 | Magnesium | *Echinacea* |
| Vitamin B5 | Magnesium | Olive leaf (*olea europaea*) |
| Vitamin B5 | Magnesium | Wild indigo (*baptisia tinctoria*) |
| Vitamin B5 | Magnesium | Goldenseal (*hydrastis canadensis*) |
| Vitamin B5 | Magnesium | Fenugreek |
| Vitamin B5 | Magnesium | Mullein |
| Vitamin B5 | Magnesium | Phenol |
| Vitamin B5 | Magnesium | Camphor |
| Vitamin B5 | Magnesium | Pectin |
| Vitamin B5 | Magnesium | *Eucalyptus* Oil |
| Vitamin B5 | Magnesium | Peppermint Oil |
| Vitamin B5 | Magnesium | Spearmint Oil |
| Vitamin B5 | Selenium | *Echinacea* |
| Vitamin B5 | Selenium | Olive leaf (*olea europaea*) |
| Vitamin B5 | Selenium | Wild indigo (*baptisia tinctoria*) |
| Vitamin B5 | Selenium | Goldenseal (*hydrastis canadensis*) |
| Vitamin B5 | Selenium | Fenugreek |
| Vitamin B5 | Selenium | Mullein |
| Vitamin B5 | Selenium | Phenol |
| Vitamin B5 | Selenium | Camphor |
| Vitamin B5 | Selenium | Pectin |
| Vitamin B5 | Selenium | *Eucalyptus* Oil |

TABLE 3-continued

| Three Ingredient Combinations | | |
| --- | --- | --- |
| First Ingredient | Second Ingredient | Third Ingredient |
| Vitamin B5 | Selenium | Peppermint Oil |
| Vitamin B5 | Selenium | Spearmint Oil |
| Vitamin B5 | *Echinacea* | Olive leaf (*olea europaea*) |
| Vitamin B5 | *Echinacea* | Wild indigo (*baptisia tinctoria*) |
| Vitamin B5 | *Echinacea* | Goldenseal (*hydrastis canadensis*) |
| Vitamin B5 | *Echinacea* | Fenugreek |
| Vitamin B5 | *Echinacea* | Mullein |
| Vitamin B5 | *Echinacea* | Phenol |
| Vitamin B5 | *Echinacea* | Camphor |
| Vitamin B5 | *Echinacea* | Pectin |
| Vitamin B5 | *Echinacea* | *Eucalyptus* Oil |
| Vitamin B5 | *Echinacea* | Peppermint Oil |
| Vitamin B5 | *Echinacea* | Spearmint Oil |
| Vitamin B5 | Olive leaf (*olea europaea*) | Wild indigo (*baptisia tinctoria*) |
| Vitamin B5 | Olive leaf (*olea europaea*) | Goldenseal (*hydrastis canadensis*) |
| Vitamin B5 | Olive leaf (*olea europaea*) | Fenugreek |
| Vitamin B5 | Olive leaf (*olea europaea*) | Mullein |
| Vitamin B5 | Olive leaf (*olea europaea*) | Phenol |
| Vitamin B5 | Olive leaf (*olea europaea*) | Camphor |
| Vitamin B5 | Olive leaf (*olea europaea*) | Pectin |
| Vitamin B5 | Olive leaf (*olea europaea*) | *Eucalyptus* Oil |
| Vitamin B5 | Olive leaf (*olea europaea*) | Peppermint Oil |
| Vitamin B5 | Olive leaf (*olea europaea*) | Spearmint Oil |
| Vitamin B5 | Wild indigo (*baptisia tinctoria*) | Goldenseal (*hydrastis canadensis*) |
| Vitamin B5 | Wild indigo (*baptisia tinctoria*) | Fenugreek |
| Vitamin B5 | Wild indigo (*baptisia tinctoria*) | Mullein |
| Vitamin B5 | Wild indigo (*baptisia tinctoria*) | Phenol |
| Vitamin B5 | Wild indigo (*baptisia tinctoria*) | Camphor |
| Vitamin B5 | Wild indigo (*baptisia tinctoria*) | Pectin |
| Vitamin B5 | Wild indigo (*baptisia tinctoria*) | *Eucalyptus* Oil |
| Vitamin B5 | Wild indigo (*baptisia tinctoria*) | Peppermint Oil |
| Vitamin B5 | Wild indigo (*baptisia tinctoria*) | Spearmint Oil |
| Vitamin B5 | Goldenseal (*hydrastis canadensis*) | Fenugreek |
| Vitamin B5 | Goldenseal (*hydrastis canadensis*) | Mullein |
| Vitamin B5 | Goldenseal (*hydrastis canadensis*) | Phenol |
| Vitamin B5 | Goldenseal (*hydrastis canadensis*) | Camphor |
| Vitamin B5 | Goldenseal (*hydrastis canadensis*) | Pectin |
| Vitamin B5 | Goldenseal (*hydrastis canadensis*) | *Eucalyptus* Oil |
| Vitamin B5 | Goldenseal (*hydrastis canadensis*) | Peppermint Oil |
| Vitamin B5 | Goldenseal (*hydrastis canadensis*) | Spearmint Oil |
| Vitamin B5 | Fenugreek | Mullein |
| Vitamin B5 | Fenugreek | Phenol |
| Vitamin B5 | Fenugreek | Camphor |
| Vitamin B5 | Fenugreek | Pectin |
| Vitamin B5 | Fenugreek | *Eucalyptus* Oil |
| Vitamin B5 | Fenugreek | Peppermint Oil |
| Vitamin B5 | Fenugreek | Spearmint Oil |
| Vitamin B5 | Mullein | Phenol |
| Vitamin B5 | Mullein | Camphor |
| Vitamin B5 | Mullein | Pectin |
| Vitamin B5 | Mullein | *Eucalyptus* Oil |
| Vitamin B5 | Mullein | Peppermint Oil |
| Vitamin B5 | Mullein | Spearmint Oil |
| Vitamin B5 | Phenol | Camphor |
| Vitamin B5 | Phenol | Pectin |
| Vitamin B5 | Phenol | *Eucalyptus* Oil |
| Vitamin B5 | Phenol | Peppermint Oil |
| Vitamin B5 | Phenol | Spearmint Oil |
| Vitamin B5 | Camphor | Pectin |
| Vitamin B5 | Camphor | *Eucalyptus* Oil |
| Vitamin B5 | Camphor | Peppermint Oil |
| Vitamin B5 | Camphor | Spearmint Oil |
| Vitamin B5 | Pectin | *Eucalyptus* Oil |
| Vitamin B5 | Pectin | Peppermint Oil |
| Vitamin B5 | Pectin | Spearmint Oil |
| Vitamin B5 | *Eucalyptus* Oil | Peppermint Oil |
| Vitamin B5 | *Eucalyptus* Oil | Spearmint Oil |
| Vitamin B5 | Peppermint Oil | Spearmint Oil |
| Vitamin B6 | Vitamin B7 | Vitamin B8 |
| Vitamin B6 | Vitamin B7 | Vitamin B9 |
| Vitamin B6 | Vitamin B7 | Vitamin B12 |
| Vitamin B6 | Vitamin B7 | Vitamin C |
| Vitamin B6 | Vitamin B7 | Vitamin E |
| Vitamin B6 | Vitamin B7 | Zinc |
| Vitamin B6 | Vitamin B7 | Magnesium |
| Vitamin B6 | Vitamin B7 | Selenium |

TABLE 3-continued

Three Ingredient Combinations

| First Ingredient | Second Ingredient | Third Ingredient |
| --- | --- | --- |
| Vitamin B6 | Vitamin B7 | Echinacea |
| Vitamin B6 | Vitamin B7 | Olive leaf (olea europaea) |
| Vitamin B6 | Vitamin B7 | Wild indigo (baptisia tinctoria) |
| Vitamin B6 | Vitamin B7 | Goldenseal (hydrastis canadensis) |
| Vitamin B6 | Vitamin B7 | Fenugreek |
| Vitamin B6 | Vitamin B7 | Mullein |
| Vitamin B6 | Vitamin B7 | Phenol |
| Vitamin B6 | Vitamin B7 | Camphor |
| Vitamin B6 | Vitamin B7 | Pectin |
| Vitamin B6 | Vitamin B7 | Eucalyptus Oil |
| Vitamin B6 | Vitamin B7 | Peppermint Oil |
| Vitamin B6 | Vitamin B7 | Spearmint Oil |
| Vitamin B6 | Vitamin B8 | Vitamin B9 |
| Vitamin B6 | Vitamin B8 | Vitamin B12 |
| Vitamin B6 | Vitamin B8 | Vitamin C |
| Vitamin B6 | Vitamin B8 | Vitamin E |
| Vitamin B6 | Vitamin B8 | Zinc |
| Vitamin B6 | Vitamin B8 | Magnesium |
| Vitamin B6 | Vitamin B8 | Selenium |
| Vitamin B6 | Vitamin B8 | Echinacea |
| Vitamin B6 | Vitamin B8 | Olive leaf (olea europaea) |
| Vitamin B6 | Vitamin B8 | Wild indigo (baptisia tinctoria) |
| Vitamin B6 | Vitamin B8 | Goldenseal (hydrastis canadensis) |
| Vitamin B6 | Vitamin B8 | Fenugreek |
| Vitamin B6 | Vitamin B8 | Mullein |
| Vitamin B6 | Vitamin B8 | Phenol |
| Vitamin B6 | Vitamin B8 | Camphor |
| Vitamin B6 | Vitamin B8 | Pectin |
| Vitamin B6 | Vitamin B8 | Eucalyptus Oil |
| Vitamin B6 | Vitamin B8 | Peppermint Oil |
| Vitamin B6 | Vitamin B8 | Spearmint Oil |
| Vitamin B6 | Vitamin B9 | Vitamin B12 |
| Vitamin B6 | Vitamin B9 | Vitamin C |
| Vitamin B6 | Vitamin B9 | Vitamin E |
| Vitamin B6 | Vitamin B9 | Zinc |
| Vitamin B6 | Vitamin B9 | Magnesium |
| Vitamin B6 | Vitamin B9 | Selenium |
| Vitamin B6 | Vitamin B9 | Echinacea |
| Vitamin B6 | Vitamin B9 | Olive leaf (olea europaea) |
| Vitamin B6 | Vitamin B9 | Wild indigo (baptisia tinctoria) |
| Vitamin B6 | Vitamin B9 | Goldenseal (hydrastis canadensis) |
| Vitamin B6 | Vitamin B9 | Fenugreek |
| Vitamin B6 | Vitamin B9 | Mullein |
| Vitamin B6 | Vitamin B9 | Phenol |
| Vitamin B6 | Vitamin B9 | Camphor |
| Vitamin B6 | Vitamin B9 | Pectin |
| Vitamin B6 | Vitamin B9 | Eucalyptus Oil |
| Vitamin B6 | Vitamin B9 | Peppermint Oil |
| Vitamin B6 | Vitamin B9 | Spearmint Oil |
| Vitamin B6 | Vitamin B12 | Vitamin C |
| Vitamin B6 | Vitamin B12 | Vitamin E |
| Vitamin B6 | Vitamin B12 | Zinc |
| Vitamin B6 | Vitamin B12 | Magnesium |
| Vitamin B6 | Vitamin B12 | Selenium |
| Vitamin B6 | Vitamin B12 | Echinacea |
| Vitamin B6 | Vitamin B12 | Olive leaf (olea europaea) |
| Vitamin B6 | Vitamin B12 | Wild indigo (baptisia tinctoria) |
| Vitamin B6 | Vitamin B12 | Goldenseal (hydrastis canadensis) |
| Vitamin B6 | Vitamin B12 | Fenugreek |
| Vitamin B6 | Vitamin B12 | Mullein |
| Vitamin B6 | Vitamin B12 | Phenol |
| Vitamin B6 | Vitamin B12 | Camphor |
| Vitamin B6 | Vitamin B12 | Pectin |
| Vitamin B6 | Vitamin B12 | Eucalyptus Oil |
| Vitamin B6 | Vitamin B12 | Peppermint Oil |
| Vitamin B6 | Vitamin B12 | Spearmint Oil |
| Vitamin B6 | Vitamin C | Vitamin E |
| Vitamin B6 | Vitamin C | Zinc |
| Vitamin B6 | Vitamin C | Magnesium |
| Vitamin B6 | Vitamin C | Selenium |
| Vitamin B6 | Vitamin C | Echinacea |
| Vitamin B6 | Vitamin C | Olive leaf (olea europaea) |
| Vitamin B6 | Vitamin C | Wild indigo (baptisia tinctoria) |
| Vitamin B6 | Vitamin C | Goldenseal (hydrastis canadensis) |
| Vitamin B6 | Vitamin C | Fenugreek |
| Vitamin B6 | Vitamin C | Mullein |

TABLE 3-continued

Three Ingredient Combinations

| First Ingredient | Second Ingredient | Third Ingredient |
| --- | --- | --- |
| Vitamin B6 | Vitamin C | Phenol |
| Vitamin B6 | Vitamin C | Camphor |
| Vitamin B6 | Vitamin C | Pectin |
| Vitamin B6 | Vitamin C | *Eucalyptus* Oil |
| Vitamin B6 | Vitamin C | Peppermint Oil |
| Vitamin B6 | Vitamin C | Spearmint Oil |
| Vitamin B6 | Vitamin E | Zinc |
| Vitamin B6 | Vitamin E | Magnesium |
| Vitamin B6 | Vitamin E | Selenium |
| Vitamin B6 | Vitamin E | *Echinacea* |
| Vitamin B6 | Vitamin E | Olive leaf (*olea europaea*) |
| Vitamin B6 | Vitamin E | Wild indigo (*baptisia tinctoria*) |
| Vitamin B6 | Vitamin E | Goldenseal (*hydrastis canadensis*) |
| Vitamin B6 | Vitamin E | Fenugreek |
| Vitamin B6 | Vitamin E | Mullein |
| Vitamin B6 | Vitamin E | Phenol |
| Vitamin B6 | Vitamin E | Camphor |
| Vitamin B6 | Vitamin E | Pectin |
| Vitamin B6 | Vitamin E | *Eucalyptus* Oil |
| Vitamin B6 | Vitamin E | Peppermint Oil |
| Vitamin B6 | Vitamin E | Spearmint Oil |
| Vitamin B6 | Zinc | Magnesium |
| Vitamin B6 | Zinc | Selenium |
| Vitamin B6 | Zinc | *Echinacea* |
| Vitamin B6 | Zinc | Olive leaf (*olea europaea*) |
| Vitamin B6 | Zinc | Wild indigo (*baptisia tinctoria*) |
| Vitamin B6 | Zinc | Goldenseal (*hydrastis canadensis*) |
| Vitamin B6 | Zinc | Fenugreek |
| Vitamin B6 | Zinc | Mullein |
| Vitamin B6 | Zinc | Phenol |
| Vitamin B6 | Zinc | Camphor |
| Vitamin B6 | Zinc | Pectin |
| Vitamin B6 | Zinc | *Eucalyptus* Oil |
| Vitamin B6 | Zinc | Peppermint Oil |
| Vitamin B6 | Zinc | Spearmint Oil |
| Vitamin B6 | Magnesium | Selenium |
| Vitamin B6 | Magnesium | *Echinacea* |
| Vitamin B6 | Magnesium | Olive leaf (*olea europaea*) |
| Vitamin B6 | Magnesium | Wild indigo (*baptisia tinctoria*) |
| Vitamin B6 | Magnesium | Goldenseal (*hydrastis canadensis*) |
| Vitamin B6 | Magnesium | Fenugreek |
| Vitamin B6 | Magnesium | Mullein |
| Vitamin B6 | Magnesium | Phenol |
| Vitamin B6 | Magnesium | Camphor |
| Vitamin B6 | Magnesium | Pectin |
| Vitamin B6 | Magnesium | *Eucalyptus* Oil |
| Vitamin B6 | Magnesium | Peppermint Oil |
| Vitamin B6 | Magnesium | Spearmint Oil |
| Vitamin B6 | Selenium | *Echinacea* |
| Vitamin B6 | Selenium | Olive leaf (*olea europaea*) |
| Vitamin B6 | Selenium | Wild indigo (*baptisia tinctoria*) |
| Vitamin B6 | Selenium | Goldenseal (*hydrastis canadensis*) |
| Vitamin B6 | Selenium | Fenugreek |
| Vitamin B6 | Selenium | Mullein |
| Vitamin B6 | Selenium | Phenol |
| Vitamin B6 | Selenium | Camphor |
| Vitamin B6 | Selenium | Pectin |
| Vitamin B6 | Selenium | *Eucalyptus* Oil |
| Vitamin B6 | Selenium | Peppermint Oil |
| Vitamin B6 | Selenium | Spearmint Oil |
| Vitamin B6 | *Echinacea* | Olive leaf (*olea europaea*) |
| Vitamin B6 | *Echinacea* | Wild indigo (*baptisia tinctoria*) |
| Vitamin B6 | *Echinacea* | Goldenseal (*hydrastis canadensis*) |
| Vitamin B6 | *Echinacea* | Fenugreek |
| Vitamin B6 | *Echinacea* | Mullein |
| Vitamin B6 | *Echinacea* | Phenol |
| Vitamin B6 | *Echinacea* | Camphor |
| Vitamin B6 | *Echinacea* | Pectin |
| Vitamin B6 | *Echinacea* | *Eucalyptus* Oil |
| Vitamin B6 | *Echinacea* | Peppermint Oil |
| Vitamin B6 | *Echinacea* | Spearmint Oil |
| Vitamin B6 | Olive leaf (*olea europaea*) | Wild indigo (*baptisia tinctoria*) |
| Vitamin B6 | Olive leaf (*olea europaea*) | Goldenseal (*hydrastis canadensis*) |
| Vitamin B6 | Olive leaf (*olea europaea*) | Fenugreek |
| Vitamin B6 | Olive leaf (*olea europaea*) | Mullein |
| Vitamin B6 | Olive leaf (*olea europaea*) | Phenol |

TABLE 3-continued

| Three Ingredient Combinations | | |
|---|---|---|
| First Ingredient | Second Ingredient | Third Ingredient |
| Vitamin B6 | Olive leaf (*olea europaea*) | Camphor |
| Vitamin B6 | Olive leaf (*olea europaea*) | Pectin |
| Vitamin B6 | Olive leaf (*olea europaea*) | *Eucalyptus* Oil |
| Vitamin B6 | Olive leaf (*olea europaea*) | Peppermint Oil |
| Vitamin B6 | Olive leaf (*olea europaea*) | Spearmint Oil |
| Vitamin B6 | Wild indigo (*baptisia tinctoria*) | Goldenseal (*hydrastis canadensis*) |
| Vitamin B6 | Wild indigo (*baptisia tinctoria*) | Fenugreek |
| Vitamin B6 | Wild indigo (*baptisia tinctoria*) | Mullein |
| Vitamin B6 | Wild indigo (*baptisia tinctoria*) | Phenol |
| Vitamin B6 | Wild indigo (*baptisia tinctoria*) | Camphor |
| Vitamin B6 | Wild indigo (*baptisia tinctoria*) | Pectin |
| Vitamin B6 | Wild indigo (*baptisia tinctoria*) | *Eucalyptus* Oil |
| Vitamin B6 | Wild indigo (*baptisia tinctoria*) | Peppermint Oil |
| Vitamin B6 | Wild indigo (*baptisia tinctoria*) | Spearmint Oil |
| Vitamin B6 | Goldenseal (*hydrastis canadensis*) | Fenugreek |
| Vitamin B6 | Goldenseal (*hydrastis canadensis*) | Mullein |
| Vitamin B6 | Goldenseal (*hydrastis canadensis*) | Phenol |
| Vitamin B6 | Goldenseal (*hydrastis canadensis*) | Camphor |
| Vitamin B6 | Goldenseal (*hydrastis canadensis*) | Pectin |
| Vitamin B6 | Goldenseal (*hydrastis canadensis*) | *Eucalyptus* Oil |
| Vitamin B6 | Goldenseal (*hydrastis canadensis*) | Peppermint Oil |
| Vitamin B6 | Goldenseal (*hydrastis canadensis*) | Spearmint Oil |
| Vitamin B6 | Fenugreek | Mullein |
| Vitamin B6 | Fenugreek | Phenol |
| Vitamin B6 | Fenugreek | Camphor |
| Vitamin B6 | Fenugreek | Pectin |
| Vitamin B6 | Fenugreek | *Eucalyptus* Oil |
| Vitamin B6 | Fenugreek | Peppermint Oil |
| Vitamin B6 | Fenugreek | Spearmint Oil |
| Vitamin B6 | Mullein | Phenol |
| Vitamin B6 | Mullein | Camphor |
| Vitamin B6 | Mullein | Pectin |
| Vitamin B6 | Mullein | *Eucalyptus* Oil |
| Vitamin B6 | Mullein | Peppermint Oil |
| Vitamin B6 | Mullein | Spearmint Oil |
| Vitamin B6 | Phenol | Camphor |
| Vitamin B6 | Phenol | Pectin |
| Vitamin B6 | Phenol | *Eucalyptus* Oil |
| Vitamin B6 | Phenol | Peppermint Oil |
| Vitamin B6 | Phenol | Spearmint Oil |
| Vitamin B6 | Camphor | Pectin |
| Vitamin B6 | Camphor | *Eucalyptus* Oil |
| Vitamin B6 | Camphor | Peppermint Oil |
| Vitamin B6 | Camphor | Spearmint Oil |
| Vitamin B6 | Pectin | *Eucalyptus* Oil |
| Vitamin B6 | Pectin | Peppermint Oil |
| Vitamin B6 | Pectin | Spearmint Oil |
| Vitamin B6 | *Eucalyptus* Oil | Peppermint Oil |
| Vitamin B6 | *Eucalyptus* Oil | Spearmint Oil |
| Vitamin B6 | Peppermint Oil | Spearmint Oil |
| Vitamin B7 | Vitamin B8 | Vitamin B9 |
| Vitamin B7 | Vitamin B8 | Vitamin B12 |
| Vitamin B7 | Vitamin B8 | Vitamin C |
| Vitamin B7 | Vitamin B8 | Vitamin E |
| Vitamin B7 | Vitamin B8 | Zinc |
| Vitamin B7 | Vitamin B8 | Magnesium |
| Vitamin B7 | Vitamin B8 | Selenium |
| Vitamin B7 | Vitamin B8 | *Echinacea* |
| Vitamin B7 | Vitamin B8 | Olive leaf (*olea europaea*) |
| Vitamin B7 | Vitamin B8 | Wild indigo (*baptisia tinctoria*) |
| Vitamin B7 | Vitamin B8 | Goldenseal (*hydrastis canadensis*) |
| Vitamin B7 | Vitamin B8 | Fenugreek |
| Vitamin B7 | Vitamin B8 | Mullein |
| Vitamin B7 | Vitamin B8 | Phenol |
| Vitamin B7 | Vitamin B8 | Camphor |
| Vitamin B7 | Vitamin B8 | Pectin |
| Vitamin B7 | Vitamin B8 | *Eucalyptus* Oil |
| Vitamin B7 | Vitamin B8 | Peppermint Oil |
| Vitamin B7 | Vitamin B8 | Spearmint Oil |
| Vitamin B7 | Vitamin B9 | Vitamin B12 |
| Vitamin B7 | Vitamin B9 | Vitamin C |
| Vitamin B7 | Vitamin B9 | Vitamin E |
| Vitamin B7 | Vitamin B9 | Zinc |
| Vitamin B7 | Vitamin B9 | Magnesium |
| Vitamin B7 | Vitamin B9 | Selenium |
| Vitamin B7 | Vitamin B9 | *Echinacea* |

TABLE 3-continued

Three Ingredient Combinations

| First Ingredient | Second Ingredient | Third Ingredient |
| --- | --- | --- |
| Vitamin B7 | Vitamin B9 | Olive leaf (*olea europaea*) |
| Vitamin B7 | Vitamin B9 | Wild indigo (*baptisia tinctoria*) |
| Vitamin B7 | Vitamin B9 | Goldenseal (*hydrastis canadensis*) |
| Vitamin B7 | Vitamin B9 | Fenugreek |
| Vitamin B7 | Vitamin B9 | Mullein |
| Vitamin B7 | Vitamin B9 | Phenol |
| Vitamin B7 | Vitamin B9 | Camphor |
| Vitamin B7 | Vitamin B9 | Pectin |
| Vitamin B7 | Vitamin B9 | *Eucalyptus* Oil |
| Vitamin B7 | Vitamin B9 | Peppermint Oil |
| Vitamin B7 | Vitamin B9 | Spearmint Oil |
| Vitamin B7 | Vitamin B12 | Vitamin C |
| Vitamin B7 | Vitamin B12 | Vitamin E |
| Vitamin B7 | Vitamin B12 | Zinc |
| Vitamin B7 | Vitamin B12 | Magnesium |
| Vitamin B7 | Vitamin B12 | Selenium |
| Vitamin B7 | Vitamin B12 | *Echinacea* |
| Vitamin B7 | Vitamin B12 | Olive leaf (*olea europaea*) |
| Vitamin B7 | Vitamin B12 | Wild indigo (*baptisia tinctoria*) |
| Vitamin B7 | Vitamin B12 | Goldenseal (*hydrastis canadensis*) |
| Vitamin B7 | Vitamin B12 | Fenugreek |
| Vitamin B7 | Vitamin B12 | Mullein |
| Vitamin B7 | Vitamin B12 | Phenol |
| Vitamin B7 | Vitamin B12 | Camphor |
| Vitamin B7 | Vitamin B12 | Pectin |
| Vitamin B7 | Vitamin B12 | *Eucalyptus* Oil |
| Vitamin B7 | Vitamin B12 | Peppermint Oil |
| Vitamin B7 | Vitamin B12 | Spearmint Oil |
| Vitamin B7 | Vitamin C | Vitamin E |
| Vitamin B7 | Vitamin C | Zinc |
| Vitamin B7 | Vitamin C | Magnesium |
| Vitamin B7 | Vitamin C | Selenium |
| Vitamin B7 | Vitamin C | *Echinacea* |
| Vitamin B7 | Vitamin C | Olive leaf (*olea europaea*) |
| Vitamin B7 | Vitamin C | Wild indigo (*baptisia tinctoria*) |
| Vitamin B7 | Vitamin C | Goldenseal (*hydrastis canadensis*) |
| Vitamin B7 | Vitamin C | Fenugreek |
| Vitamin B7 | Vitamin C | Mullein |
| Vitamin B7 | Vitamin C | Phenol |
| Vitamin B7 | Vitamin C | Camphor |
| Vitamin B7 | Vitamin C | Pectin |
| Vitamin B7 | Vitamin C | *Eucalyptus* Oil |
| Vitamin B7 | Vitamin C | Peppermint Oil |
| Vitamin B7 | Vitamin C | Spearmint Oil |
| Vitamin B7 | Vitamin E | Zinc |
| Vitamin B7 | Vitamin E | Magnesium |
| Vitamin B7 | Vitamin E | Selenium |
| Vitamin B7 | Vitamin E | *Echinacea* |
| Vitamin B7 | Vitamin E | Olive leaf (*olea europaea*) |
| Vitamin B7 | Vitamin E | Wild indigo (*baptisia tinctoria*) |
| Vitamin B7 | Vitamin E | Goldenseal (*hydrastis canadensis*) |
| Vitamin B7 | Vitamin E | Fenugreek |
| Vitamin B7 | Vitamin E | Mullein |
| Vitamin B7 | Vitamin E | Phenol |
| Vitamin B7 | Vitamin E | Camphor |
| Vitamin B7 | Vitamin E | Pectin |
| Vitamin B7 | Vitamin E | *Eucalyptus* Oil |
| Vitamin B7 | Vitamin E | Peppermint Oil |
| Vitamin B7 | Vitamin E | Spearmint Oil |
| Vitamin B7 | Zinc | Magnesium |
| Vitamin B7 | Zinc | Selenium |
| Vitamin B7 | Zinc | *Echinacea* |
| Vitamin B7 | Zinc | Olive leaf (*olea europaea*) |
| Vitamin B7 | Zinc | Wild indigo (*baptisia tinctoria*) |
| Vitamin B7 | Zinc | Goldenseal (*hydrastis canadensis*) |
| Vitamin B7 | Zinc | Fenugreek |
| Vitamin B7 | Zinc | Mullein |
| Vitamin B7 | Zinc | Phenol |
| Vitamin B7 | Zinc | Camphor |
| Vitamin B7 | Zinc | Pectin |
| Vitamin B7 | Zinc | *Eucalyptus* Oil |
| Vitamin B7 | Zinc | Peppermint Oil |
| Vitamin B7 | Zinc | Spearmint Oil |
| Vitamin B7 | Magnesium | Selenium |
| Vitamin B7 | Magnesium | *Echinacea* |
| Vitamin B7 | Magnesium | Olive leaf (*olea europaea*) |

TABLE 3-continued

Three Ingredient Combinations

| First Ingredient | Second Ingredient | Third Ingredient |
|---|---|---|
| Vitamin B7 | Magnesium | Wild indigo (*baptisia tinctoria*) |
| Vitamin B7 | Magnesium | Goldenseal (*hydrastis canadensis*) |
| Vitamin B7 | Magnesium | Fenugreek |
| Vitamin B7 | Magnesium | Mullein |
| Vitamin B7 | Magnesium | Phenol |
| Vitamin B7 | Magnesium | Camphor |
| Vitamin B7 | Magnesium | Pectin |
| Vitamin B7 | Magnesium | *Eucalyptus* Oil |
| Vitamin B7 | Magnesium | Peppermint Oil |
| Vitamin B7 | Magnesium | Spearmint Oil |
| Vitamin B7 | Selenium | *Echinacea* |
| Vitamin B7 | Selenium | Olive leaf (*olea europaea*) |
| Vitamin B7 | Selenium | Wild indigo (*baptisia tinctoria*) |
| Vitamin B7 | Selenium | Goldenseal (*hydrastis canadensis*) |
| Vitamin B7 | Selenium | Fenugreek |
| Vitamin B7 | Selenium | Mullein |
| Vitamin B7 | Selenium | Phenol |
| Vitamin B7 | Selenium | Camphor |
| Vitamin B7 | Selenium | Pectin |
| Vitamin B7 | Selenium | *Eucalyptus* Oil |
| Vitamin B7 | Selenium | Peppermint Oil |
| Vitamin B7 | Selenium | Spearmint Oil |
| Vitamin B7 | *Echinacea* | Olive leaf (*olea europaea*) |
| Vitamin B7 | *Echinacea* | Wild indigo (*baptisia tinctoria*) |
| Vitamin B7 | *Echinacea* | Goldenseal (*hydrastis canadensis*) |
| Vitamin B7 | *Echinacea* | Fenugreek |
| Vitamin B7 | *Echinacea* | Mullein |
| Vitamin B7 | *Echinacea* | Phenol |
| Vitamin B7 | *Echinacea* | Camphor |
| Vitamin B7 | *Echinacea* | Pectin |
| Vitamin B7 | *Echinacea* | *Eucalyptus* Oil |
| Vitamin B7 | *Echinacea* | Peppermint Oil |
| Vitamin B7 | *Echinacea* | Spearmint Oil |
| Vitamin B7 | Olive leaf (*olea europaea*) | Wild indigo (*baptisia tinctoria*) |
| Vitamin B7 | Olive leaf (*olea europaea*) | Goldenseal (*hydrastis canadensis*) |
| Vitamin B7 | Olive leaf (*olea europaea*) | Fenugreek |
| Vitamin B7 | Olive leaf (*olea europaea*) | Mullein |
| Vitamin B7 | Olive leaf (*olea europaea*) | Phenol |
| Vitamin B7 | Olive leaf (*olea europaea*) | Camphor |
| Vitamin B7 | Olive leaf (*olea europaea*) | Pectin |
| Vitamin B7 | Olive leaf (*olea europaea*) | *Eucalyptus* Oil |
| Vitamin B7 | Olive leaf (*olea europaea*) | Peppermint Oil |
| Vitamin B7 | Olive leaf (*olea europaea*) | Spearmint Oil |
| Vitamin B7 | Wild indigo (*baptisia tinctoria*) | Goldenseal (*hydrastis canadensis*) |
| Vitamin B7 | Wild indigo (*baptisia tinctoria*) | Fenugreek |
| Vitamin B7 | Wild indigo (*baptisia tinctoria*) | Mullein |
| Vitamin B7 | Wild indigo (*baptisia tinctoria*) | Phenol |
| Vitamin B7 | Wild indigo (*baptisia tinctoria*) | Camphor |
| Vitamin B7 | Wild indigo (*baptisia tinctoria*) | Pectin |
| Vitamin B7 | Wild indigo (*baptisia tinctoria*) | *Eucalyptus* Oil |
| Vitamin B7 | Wild indigo (*baptisia tinctoria*) | Peppermint Oil |
| Vitamin B7 | Wild indigo (*baptisia tinctoria*) | Spearmint Oil |
| Vitamin B7 | Goldenseal (*hydrastis canadensis*) | Fenugreek |
| Vitamin B7 | Goldenseal (*hydrastis canadensis*) | Mullein |
| Vitamin B7 | Goldenseal (*hydrastis canadensis*) | Phenol |
| Vitamin B7 | Goldenseal (*hydrastis canadensis*) | Camphor |
| Vitamin B7 | Goldenseal (*hydrastis canadensis*) | Pectin |
| Vitamin B7 | Goldenseal (*hydrastis canadensis*) | *Eucalyptus* Oil |
| Vitamin B7 | Goldenseal (*hydrastis canadensis*) | Peppermint Oil |
| Vitamin B7 | Goldenseal (*hydrastis canadensis*) | Spearmint Oil |
| Vitamin B7 | Fenugreek | Mullein |
| Vitamin B7 | Fenugreek | Phenol |
| Vitamin B7 | Fenugreek | Camphor |
| Vitamin B7 | Fenugreek | Pectin |
| Vitamin B7 | Fenugreek | *Eucalyptus* Oil |
| Vitamin B7 | Fenugreek | Peppermint Oil |
| Vitamin B7 | Fenugreek | Spearmint Oil |
| Vitamin B7 | Mullein | Phenol |
| Vitamin B7 | Mullein | Camphor |
| Vitamin B7 | Mullein | Pectin |
| Vitamin B7 | Mullein | *Eucalyptus* Oil |
| Vitamin B7 | Mullein | Peppermint Oil |
| Vitamin B7 | Mullein | Spearmint Oil |
| Vitamin B7 | Phenol | Camphor |
| Vitamin B7 | Phenol | Pectin |
| Vitamin B7 | Phenol | *Eucalyptus* Oil |

TABLE 3-continued

| Three Ingredient Combinations | | |
|---|---|---|
| First Ingredient | Second Ingredient | Third Ingredient |
| Vitamin B7 | Phenol | Peppermint Oil |
| Vitamin B7 | Phenol | Spearmint Oil |
| Vitamin B7 | Camphor | Pectin |
| Vitamin B7 | Camphor | *Eucalyptus* Oil |
| Vitamin B7 | Camphor | Peppermint Oil |
| Vitamin B7 | Camphor | Spearmint Oil |
| Vitamin B7 | Pectin | *Eucalyptus* Oil |
| Vitamin B7 | Pectin | Peppermint Oil |
| Vitamin B7 | Pectin | Spearmint Oil |
| Vitamin B7 | *Eucalyptus* Oil | Peppermint Oil |
| Vitamin B7 | *Eucalyptus* Oil | Spearmint Oil |
| Vitamin B7 | Peppermint Oil | Spearmint Oil |
| Vitamin B8 | Vitamin B9 | Vitamin B12 |
| Vitamin B8 | Vitamin B9 | Vitamin C |
| Vitamin B8 | Vitamin B9 | Vitamin E |
| Vitamin B8 | Vitamin B9 | Zinc |
| Vitamin B8 | Vitamin B9 | Magnesium |
| Vitamin B8 | Vitamin B9 | Selenium |
| Vitamin B8 | Vitamin B9 | Echinacea |
| Vitamin B8 | Vitamin B9 | Olive leaf (*olea europaea*) |
| Vitamin B8 | Vitamin B9 | Wild indigo (*baptisia tinctoria*) |
| Vitamin B8 | Vitamin B9 | Goldenseal (*hydrastis canadensis*) |
| Vitamin B8 | Vitamin B9 | Fenugreek |
| Vitamin B8 | Vitamin B9 | Mullein |
| Vitamin B8 | Vitamin B9 | Phenol |
| Vitamin B8 | Vitamin B9 | Camphor |
| Vitamin B8 | Vitamin B9 | Pectin |
| Vitamin B8 | Vitamin B9 | *Eucalyptus* Oil |
| Vitamin B8 | Vitamin B9 | Peppermint Oil |
| Vitamin B8 | Vitamin B9 | Spearmint Oil |
| Vitamin B8 | Vitamin B12 | Vitamin C |
| Vitamin B8 | Vitamin B12 | Vitamin E |
| Vitamin B8 | Vitamin B12 | Zinc |
| Vitamin B8 | Vitamin B12 | Magnesium |
| Vitamin B8 | Vitamin B12 | Selenium |
| Vitamin B8 | Vitamin B12 | Echinacea |
| Vitamin B8 | Vitamin B12 | Olive leaf (*olea europaea*) |
| Vitamin B8 | Vitamin B12 | Wild indigo (*baptisia tinctoria*) |
| Vitamin B8 | Vitamin B12 | Goldenseal (*hydrastis canadensis*) |
| Vitamin B8 | Vitamin B12 | Fenugreek |
| Vitamin B8 | Vitamin B12 | Mullein |
| Vitamin B8 | Vitamin B12 | Phenol |
| Vitamin B8 | Vitamin B12 | Camphor |
| Vitamin B8 | Vitamin B12 | Pectin |
| Vitamin B8 | Vitamin B12 | *Eucalyptus* Oil |
| Vitamin B8 | Vitamin B12 | Peppermint Oil |
| Vitamin B8 | Vitamin B12 | Spearmint Oil |
| Vitamin B8 | Vitamin C | Vitamin E |
| Vitamin B8 | Vitamin C | Zinc |
| Vitamin B8 | Vitamin C | Magnesium |
| Vitamin B8 | Vitamin C | Selenium |
| Vitamin B8 | Vitamin C | Echinacea |
| Vitamin B8 | Vitamin C | Olive leaf (*olea europaea*) |
| Vitamin B8 | Vitamin C | Wild indigo (*baptisia tinctoria*) |
| Vitamin B8 | Vitamin C | Goldenseal (*hydrastis canadensis*) |
| Vitamin B8 | Vitamin C | Fenugreek |
| Vitamin B8 | Vitamin C | Mullein |
| Vitamin B8 | Vitamin C | Phenol |
| Vitamin B8 | Vitamin C | Camphor |
| Vitamin B8 | Vitamin C | Pectin |
| Vitamin B8 | Vitamin C | *Eucalyptus* Oil |
| Vitamin B8 | Vitamin C | Peppermint Oil |
| Vitamin B8 | Vitamin C | Spearmint Oil |
| Vitamin B8 | Vitamin E | Zinc |
| Vitamin B8 | Vitamin E | Magnesium |
| Vitamin B8 | Vitamin E | Selenium |
| Vitamin B8 | Vitamin E | Echinacea |
| Vitamin B8 | Vitamin E | Olive leaf (*olea europaea*) |
| Vitamin B8 | Vitamin E | Wild indigo (*baptisia tinctoria*) |
| Vitamin B8 | Vitamin E | Goldenseal (*hydrastis canadensis*) |
| Vitamin B8 | Vitamin E | Fenugreek |
| Vitamin B8 | Vitamin E | Mullein |
| Vitamin B8 | Vitamin E | Phenol |
| Vitamin B8 | Vitamin E | Camphor |
| Vitamin B8 | Vitamin E | Pectin |
| Vitamin B8 | Vitamin E | *Eucalyptus* Oil |

TABLE 3-continued

Three Ingredient Combinations

| First Ingredient | Second Ingredient | Third Ingredient |
| --- | --- | --- |
| Vitamin B8 | Vitamin E | Peppermint Oil |
| Vitamin B8 | Vitamin E | Spearmint Oil |
| Vitamin B8 | Zinc | Magnesium |
| Vitamin B8 | Zinc | Selenium |
| Vitamin B8 | Zinc | Echinacea |
| Vitamin B8 | Zinc | Olive leaf (olea europaea) |
| Vitamin B8 | Zinc | Wild indigo (baptisia tinctoria) |
| Vitamin B8 | Zinc | Goldenseal (hydrastis canadensis) |
| Vitamin B8 | Zinc | Fenugreek |
| Vitamin B8 | Zinc | Mullein |
| Vitamin B8 | Zinc | Phenol |
| Vitamin B8 | Zinc | Camphor |
| Vitamin B8 | Zinc | Pectin |
| Vitamin B8 | Zinc | Eucalyptus Oil |
| Vitamin B8 | Zinc | Peppermint Oil |
| Vitamin B8 | Zinc | Spearmint Oil |
| Vitamin B8 | Magnesium | Selenium |
| Vitamin B8 | Magnesium | Echinacea |
| Vitamin B8 | Magnesium | Olive leaf (olea europaea) |
| Vitamin B8 | Magnesium | Wild indigo (baptisia tinctoria) |
| Vitamin B8 | Magnesium | Goldenseal (hydrastis canadensis) |
| Vitamin B8 | Magnesium | Fenugreek |
| Vitamin B8 | Magnesium | Mullein |
| Vitamin B8 | Magnesium | Phenol |
| Vitamin B8 | Magnesium | Camphor |
| Vitamin B8 | Magnesium | Pectin |
| Vitamin B8 | Magnesium | Eucalyptus Oil |
| Vitamin B8 | Magnesium | Peppermint Oil |
| Vitamin B8 | Magnesium | Spearmint Oil |
| Vitamin B8 | Selenium | Echinacea |
| Vitamin B8 | Selenium | Olive leaf (olea europaea) |
| Vitamin B8 | Selenium | Wild indigo (baptisia tinctoria) |
| Vitamin B8 | Selenium | Goldenseal (hydrastis canadensis) |
| Vitamin B8 | Selenium | Fenugreek |
| Vitamin B8 | Selenium | Mullein |
| Vitamin B8 | Selenium | Phenol |
| Vitamin B8 | Selenium | Camphor |
| Vitamin B8 | Selenium | Pectin |
| Vitamin B8 | Selenium | Eucalyptus Oil |
| Vitamin B8 | Selenium | Peppermint Oil |
| Vitamin B8 | Selenium | Spearmint Oil |
| Vitamin B8 | Echinacea | Olive leaf (olea europaea) |
| Vitamin B8 | Echinacea | Wild indigo (baptisia tinctoria) |
| Vitamin B8 | Echinacea | Goldenseal (hydrastis canadensis) |
| Vitamin B8 | Echinacea | Fenugreek |
| Vitamin B8 | Echinacea | Mullein |
| Vitamin B8 | Echinacea | Phenol |
| Vitamin B8 | Echinacea | Camphor |
| Vitamin B8 | Echinacea | Pectin |
| Vitamin B8 | Echinacea | Eucalyptus Oil |
| Vitamin B8 | Echinacea | Peppermint Oil |
| Vitamin B8 | Echinacea | Spearmint Oil |
| Vitamin B8 | Olive leaf (olea europaea) | Wild indigo (baptisia tinctoria) |
| Vitamin B8 | Olive leaf (olea europaea) | Goldenseal (hydrastis canadensis) |
| Vitamin B8 | Olive leaf (olea europaea) | Fenugreek |
| Vitamin B8 | Olive leaf (olea europaea) | Mullein |
| Vitamin B8 | Olive leaf (olea europaea) | Phenol |
| Vitamin B8 | Olive leaf (olea europaea) | Camphor |
| Vitamin B8 | Olive leaf (olea europaea) | Pectin |
| Vitamin B8 | Olive leaf (olea europaea) | Eucalyptus Oil |
| Vitamin B8 | Olive leaf (olea europaea) | Peppermint Oil |
| Vitamin B8 | Olive leaf (olea europaea) | Spearmint Oil |
| Vitamin B8 | Wild indigo (baptisia tinctoria) | Goldenseal (hydrastis canadensis) |
| Vitamin B8 | Wild indigo (baptisia tinctoria) | Fenugreek |
| Vitamin B8 | Wild indigo (baptisia tinctoria) | Mullein |
| Vitamin B8 | Wild indigo (baptisia tinctoria) | Phenol |
| Vitamin B8 | Wild indigo (baptisia tinctoria) | Camphor |
| Vitamin B8 | Wild indigo (baptisia tinctoria) | Pectin |
| Vitamin B8 | Wild indigo (baptisia tinctoria) | Eucalyptus Oil |
| Vitamin B8 | Wild indigo (baptisia tinctoria) | Peppermint Oil |
| Vitamin B8 | Wild indigo (baptisia tinctoria) | Spearmint Oil |
| Vitamin B8 | Goldenseal (hydrastis canadensis) | Fenugreek |
| Vitamin B8 | Goldenseal (hydrastis canadensis) | Mullein |
| Vitamin B8 | Goldenseal (hydrastis canadensis) | Phenol |
| Vitamin B8 | Goldenseal (hydrastis canadensis) | Camphor |
| Vitamin B8 | Goldenseal (hydrastis canadensis) | Pectin |

TABLE 3-continued

| Three Ingredient Combinations | | |
|---|---|---|
| First Ingredient | Second Ingredient | Third Ingredient |
| Vitamin B8 | Goldenseal (*hydrastis canadensis*) | *Eucalyptus* Oil |
| Vitamin B8 | Goldenseal (*hydrastis canadensis*) | Peppermint Oil |
| Vitamin B8 | Goldenseal (*hydrastis canadensis*) | Spearmint Oil |
| Vitamin B8 | Fenugreek | Mullein |
| Vitamin B8 | Fenugreek | Phenol |
| Vitamin B8 | Fenugreek | Camphor |
| Vitamin B8 | Fenugreek | Pectin |
| Vitamin B8 | Fenugreek | *Eucalyptus* Oil |
| Vitamin B8 | Fenugreek | Peppermint Oil |
| Vitamin B8 | Fenugreek | Spearmint Oil |
| Vitamin B8 | Mullein | Phenol |
| Vitamin B8 | Mullein | Camphor |
| Vitamin B8 | Mullein | Pectin |
| Vitamin B8 | Mullein | *Eucalyptus* Oil |
| Vitamin B8 | Mullein | Peppermint Oil |
| Vitamin B8 | Mullein | Spearmint Oil |
| Vitamin B8 | Phenol | Camphor |
| Vitamin B8 | Phenol | Pectin |
| Vitamin B8 | Phenol | *Eucalyptus* Oil |
| Vitamin B8 | Phenol | Peppermint Oil |
| Vitamin B8 | Phenol | Spearmint Oil |
| Vitamin B8 | Camphor | Pectin |
| Vitamin B8 | Camphor | *Eucalyptus* Oil |
| Vitamin B8 | Camphor | Peppermint Oil |
| Vitamin B8 | Camphor | Spearmint Oil |
| Vitamin B8 | Pectin | *Eucalyptus* Oil |
| Vitamin B8 | Pectin | Peppermint Oil |
| Vitamin B8 | Pectin | Spearmint Oil |
| Vitamin B8 | *Eucalyptus* Oil | Peppermint Oil |
| Vitamin B8 | *Eucalyptus* Oil | Spearmint Oil |
| Vitamin B8 | Peppermint Oil | Spearmint Oil |
| Vitamin B9 | Vitamin B12 | Vitamin C |
| Vitamin B9 | Vitamin B12 | Vitamin E |
| Vitamin B9 | Vitamin B12 | Zinc |
| Vitamin B9 | Vitamin B12 | Magnesium |
| Vitamin B9 | Vitamin B12 | Selenium |
| Vitamin B9 | Vitamin B12 | *Echinacea* |
| Vitamin B9 | Vitamin B12 | Olive leaf (*olea europaea*) |
| Vitamin B9 | Vitamin B12 | Wild indigo (*baptisia tinctoria*) |
| Vitamin B9 | Vitamin B12 | Goldenseal (*hydrastis canadensis*) |
| Vitamin B9 | Vitamin B12 | Fenugreek |
| Vitamin B9 | Vitamin B12 | Mullein |
| Vitamin B9 | Vitamin B12 | Phenol |
| Vitamin B9 | Vitamin B12 | Camphor |
| Vitamin B9 | Vitamin B12 | Pectin |
| Vitamin B9 | Vitamin B12 | *Eucalyptus* Oil |
| Vitamin B9 | Vitamin B12 | Peppermint Oil |
| Vitamin B9 | Vitamin B12 | Spearmint Oil |
| Vitamin B9 | Vitamin C | Vitamin E |
| Vitamin B9 | Vitamin C | Zinc |
| Vitamin B9 | Vitamin C | Magnesium |
| Vitamin B9 | Vitamin C | Selenium |
| Vitamin B9 | Vitamin C | *Echinacea* |
| Vitamin B9 | Vitamin C | Olive leaf (*olea europaea*) |
| Vitamin B9 | Vitamin C | Wild indigo (*baptisia tinctoria*) |
| Vitamin B9 | Vitamin C | Goldenseal (*hydrastis canadensis*) |
| Vitamin B9 | Vitamin C | Fenugreek |
| Vitamin B9 | Vitamin C | Mullein |
| Vitamin B9 | Vitamin C | Phenol |
| Vitamin B9 | Vitamin C | Camphor |
| Vitamin B9 | Vitamin C | Pectin |
| Vitamin B9 | Vitamin C | *Eucalyptus* Oil |
| Vitamin B9 | Vitamin C | Peppermint Oil |
| Vitamin B9 | Vitamin C | Spearmint Oil |
| Vitamin B9 | Vitamin E | Zinc |
| Vitamin B9 | Vitamin E | Magnesium |
| Vitamin B9 | Vitamin E | Selenium |
| Vitamin B9 | Vitamin E | *Echinacea* |
| Vitamin B9 | Vitamin E | Olive leaf (*olea europaea*) |
| Vitamin B9 | Vitamin E | Wild indigo (*baptisia tinctoria*) |
| Vitamin B9 | Vitamin E | Goldenseal (*hydrastis canadensis*) |
| Vitamin B9 | Vitamin E | Fenugreek |
| Vitamin B9 | Vitamin E | Mullein |
| Vitamin B9 | Vitamin E | Phenol |
| Vitamin B9 | Vitamin E | Camphor |
| Vitamin B9 | Vitamin E | Pectin |

TABLE 3-continued

Three Ingredient Combinations

| First Ingredient | Second Ingredient | Third Ingredient |
|---|---|---|
| Vitamin B9 | Vitamin E | *Eucalyptus* Oil |
| Vitamin B9 | Vitamin E | Peppermint Oil |
| Vitamin B9 | Vitamin E | Spearmint Oil |
| Vitamin B9 | Zinc | Magnesium |
| Vitamin B9 | Zinc | Selenium |
| Vitamin B9 | Zinc | *Echinacea* |
| Vitamin B9 | Zinc | Olive leaf (*olea europaea*) |
| Vitamin B9 | Zinc | Wild indigo (*baptisia tinctoria*) |
| Vitamin B9 | Zinc | Goldenseal (*hydrastis canadensis*) |
| Vitamin B9 | Zinc | Fenugreek |
| Vitamin B9 | Zinc | Mullein |
| Vitamin B9 | Zinc | Phenol |
| Vitamin B9 | Zinc | Camphor |
| Vitamin B9 | Zinc | Pectin |
| Vitamin B9 | Zinc | *Eucalyptus* Oil |
| Vitamin B9 | Zinc | Peppermint Oil |
| Vitamin B9 | Zinc | Spearmint Oil |
| Vitamin B9 | Magnesium | Selenium |
| Vitamin B9 | Magnesium | *Echinacea* |
| Vitamin B9 | Magnesium | Olive leaf (*olea europaea*) |
| Vitamin B9 | Magnesium | Wild indigo (*baptisia tinctoria*) |
| Vitamin B9 | Magnesium | Goldenseal (*hydrastis canadensis*) |
| Vitamin B9 | Magnesium | Fenugreek |
| Vitamin B9 | Magnesium | Mullein |
| Vitamin B9 | Magnesium | Phenol |
| Vitamin B9 | Magnesium | Camphor |
| Vitamin B9 | Magnesium | Pectin |
| Vitamin B9 | Magnesium | *Eucalyptus* Oil |
| Vitamin B9 | Magnesium | Peppermint Oil |
| Vitamin B9 | Magnesium | Spearmint Oil |
| Vitamin B9 | Selenium | *Echinacea* |
| Vitamin B9 | Selenium | Olive leaf (*olea europaea*) |
| Vitamin B9 | Selenium | Wild indigo (*baptisia tinctoria*) |
| Vitamin B9 | Selenium | Goldenseal (*hydrastis canadensis*) |
| Vitamin B9 | Selenium | Fenugreek |
| Vitamin B9 | Selenium | Mullein |
| Vitamin B9 | Selenium | Phenol |
| Vitamin B9 | Selenium | Camphor |
| Vitamin B9 | Selenium | Pectin |
| Vitamin B9 | Selenium | *Eucalyptus* Oil |
| Vitamin B9 | Selenium | Peppermint Oil |
| Vitamin B9 | Selenium | Spearmint Oil |
| Vitamin B9 | *Echinacea* | Olive leaf (*olea europaea*) |
| Vitamin B9 | *Echinacea* | Wild indigo (*baptisia tinctoria*) |
| Vitamin B9 | *Echinacea* | Goldenseal (*hydrastis canadensis*) |
| Vitamin B9 | *Echinacea* | Fenugreek |
| Vitamin B9 | *Echinacea* | Mullein |
| Vitamin B9 | *Echinacea* | Phenol |
| Vitamin B9 | *Echinacea* | Camphor |
| Vitamin B9 | *Echinacea* | Pectin |
| Vitamin B9 | *Echinacea* | *Eucalyptus* Oil |
| Vitamin B9 | *Echinacea* | Peppermint Oil |
| Vitamin B9 | *Echinacea* | Spearmint Oil |
| Vitamin B9 | Olive leaf (*olea europaea*) | Wild indigo (*baptisia tinctoria*) |
| Vitamin B9 | Olive leaf (*olea europaea*) | Goldenseal (*hydrastis canadensis*) |
| Vitamin B9 | Olive leaf (*olea europaea*) | Fenugreek |
| Vitamin B9 | Olive leaf (*olea europaea*) | Mullein |
| Vitamin B9 | Olive leaf (*olea europaea*) | Phenol |
| Vitamin B9 | Olive leaf (*olea europaea*) | Camphor |
| Vitamin B9 | Olive leaf (*olea europaea*) | Pectin |
| Vitamin B9 | Olive leaf (*olea europaea*) | *Eucalyptus* Oil |
| Vitamin B9 | Olive leaf (*olea europaea*) | Peppermint Oil |
| Vitamin B9 | Olive leaf (*olea europaea*) | Spearmint Oil |
| Vitamin B9 | Wild indigo (*baptisia tinctoria*) | Goldenseal (*hydrastis canadensis*) |
| Vitamin B9 | Wild indigo (*baptisia tinctoria*) | Fenugreek |
| Vitamin B9 | Wild indigo (*baptisia tinctoria*) | Mullein |
| Vitamin B9 | Wild indigo (*baptisia tinctoria*) | Phenol |
| Vitamin B9 | Wild indigo (*baptisia tinctoria*) | Camphor |
| Vitamin B9 | Wild indigo (*baptisia tinctoria*) | Pectin |
| Vitamin B9 | Wild indigo (*baptisia tinctoria*) | *Eucalyptus* Oil |
| Vitamin B9 | Wild indigo (*baptisia tinctoria*) | Peppermint Oil |
| Vitamin B9 | Wild indigo (*baptisia tinctoria*) | Spearmint Oil |
| Vitamin B9 | Goldenseal (*hydrastis canadensis*) | Fenugreek |
| Vitamin B9 | Goldenseal (*hydrastis canadensis*) | Mullein |
| Vitamin B9 | Goldenseal (*hydrastis canadensis*) | Phenol |
| Vitamin B9 | Goldenseal (*hydrastis canadensis*) | Camphor |

TABLE 3-continued

Three Ingredient Combinations

| First Ingredient | Second Ingredient | Third Ingredient |
|---|---|---|
| Vitamin B9 | Goldenseal (*hydrastis canadensis*) | Pectin |
| Vitamin B9 | Goldenseal (*hydrastis canadensis*) | *Eucalyptus* Oil |
| Vitamin B9 | Goldenseal (*hydrastis canadensis*) | Peppermint Oil |
| Vitamin B9 | Goldenseal (*hydrastis canadensis*) | Spearmint Oil |
| Vitamin B9 | Fenugreek | Mullein |
| Vitamin B9 | Fenugreek | Phenol |
| Vitamin B9 | Fenugreek | Camphor |
| Vitamin B9 | Fenugreek | Pectin |
| Vitamin B9 | Fenugreek | *Eucalyptus* Oil |
| Vitamin B9 | Fenugreek | Peppermint Oil |
| Vitamin B9 | Fenugreek | Spearmint Oil |
| Vitamin B9 | Mullein | Phenol |
| Vitamin B9 | Mullein | Camphor |
| Vitamin B9 | Mullein | Pectin |
| Vitamin B9 | Mullein | *Eucalyptus* Oil |
| Vitamin B9 | Mullein | Peppermint Oil |
| Vitamin B9 | Mullein | Spearmint Oil |
| Vitamin B9 | Phenol | Camphor |
| Vitamin B9 | Phenol | Pectin |
| Vitamin B9 | Phenol | *Eucalyptus* Oil |
| Vitamin B9 | Phenol | Peppermint Oil |
| Vitamin B9 | Phenol | Spearmint Oil |
| Vitamin B9 | Camphor | Pectin |
| Vitamin B9 | Camphor | *Eucalyptus* Oil |
| Vitamin B9 | Camphor | Peppermint Oil |
| Vitamin B9 | Camphor | Spearmint Oil |
| Vitamin B9 | Pectin | *Eucalyptus* Oil |
| Vitamin B9 | Pectin | Peppermint Oil |
| Vitamin B9 | Pectin | Spearmint Oil |
| Vitamin B9 | *Eucalyptus* Oil | Peppermint Oil |
| Vitamin B9 | *Eucalyptus* Oil | Spearmint Oil |
| Vitamin B9 | Peppermint Oil | Spearmint Oil |
| Vitamin B12 | Vitamin C | Vitamin E |
| Vitamin B12 | Vitamin C | Zinc |
| Vitamin B12 | Vitamin C | Magnesium |
| Vitamin B12 | Vitamin C | Selenium |
| Vitamin B12 | Vitamin C | *Echinacea* |
| Vitamin B12 | Vitamin C | Olive leaf (*olea europaea*) |
| Vitamin B12 | Vitamin C | Wild indigo (*baptisia tinctoria*) |
| Vitamin B12 | Vitamin C | Goldenseal (*hydrastis canadensis*) |
| Vitamin B12 | Vitamin C | Fenugreek |
| Vitamin B12 | Vitamin C | Mullein |
| Vitamin B12 | Vitamin C | Phenol |
| Vitamin B12 | Vitamin C | Camphor |
| Vitamin B12 | Vitamin C | Pectin |
| Vitamin B12 | Vitamin C | *Eucalyptus* Oil |
| Vitamin B12 | Vitamin C | Peppermint Oil |
| Vitamin B12 | Vitamin C | Spearmint Oil |
| Vitamin B12 | Vitamin E | Zinc |
| Vitamin B12 | Vitamin E | Magnesium |
| Vitamin B12 | Vitamin E | Selenium |
| Vitamin B12 | Vitamin E | *Echinacea* |
| Vitamin B12 | Vitamin E | Olive leaf (*olea europaea*) |
| Vitamin B12 | Vitamin E | Wild indigo (*baptisia tinctoria*) |
| Vitamin B12 | Vitamin E | Goldenseal (*hydrastis canadensis*) |
| Vitamin B12 | Vitamin E | Fenugreek |
| Vitamin B12 | Vitamin E | Mullein |
| Vitamin B12 | Vitamin E | Phenol |
| Vitamin B12 | Vitamin E | Camphor |
| Vitamin B12 | Vitamin E | Pectin |
| Vitamin B12 | Vitamin E | *Eucalyptus* Oil |
| Vitamin B12 | Vitamin E | Peppermint Oil |
| Vitamin B12 | Vitamin E | Spearmint Oil |
| Vitamin B12 | Zinc | Magnesium |
| Vitamin B12 | Zinc | Selenium |
| Vitamin B12 | Zinc | *Echinacea* |
| Vitamin B12 | Zinc | Olive leaf (*olea europaea*) |
| Vitamin B12 | Zinc | Wild indigo (*baptisia tinctoria*) |
| Vitamin B12 | Zinc | Goldenseal (*hydrastis canadensis*) |
| Vitamin B12 | Zinc | Fenugreek |
| Vitamin B12 | Zinc | Mullein |
| Vitamin B12 | Zinc | Phenol |
| Vitamin B12 | Zinc | Camphor |
| Vitamin B12 | Zinc | Pectin |
| Vitamin B12 | Zinc | *Eucalyptus* Oil |
| Vitamin B12 | Zinc | Peppermint Oil |

TABLE 3-continued

Three Ingredient Combinations

| First Ingredient | Second Ingredient | Third Ingredient |
|---|---|---|
| Vitamin B12 | Zinc | Spearmint Oil |
| Vitamin B12 | Magnesium | Selenium |
| Vitamin B12 | Magnesium | *Echinacea* |
| Vitamin B12 | Magnesium | Olive leaf (*olea europaea*) |
| Vitamin B12 | Magnesium | Wild indigo (*baptisia tinctoria*) |
| Vitamin B12 | Magnesium | Goldenseal (*hydrastis canadensis*) |
| Vitamin B12 | Magnesium | Fenugreek |
| Vitamin B12 | Magnesium | Mullein |
| Vitamin B12 | Magnesium | Phenol |
| Vitamin B12 | Magnesium | Camphor |
| Vitamin B12 | Magnesium | Pectin |
| Vitamin B12 | Magnesium | *Eucalyptus* Oil |
| Vitamin B12 | Magnesium | Peppermint Oil |
| Vitamin B12 | Magnesium | Spearmint Oil |
| Vitamin B12 | Selenium | *Echinacea* |
| Vitamin B12 | Selenium | Olive leaf (*olea europaea*) |
| Vitamin B12 | Selenium | Wild indigo (*baptisia tinctoria*) |
| Vitamin B12 | Selenium | Goldenseal (*hydrastis canadensis*) |
| Vitamin B12 | Selenium | Fenugreek |
| Vitamin B12 | Selenium | Mullein |
| Vitamin B12 | Selenium | Phenol |
| Vitamin B12 | Selenium | Camphor |
| Vitamin B12 | Selenium | Pectin |
| Vitamin B12 | Selenium | *Eucalyptus* Oil |
| Vitamin B12 | Selenium | Peppermint Oil |
| Vitamin B12 | Selenium | Spearmint Oil |
| Vitamin B12 | *Echinacea* | Olive leaf (*olea europaea*) |
| Vitamin B12 | *Echinacea* | Wild indigo (*baptisia tinctoria*) |
| Vitamin B12 | *Echinacea* | Goldenseal (*hydrastis canadensis*) |
| Vitamin B12 | *Echinacea* | Fenugreek |
| Vitamin B12 | *Echinacea* | Mullein |
| Vitamin B12 | *Echinacea* | Phenol |
| Vitamin B12 | *Echinacea* | Camphor |
| Vitamin B12 | *Echinacea* | Pectin |
| Vitamin B12 | *Echinacea* | *Eucalyptus* Oil |
| Vitamin B12 | *Echinacea* | Peppermint Oil |
| Vitamin B12 | *Echinacea* | Spearmint Oil |
| Vitamin B12 | Olive leaf (*olea europaea*) | Wild indigo (*baptisia tinctoria*) |
| Vitamin B12 | Olive leaf (*olea europaea*) | Goldenseal (*hydrastis canadensis*) |
| Vitamin B12 | Olive leaf (*olea europaea*) | Fenugreek |
| Vitamin B12 | Olive leaf (*olea europaea*) | Mullein |
| Vitamin B12 | Olive leaf (*olea europaea*) | Phenol |
| Vitamin B12 | Olive leaf (*olea europaea*) | Camphor |
| Vitamin B12 | Olive leaf (*olea europaea*) | Pectin |
| Vitamin B12 | Olive leaf (*olea europaea*) | *Eucalyptus* Oil |
| Vitamin B12 | Olive leaf (*olea europaea*) | Peppermint Oil |
| Vitamin B12 | Olive leaf (*olea europaea*) | Spearmint Oil |
| Vitamin B12 | Wild indigo (*baptisia tinctoria*) | Goldenseal (*hydrastis canadensis*) |
| Vitamin B12 | Wild indigo (*baptisia tinctoria*) | Fenugreek |
| Vitamin B12 | Wild indigo (*baptisia tinctoria*) | Mullein |
| Vitamin B12 | Wild indigo (*baptisia tinctoria*) | Phenol |
| Vitamin B12 | Wild indigo (*baptisia tinctoria*) | Camphor |
| Vitamin B12 | Wild indigo (*baptisia tinctoria*) | Pectin |
| Vitamin B12 | Wild indigo (*baptisia tinctoria*) | *Eucalyptus* Oil |
| Vitamin B12 | Wild indigo (*baptisia tinctoria*) | Peppermint Oil |
| Vitamin B12 | Wild indigo (*baptisia tinctoria*) | Spearmint Oil |
| Vitamin B12 | Goldenseal (*hydrastis canadensis*) | Fenugreek |
| Vitamin B12 | Goldenseal (*hydrastis canadensis*) | Mullein |
| Vitamin B12 | Goldenseal (*hydrastis canadensis*) | Phenol |
| Vitamin B12 | Goldenseal (*hydrastis canadensis*) | Camphor |
| Vitamin B12 | Goldenseal (*hydrastis canadensis*) | Pectin |
| Vitamin B12 | Goldenseal (*hydrastis canadensis*) | *Eucalyptus* Oil |
| Vitamin B12 | Goldenseal (*hydrastis canadensis*) | Peppermint Oil |
| Vitamin B12 | Goldenseal (*hydrastis canadensis*) | Spearmint Oil |
| Vitamin B12 | Fenugreek | Mullein |
| Vitamin B12 | Fenugreek | Phenol |
| Vitamin B12 | Fenugreek | Camphor |
| Vitamin B12 | Fenugreek | Pectin |
| Vitamin B12 | Fenugreek | *Eucalyptus* Oil |
| Vitamin B12 | Fenugreek | Peppermint Oil |
| Vitamin B12 | Fenugreek | Spearmint Oil |
| Vitamin B12 | Mullein | Phenol |
| Vitamin B12 | Mullein | Camphor |
| Vitamin B12 | Mullein | Pectin |
| Vitamin B12 | Mullein | *Eucalyptus* Oil |
| Vitamin B12 | Mullein | Peppermint Oil |

TABLE 3-continued

Three Ingredient Combinations

| First Ingredient | Second Ingredient | Third Ingredient |
| --- | --- | --- |
| Vitamin B12 | Mullein | Spearmint Oil |
| Vitamin B12 | Phenol | Camphor |
| Vitamin B12 | Phenol | Pectin |
| Vitamin B12 | Phenol | *Eucalyptus* Oil |
| Vitamin B12 | Phenol | Peppermint Oil |
| Vitamin B12 | Phenol | Spearmint Oil |
| Vitamin B12 | Camphor | Pectin |
| Vitamin B12 | Camphor | *Eucalyptus* Oil |
| Vitamin B12 | Camphor | Peppermint Oil |
| Vitamin B12 | Camphor | Spearmint Oil |
| Vitamin B12 | Pectin | *Eucalyptus* Oil |
| Vitamin B12 | Pectin | Peppermint Oil |
| Vitamin B12 | Pectin | Spearmint Oil |
| Vitamin B12 | *Eucalyptus* Oil | Peppermint Oil |
| Vitamin B12 | *Eucalyptus* Oil | Spearmint Oil |
| Vitamin B12 | Peppermint Oil | Spearmint Oil |
| Vitamin C | Vitamin E | Zinc |
| Vitamin C | Vitamin E | Magnesium |
| Vitamin C | Vitamin E | Selenium |
| Vitamin C | Vitamin E | *Echinacea* |
| Vitamin C | Vitamin E | Olive leaf (*olea europaea*) |
| Vitamin C | Vitamin E | Wild indigo (*baptisia tinctoria*) |
| Vitamin C | Vitamin E | Goldenseal (*hydrastis canadensis*) |
| Vitamin C | Vitamin E | Fenugreek |
| Vitamin C | Vitamin E | Mullein |
| Vitamin C | Vitamin E | Phenol |
| Vitamin C | Vitamin E | Camphor |
| Vitamin C | Vitamin E | Pectin |
| Vitamin C | Vitamin E | *Eucalyptus* Oil |
| Vitamin C | Vitamin E | Peppermint Oil |
| Vitamin C | Vitamin E | Spearmint Oil |
| Vitamin C | Zinc | Magnesium |
| Vitamin C | Zinc | Selenium |
| Vitamin C | Zinc | *Echinacea* |
| Vitamin C | Zinc | Olive leaf (*olea europaea*) |
| Vitamin C | Zinc | Wild indigo (*baptisia tinctoria*) |
| Vitamin C | Zinc | Goldenseal (*hydrastis canadensis*) |
| Vitamin C | Zinc | Fenugreek |
| Vitamin C | Zinc | Mullein |
| Vitamin C | Zinc | Phenol |
| Vitamin C | Zinc | Camphor |
| Vitamin C | Zinc | Pectin |
| Vitamin C | Zinc | *Eucalyptus* Oil |
| Vitamin C | Zinc | Peppermint Oil |
| Vitamin C | Zinc | Spearmint Oil |
| Vitamin C | Magnesium | Selenium |
| Vitamin C | Magnesium | *Echinacea* |
| Vitamin C | Magnesium | Olive leaf (*olea europaea*) |
| Vitamin C | Magnesium | Wild indigo (*baptisia tinctoria*) |
| Vitamin C | Magnesium | Goldenseal (*hydrastis canadensis*) |
| Vitamin C | Magnesium | Fenugreek |
| Vitamin C | Magnesium | Mullein |
| Vitamin C | Magnesium | Phenol |
| Vitamin C | Magnesium | Camphor |
| Vitamin C | Magnesium | Pectin |
| Vitamin C | Magnesium | *Eucalyptus* Oil |
| Vitamin C | Magnesium | Peppermint Oil |
| Vitamin C | Magnesium | Spearmint Oil |
| Vitamin C | Selenium | *Echinacea* |
| Vitamin C | Selenium | Olive leaf (*olea europaea*) |
| Vitamin C | Selenium | Wild indigo (*baptisia tinctoria*) |
| Vitamin C | Selenium | Goldenseal (*hydrastis canadensis*) |
| Vitamin C | Selenium | Fenugreek |
| Vitamin C | Selenium | Mullein |
| Vitamin C | Selenium | Phenol |
| Vitamin C | Selenium | Camphor |
| Vitamin C | Selenium | Pectin |
| Vitamin C | Selenium | *Eucalyptus* Oil |
| Vitamin C | Selenium | Peppermint Oil |
| Vitamin C | Selenium | Spearmint Oil |
| Vitamin C | *Echinacea* | Olive leaf (*olea europaea*) |
| Vitamin C | *Echinacea* | Wild indigo (*baptisia tinctoria*) |
| Vitamin C | *Echinacea* | Goldenseal (*hydrastis canadensis*) |
| Vitamin C | *Echinacea* | Fenugreek |
| Vitamin C | *Echinacea* | Mullein |
| Vitamin C | *Echinacea* | Phenol |

TABLE 3-continued

Three Ingredient Combinations

| First Ingredient | Second Ingredient | Third Ingredient |
| --- | --- | --- |
| Vitamin C | *Echinacea* | Camphor |
| Vitamin C | *Echinacea* | Pectin |
| Vitamin C | *Echinacea* | *Eucalyptus* Oil |
| Vitamin C | *Echinacea* | Peppermint Oil |
| Vitamin C | *Echinacea* | Spearmint Oil |
| Vitamin C | Olive leaf (*olea europaea*) | Wild indigo (*baptisia tinctoria*) |
| Vitamin C | Olive leaf (*olea europaea*) | Goldenseal (*hydrastis canadensis*) |
| Vitamin C | Olive leaf (*olea europaea*) | Fenugreek |
| Vitamin C | Olive leaf (*olea europaea*) | Mullein |
| Vitamin C | Olive leaf (*olea europaea*) | Phenol |
| Vitamin C | Olive leaf (*olea europaea*) | Camphor |
| Vitamin C | Olive leaf (*olea europaea*) | Pectin |
| Vitamin C | Olive leaf (*olea europaea*) | *Eucalyptus* Oil |
| Vitamin C | Olive leaf (*olea europaea*) | Peppermint Oil |
| Vitamin C | Olive leaf (*olea europaea*) | Spearmint Oil |
| Vitamin C | Wild indigo (*baptisia tinctoria*) | Goldenseal (*hydrastis canadensis*) |
| Vitamin C | Wild indigo (*baptisia tinctoria*) | Fenugreek |
| Vitamin C | Wild indigo (*baptisia tinctoria*) | Mullein |
| Vitamin C | Wild indigo (*baptisia tinctoria*) | Phenol |
| Vitamin C | Wild indigo (*baptisia tinctoria*) | Camphor |
| Vitamin C | Wild indigo (*baptisia tinctoria*) | Pectin |
| Vitamin C | Wild indigo (*baptisia tinctoria*) | *Eucalyptus* Oil |
| Vitamin C | Wild indigo (*baptisia tinctoria*) | Peppermint Oil |
| Vitamin C | Wild indigo (*baptisia tinctoria*) | Spearmint Oil |
| Vitamin C | Goldenseal (*hydrastis canadensis*) | Fenugreek |
| Vitamin C | Goldenseal (*hydrastis canadensis*) | Mullein |
| Vitamin C | Goldenseal (*hydrastis canadensis*) | Phenol |
| Vitamin C | Goldenseal (*hydrastis canadensis*) | Camphor |
| Vitamin C | Goldenseal (*hydrastis canadensis*) | Pectin |
| Vitamin C | Goldenseal (*hydrastis canadensis*) | *Eucalyptus* Oil |
| Vitamin C | Goldenseal (*hydrastis canadensis*) | Peppermint Oil |
| Vitamin C | Goldenseal (*hydrastis canadensis*) | Spearmint Oil |
| Vitamin C | Fenugreek | Mullein |
| Vitamin C | Fenugreek | Phenol |
| Vitamin C | Fenugreek | Camphor |
| Vitamin C | Fenugreek | Pectin |
| Vitamin C | Fenugreek | *Eucalyptus* Oil |
| Vitamin C | Fenugreek | Peppermint Oil |
| Vitamin C | Fenugreek | Spearmint Oil |
| Vitamin C | Mullein | Phenol |
| Vitamin C | Mullein | Camphor |
| Vitamin C | Mullein | Pectin |
| Vitamin C | Mullein | *Eucalyptus* Oil |
| Vitamin C | Mullein | Peppermint Oil |
| Vitamin C | Mullein | Spearmint Oil |
| Vitamin C | Phenol | Camphor |
| Vitamin C | Phenol | Pectin |
| Vitamin C | Phenol | *Eucalyptus* Oil |
| Vitamin C | Phenol | Peppermint Oil |
| Vitamin C | Phenol | Spearmint Oil |
| Vitamin C | Camphor | Pectin |
| Vitamin C | Camphor | *Eucalyptus* Oil |
| Vitamin C | Camphor | Peppermint Oil |
| Vitamin C | Camphor | Spearmint Oil |
| Vitamin C | Pectin | *Eucalyptus* Oil |
| Vitamin C | Pectin | Peppermint Oil |
| Vitamin C | Pectin | Spearmint Oil |
| Vitamin C | *Eucalyptus* Oil | Peppermint Oil |
| Vitamin C | *Eucalyptus* Oil | Spearmint Oil |
| Vitamin C | Peppermint Oil | Spearmint Oil |
| Vitamin E | Zinc | Magnesium |
| Vitamin E | Zinc | Selenium |
| Vitamin E | Zinc | *Echinacea* |
| Vitamin E | Zinc | Olive leaf (*olea europaea*) |
| Vitamin E | Zinc | Wild indigo (*baptisia tinctoria*) |
| Vitamin E | Zinc | Goldenseal (*hydrastis canadensis*) |
| Vitamin E | Zinc | Fenugreek |
| Vitamin E | Zinc | Mullein |
| Vitamin E | Zinc | Phenol |
| Vitamin E | Zinc | Camphor |
| Vitamin E | Zinc | Pectin |
| Vitamin E | Zinc | *Eucalyptus* Oil |
| Vitamin E | Zinc | Peppermint Oil |
| Vitamin E | Zinc | Spearmint Oil |
| Vitamin E | Magnesium | Selenium |
| Vitamin E | Magnesium | *Echinacea* |

TABLE 3-continued

Three Ingredient Combinations

| First Ingredient | Second Ingredient | Third Ingredient |
| --- | --- | --- |
| Vitamin E | Magnesium | Olive leaf (*olea europaea*) |
| Vitamin E | Magnesium | Wild indigo (*baptisia tinctoria*) |
| Vitamin E | Magnesium | Goldenseal (*hydrastis canadensis*) |
| Vitamin E | Magnesium | Fenugreek |
| Vitamin E | Magnesium | Mullein |
| Vitamin E | Magnesium | Phenol |
| Vitamin E | Magnesium | Camphor |
| Vitamin E | Magnesium | Pectin |
| Vitamin E | Magnesium | *Eucalyptus* Oil |
| Vitamin E | Magnesium | Peppermint Oil |
| Vitamin E | Magnesium | Spearmint Oil |
| Vitamin E | Selenium | *Echinacea* |
| Vitamin E | Selenium | Olive leaf (*olea europaea*) |
| Vitamin E | Selenium | Wild indigo (*baptisia tinctoria*) |
| Vitamin E | Selenium | Goldenseal (*hydrastis canadensis*) |
| Vitamin E | Selenium | Fenugreek |
| Vitamin E | Selenium | Mullein |
| Vitamin E | Selenium | Phenol |
| Vitamin E | Selenium | Camphor |
| Vitamin E | Selenium | Pectin |
| Vitamin E | Selenium | *Eucalyptus* Oil |
| Vitamin E | Selenium | Peppermint Oil |
| Vitamin E | Selenium | Spearmint Oil |
| Vitamin E | *Echinacea* | Olive leaf (*olea europaea*) |
| Vitamin E | *Echinacea* | Wild indigo (*baptisia tinctoria*) |
| Vitamin E | *Echinacea* | Goldenseal (*hydrastis canadensis*) |
| Vitamin E | *Echinacea* | Fenugreek |
| Vitamin E | *Echinacea* | Mullein |
| Vitamin E | *Echinacea* | Phenol |
| Vitamin E | *Echinacea* | Camphor |
| Vitamin E | *Echinacea* | Pectin |
| Vitamin E | *Echinacea* | *Eucalyptus* Oil |
| Vitamin E | *Echinacea* | Peppermint Oil |
| Vitamin E | *Echinacea* | Spearmint Oil |
| Vitamin E | Olive leaf (*olea europaea*) | Wild indigo (*baptisia tinctoria*) |
| Vitamin E | Olive leaf (*olea europaea*) | Goldenseal (*hydrastis canadensis*) |
| Vitamin E | Olive leaf (*olea europaea*) | Fenugreek |
| Vitamin E | Olive leaf (*olea europaea*) | Mullein |
| Vitamin E | Olive leaf (*olea europaea*) | Phenol |
| Vitamin E | Olive leaf (*olea europaea*) | Camphor |
| Vitamin E | Olive leaf (*olea europaea*) | Pectin |
| Vitamin E | Olive leaf (*olea europaea*) | *Eucalyptus* Oil |
| Vitamin E | Olive leaf (*olea europaea*) | Peppermint Oil |
| Vitamin E | Olive leaf (*olea europaea*) | Spearmint Oil |
| Vitamin E | Wild indigo (*baptisia tinctoria*) | Goldenseal (*hydrastis canadensis*) |
| Vitamin E | Wild indigo (*baptisia tinctoria*) | Fenugreek |
| Vitamin E | Wild indigo (*baptisia tinctoria*) | Mullein |
| Vitamin E | Wild indigo (*baptisia tinctoria*) | Phenol |
| Vitamin E | Wild indigo (*baptisia tinctoria*) | Camphor |
| Vitamin E | Wild indigo (*baptisia tinctoria*) | Pectin |
| Vitamin E | Wild indigo (*baptisia tinctoria*) | *Eucalyptus* Oil |
| Vitamin E | Wild indigo (*baptisia tinctoria*) | Peppermint Oil |
| Vitamin E | Wild indigo (*baptisia tinctoria*) | Spearmint Oil |
| Vitamin E | Goldenseal (*hydrastis canadensis*) | Fenugreek |
| Vitamin E | Goldenseal (*hydrastis canadensis*) | Mullein |
| Vitamin E | Goldenseal (*hydrastis canadensis*) | Phenol |
| Vitamin E | Goldenseal (*hydrastis canadensis*) | Camphor |
| Vitamin E | Goldenseal (*hydrastis canadensis*) | Pectin |
| Vitamin E | Goldenseal (*hydrastis canadensis*) | *Eucalyptus* Oil |
| Vitamin E | Goldenseal (*hydrastis canadensis*) | Peppermint Oil |
| Vitamin E | Goldenseal (*hydrastis canadensis*) | Spearmint Oil |
| Vitamin E | Fenugreek | Mullein |
| Vitamin E | Fenugreek | Phenol |
| Vitamin E | Fenugreek | Camphor |
| Vitamin E | Fenugreek | Pectin |
| Vitamin E | Fenugreek | *Eucalyptus* Oil |
| Vitamin E | Fenugreek | Peppermint Oil |
| Vitamin E | Fenugreek | Spearmint Oil |
| Vitamin E | Mullein | Phenol |
| Vitamin E | Mullein | Camphor |
| Vitamin E | Mullein | Pectin |
| Vitamin E | Mullein | *Eucalyptus* Oil |
| Vitamin E | Mullein | Peppermint Oil |
| Vitamin E | Mullein | Spearmint Oil |
| Vitamin E | Phenol | Camphor |
| Vitamin E | Phenol | Pectin |

TABLE 3-continued

Three Ingredient Combinations

| First Ingredient | Second Ingredient | Third Ingredient |
|---|---|---|
| Vitamin E | Phenol | *Eucalyptus* Oil |
| Vitamin E | Phenol | Peppermint Oil |
| Vitamin E | Phenol | Spearmint Oil |
| Vitamin E | Camphor | Pectin |
| Vitamin E | Camphor | *Eucalyptus* Oil |
| Vitamin E | Camphor | Peppermint Oil |
| Vitamin E | Camphor | Spearmint Oil |
| Vitamin E | Pectin | *Eucalyptus* Oil |
| Vitamin E | Pectin | Peppermint Oil |
| Vitamin E | Pectin | Spearmint Oil |
| Vitamin E | *Eucalyptus* Oil | Peppermint Oil |
| Vitamin E | *Eucalyptus* Oil | Spearmint Oil |
| Vitamin E | Peppermint Oil | Spearmint Oil |
| Zinc | Magnesium | Selenium |
| Zinc | Magnesium | *Echinacea* |
| Zinc | Magnesium | Olive leaf (*olea europaea*) |
| Zinc | Magnesium | Wild indigo (*baptisia tinctoria*) |
| Zinc | Magnesium | Goldenseal (*hydrastis canadensis*) |
| Zinc | Magnesium | Fenugreek |
| Zinc | Magnesium | Mullein |
| Zinc | Magnesium | Phenol |
| Zinc | Magnesium | Camphor |
| Zinc | Magnesium | Pectin |
| Zinc | Magnesium | *Eucalyptus* Oil |
| Zinc | Magnesium | Peppermint Oil |
| Zinc | Magnesium | Spearmint Oil |
| Zinc | Selenium | *Echinacea* |
| Zinc | Selenium | Olive leaf (*olea europaea*) |
| Zinc | Selenium | Wild indigo (*baptisia tinctoria*) |
| Zinc | Selenium | Goldenseal (*hydrastis canadensis*) |
| Zinc | Selenium | Fenugreek |
| Zinc | Selenium | Mullein |
| Zinc | Selenium | Phenol |
| Zinc | Selenium | Camphor |
| Zinc | Selenium | Pectin |
| Zinc | Selenium | *Eucalyptus* Oil |
| Zinc | Selenium | Peppermint Oil |
| Zinc | Selenium | Spearmint Oil |
| Zinc | *Echinacea* | Olive leaf (*olea europaea*) |
| Zinc | *Echinacea* | Wild indigo (*baptisia tinctoria*) |
| Zinc | *Echinacea* | Goldenseal (*hydrastis canadensis*) |
| Zinc | *Echinacea* | Fenugreek |
| Zinc | *Echinacea* | Mullein |
| Zinc | *Echinacea* | Phenol |
| Zinc | *Echinacea* | Camphor |
| Zinc | *Echinacea* | Pectin |
| Zinc | *Echinacea* | *Eucalyptus* Oil |
| Zinc | *Echinacea* | Peppermint Oil |
| Zinc | *Echinacea* | Spearmint Oil |
| Zinc | Olive leaf (*olea europaea*) | Wild indigo (*baptisia tinctoria*) |
| Zinc | Olive leaf (*olea europaea*) | Goldenseal (*hydrastis canadensis*) |
| Zinc | Olive leaf (*olea europaea*) | Fenugreek |
| Zinc | Olive leaf (*olea europaea*) | Mullein |
| Zinc | Olive leaf (*olea europaea*) | Phenol |
| Zinc | Olive leaf (*olea europaea*) | Camphor |
| Zinc | Olive leaf (*olea europaea*) | Pectin |
| Zinc | Olive leaf (*olea europaea*) | *Eucalyptus* Oil |
| Zinc | Olive leaf (*olea europaea*) | Peppermint Oil |
| Zinc | Olive leaf (*olea europaea*) | Spearmint Oil |
| Zinc | Wild indigo (*baptisia tinctoria*) | Goldenseal (*hydrastis canadensis*) |
| Zinc | Wild indigo (*baptisia tinctoria*) | Fenugreek |
| Zinc | Wild indigo (*baptisia tinctoria*) | Mullein |
| Zinc | Wild indigo (*baptisia tinctoria*) | Phenol |
| Zinc | Wild indigo (*baptisia tinctoria*) | Camphor |
| Zinc | Wild indigo (*baptisia tinctoria*) | Pectin |
| Zinc | Wild indigo (*baptisia tinctoria*) | *Eucalyptus* Oil |
| Zinc | Wild indigo (*baptisia tinctoria*) | Peppermint Oil |
| Zinc | Wild indigo (*baptisia tinctoria*) | Spearmint Oil |
| Zinc | Goldenseal (*hydrastis canadensis*) | Fenugreek |
| Zinc | Goldenseal (*hydrastis canadensis*) | Mullein |
| Zinc | Goldenseal (*hydrastis canadensis*) | Phenol |
| Zinc | Goldenseal (*hydrastis canadensis*) | Camphor |
| Zinc | Goldenseal (*hydrastis canadensis*) | Pectin |
| Zinc | Goldenseal (*hydrastis canadensis*) | *Eucalyptus* Oil |
| Zinc | Goldenseal (*hydrastis canadensis*) | Peppermint Oil |
| Zinc | Goldenseal (*hydrastis canadensis*) | Spearmint Oil |

TABLE 3-continued

Three Ingredient Combinations

| First Ingredient | Second Ingredient | Third Ingredient |
| --- | --- | --- |
| Zinc | Fenugreek | Mullein |
| Zinc | Fenugreek | Phenol |
| Zinc | Fenugreek | Camphor |
| Zinc | Fenugreek | Pectin |
| Zinc | Fenugreek | *Eucalyptus* Oil |
| Zinc | Fenugreek | Peppermint Oil |
| Zinc | Fenugreek | Spearmint Oil |
| Zinc | Mullein | Phenol |
| Zinc | Mullein | Camphor |
| Zinc | Mullein | Pectin |
| Zinc | Mullein | *Eucalyptus* Oil |
| Zinc | Mullein | Peppermint Oil |
| Zinc | Mullein | Spearmint Oil |
| Zinc | Phenol | Camphor |
| Zinc | Phenol | Pectin |
| Zinc | Phenol | *Eucalyptus* Oil |
| Zinc | Phenol | Peppermint Oil |
| Zinc | Phenol | Spearmint Oil |
| Zinc | Camphor | Pectin |
| Zinc | Camphor | *Eucalyptus* Oil |
| Zinc | Camphor | Peppermint Oil |
| Zinc | Camphor | Spearmint Oil |
| Zinc | Pectin | *Eucalyptus* Oil |
| Zinc | Pectin | Peppermint Oil |
| Zinc | Pectin | Spearmint Oil |
| Zinc | *Eucalyptus* Oil | Peppermint Oil |
| Zinc | *Eucalyptus* Oil | Spearmint Oil |
| Zinc | Peppermint Oil | Spearmint Oil |
| Magnesium | Selenium | *Echinacea* |
| Magnesium | Selenium | Olive leaf (*olea europaea*) |
| Magnesium | Selenium | Wild indigo (*baptisia tinctoria*) |
| Magnesium | Selenium | Goldenseal (*hydrastis canadensis*) |
| Magnesium | Selenium | Fenugreek |
| Magnesium | Selenium | Mullein |
| Magnesium | Selenium | Phenol |
| Magnesium | Selenium | Camphor |
| Magnesium | Selenium | Pectin |
| Magnesium | Selenium | *Eucalyptus* Oil |
| Magnesium | Selenium | Peppermint Oil |
| Magnesium | Selenium | Spearmint Oil |
| Magnesium | *Echinacea* | Olive leaf (*olea europaea*) |
| Magnesium | *Echinacea* | Wild indigo (*baptisia tinctoria*) |
| Magnesium | *Echinacea* | Goldenseal (*hydrastis canadensis*) |
| Magnesium | *Echinacea* | Fenugreek |
| Magnesium | *Echinacea* | Mullein |
| Magnesium | *Echinacea* | Phenol |
| Magnesium | *Echinacea* | Camphor |
| Magnesium | *Echinacea* | Pectin |
| Magnesium | *Echinacea* | *Eucalyptus* Oil |
| Magnesium | *Echinacea* | Peppermint Oil |
| Magnesium | *Echinacea* | Spearmint Oil |
| Magnesium | Olive leaf (*olea europaea*) | Wild indigo (*baptisia tinctoria*) |
| Magnesium | Olive leaf (*olea europaea*) | Goldenseal (*hydrastis canadensis*) |
| Magnesium | Olive leaf (*olea europaea*) | Fenugreek |
| Magnesium | Olive leaf (*olea europaea*) | Mullein |
| Magnesium | Olive leaf (*olea europaea*) | Phenol |
| Magnesium | Olive leaf (*olea europaea*) | Camphor |
| Magnesium | Olive leaf (*olea europaea*) | Pectin |
| Magnesium | Olive leaf (*olea europaea*) | *Eucalyptus* Oil |
| Magnesium | Olive leaf (*olea europaea*) | Peppermint Oil |
| Magnesium | Olive leaf (*olea europaea*) | Spearmint Oil |
| Magnesium | Wild indigo (*baptisia tinctoria*) | Goldenseal (*hydrastis canadensis*) |
| Magnesium | Wild indigo (*baptisia tinctoria*) | Fenugreek |
| Magnesium | Wild indigo (*baptisia tinctoria*) | Mullein |
| Magnesium | Wild indigo (*baptisia tinctoria*) | Phenol |
| Magnesium | Wild indigo (*baptisia tinctoria*) | Camphor |
| Magnesium | Wild indigo (*baptisia tinctoria*) | Pectin |
| Magnesium | Wild indigo (*baptisia tinctoria*) | *Eucalyptus* Oil |
| Magnesium | Wild indigo (*baptisia tinctoria*) | Peppermint Oil |
| Magnesium | Wild indigo (*baptisia tinctoria*) | Spearmint Oil |
| Magnesium | Goldenseal (*hydrastis canadensis*) | Fenugreek |
| Magnesium | Goldenseal (*hydrastis canadensis*) | Mullein |
| Magnesium | Goldenseal (*hydrastis canadensis*) | Phenol |
| Magnesium | Goldenseal (*hydrastis canadensis*) | Camphor |
| Magnesium | Goldenseal (*hydrastis canadensis*) | Pectin |
| Magnesium | Goldenseal (*hydrastis canadensis*) | *Eucalyptus* Oil |

TABLE 3-continued

Three Ingredient Combinations

| First Ingredient | Second Ingredient | Third Ingredient |
|---|---|---|
| Magnesium | Goldenseal (*hydrastis canadensis*) | Peppermint Oil |
| Magnesium | Goldenseal (*hydrastis canadensis*) | Spearmint Oil |
| Magnesium | Fenugreek | Mullein |
| Magnesium | Fenugreek | Phenol |
| Magnesium | Fenugreek | Camphor |
| Magnesium | Fenugreek | Pectin |
| Magnesium | Fenugreek | *Eucalyptus* Oil |
| Magnesium | Fenugreek | Peppermint Oil |
| Magnesium | Fenugreek | Spearmint Oil |
| Magnesium | Mullein | Phenol |
| Magnesium | Mullein | Camphor |
| Magnesium | Mullein | Pectin |
| Magnesium | Mullein | *Eucalyptus* Oil |
| Magnesium | Mullein | Peppermint Oil |
| Magnesium | Mullein | Spearmint Oil |
| Magnesium | Phenol | Camphor |
| Magnesium | Phenol | Pectin |
| Magnesium | Phenol | *Eucalyptus* Oil |
| Magnesium | Phenol | Peppermint Oil |
| Magnesium | Phenol | Spearmint Oil |
| Magnesium | Camphor | Pectin |
| Magnesium | Camphor | *Eucalyptus* Oil |
| Magnesium | Camphor | Peppermint Oil |
| Magnesium | Camphor | Spearmint Oil |
| Magnesium | Pectin | *Eucalyptus* Oil |
| Magnesium | Pectin | Peppermint Oil |
| Magnesium | Pectin | Spearmint Oil |
| Magnesium | *Eucalyptus* Oil | Peppermint Oil |
| Magnesium | *Eucalyptus* Oil | Spearmint Oil |
| Magnesium | Peppermint Oil | Spearmint Oil |
| Selenium | *Echinacea* | Olive leaf (*olea europaea*) |
| Selenium | *Echinacea* | Wild indigo (*baptisia tinctoria*) |
| Selenium | *Echinacea* | Goldenseal (*hydrastis canadensis*) |
| Selenium | *Echinacea* | Fenugreek |
| Selenium | *Echinacea* | Mullein |
| Selenium | *Echinacea* | Phenol |
| Selenium | *Echinacea* | Camphor |
| Selenium | *Echinacea* | Pectin |
| Selenium | *Echinacea* | *Eucalyptus* Oil |
| Selenium | *Echinacea* | Peppermint Oil |
| Selenium | *Echinacea* | Spearmint Oil |
| Selenium | Olive leaf (*olea europaea*) | Wild indigo (*baptisia tinctoria*) |
| Selenium | Olive leaf (*olea europaea*) | Goldenseal (*hydrastis canadensis*) |
| Selenium | Olive leaf (*olea europaea*) | Fenugreek |
| Selenium | Olive leaf (*olea europaea*) | Mullein |
| Selenium | Olive leaf (*olea europaea*) | Phenol |
| Selenium | Olive leaf (*olea europaea*) | Camphor |
| Selenium | Olive leaf (*olea europaea*) | Pectin |
| Selenium | Olive leaf (*olea europaea*) | *Eucalyptus* Oil |
| Selenium | Olive leaf (*olea europaea*) | Peppermint Oil |
| Selenium | Olive leaf (*olea europaea*) | Spearmint Oil |
| Selenium | Wild indigo (*baptisia tinctoria*) | Goldenseal (*hydrastis canadensis*) |
| Selenium | Wild indigo (*baptisia tinctoria*) | Fenugreek |
| Selenium | Wild indigo (*baptisia tinctoria*) | Mullein |
| Selenium | Wild indigo (*baptisia tinctoria*) | Phenol |
| Selenium | Wild indigo (*baptisia tinctoria*) | Camphor |
| Selenium | Wild indigo (*baptisia tinctoria*) | Pectin |
| Selenium | Wild indigo (*baptisia tinctoria*) | *Eucalyptus* Oil |
| Selenium | Wild indigo (*baptisia tinctoria*) | Peppermint Oil |
| Selenium | Wild indigo (*baptisia tinctoria*) | Spearmint Oil |
| Selenium | Goldenseal (*hydrastis canadensis*) | Fenugreek |
| Selenium | Goldenseal (*hydrastis canadensis*) | Mullein |
| Selenium | Goldenseal (*hydrastis canadensis*) | Phenol |
| Selenium | Goldenseal (*hydrastis canadensis*) | Camphor |
| Selenium | Goldenseal (*hydrastis canadensis*) | Pectin |
| Selenium | Goldenseal (*hydrastis canadensis*) | *Eucalyptus* Oil |
| Selenium | Goldenseal (*hydrastis canadensis*) | Peppermint Oil |
| Selenium | Goldenseal (*hydrastis canadensis*) | Spearmint Oil |
| Selenium | Fenugreek | Mullein |
| Selenium | Fenugreek | Phenol |
| Selenium | Fenugreek | Camphor |
| Selenium | Fenugreek | Pectin |
| Selenium | Fenugreek | *Eucalyptus* Oil |
| Selenium | Fenugreek | Peppermint Oil |
| Selenium | Fenugreek | Spearmint Oil |
| Selenium | Mullein | Phenol |

TABLE 3-continued

Three Ingredient Combinations

| First Ingredient | Second Ingredient | Third Ingredient |
|---|---|---|
| Selenium | Mullein | Camphor |
| Selenium | Mullein | Pectin |
| Selenium | Mullein | *Eucalyptus* Oil |
| Selenium | Mullein | Peppermint Oil |
| Selenium | Mullein | Spearmint Oil |
| Selenium | Phenol | Camphor |
| Selenium | Phenol | Pectin |
| Selenium | Phenol | *Eucalyptus* Oil |
| Selenium | Phenol | Peppermint Oil |
| Selenium | Phenol | Spearmint Oil |
| Selenium | Camphor | Pectin |
| Selenium | Camphor | *Eucalyptus* Oil |
| Selenium | Camphor | Peppermint Oil |
| Selenium | Camphor | Spearmint Oil |
| Selenium | Pectin | *Eucalyptus* Oil |
| Selenium | Pectin | Peppermint Oil |
| Selenium | Pectin | Spearmint Oil |
| Selenium | *Eucalyptus* Oil | Peppermint Oil |
| Selenium | *Eucalyptus* Oil | Spearmint Oil |
| Selenium | Peppermint Oil | Spearmint Oil |
| Echinacea | Olive leaf (*olea europaea*) | Wild indigo (*baptisia tinctoria*) |
| Echinacea | Olive leaf (*olea europaea*) | Goldenseal (*hydrastis canadensis*) |
| Echinacea | Olive leaf (*olea europaea*) | Fenugreek |
| Echinacea | Olive leaf (*olea europaea*) | Mullein |
| Echinacea | Olive leaf (*olea europaea*) | Phenol |
| Echinacea | Olive leaf (*olea europaea*) | Camphor |
| Echinacea | Olive leaf (*olea europaea*) | Pectin |
| Echinacea | Olive leaf (*olea europaea*) | *Eucalyptus* Oil |
| Echinacea | Olive leaf (*olea europaea*) | Peppermint Oil |
| Echinacea | Olive leaf (*olea europaea*) | Spearmint Oil |
| Echinacea | Wild indigo (*baptisia tinctoria*) | Goldenseal (*hydrastis canadensis*) |
| Echinacea | Wild indigo (*baptisia tinctoria*) | Fenugreek |
| Echinacea | Wild indigo (*baptisia tinctoria*) | Mullein |
| Echinacea | Wild indigo (*baptisia tinctoria*) | Phenol |
| Echinacea | Wild indigo (*baptisia tinctoria*) | Camphor |
| Echinacea | Wild indigo (*baptisia tinctoria*) | Pectin |
| Echinacea | Wild indigo (*baptisia tinctoria*) | *Eucalyptus* Oil |
| Echinacea | Wild indigo (*baptisia tinctoria*) | Peppermint Oil |
| Echinacea | Wild indigo (*baptisia tinctoria*) | Spearmint Oil |
| Echinacea | Goldenseal (*hydrastis canadensis*) | Fenugreek |
| Echinacea | Goldenseal (*hydrastis canadensis*) | Mullein |
| Echinacea | Goldenseal (*hydrastis canadensis*) | Phenol |
| Echinacea | Goldenseal (*hydrastis canadensis*) | Camphor |
| Echinacea | Goldenseal (*hydrastis canadensis*) | Pectin |
| Echinacea | Goldenseal (*hydrastis canadensis*) | *Eucalyptus* Oil |
| Echinacea | Goldenseal (*hydrastis canadensis*) | Peppermint Oil |
| Echinacea | Goldenseal (*hydrastis canadensis*) | Spearmint Oil |
| Echinacea | Fenugreek | Mullein |
| Echinacea | Fenugreek | Phenol |
| Echinacea | Fenugreek | Camphor |
| Echinacea | Fenugreek | Pectin |
| Echinacea | Fenugreek | *Eucalyptus* Oil |
| Echinacea | Fenugreek | Peppermint Oil |
| Echinacea | Fenugreek | Spearmint Oil |
| Echinacea | Mullein | Phenol |
| Echinacea | Mullein | Camphor |
| Echinacea | Mullein | Pectin |
| Echinacea | Mullein | *Eucalyptus* Oil |
| Echinacea | Mullein | Peppermint Oil |
| Echinacea | Mullein | Spearmint Oil |
| Echinacea | Phenol | Camphor |
| Echinacea | Phenol | Pectin |
| Echinacea | Phenol | *Eucalyptus* Oil |
| Echinacea | Phenol | Peppermint Oil |
| Echinacea | Phenol | Spearmint Oil |
| Echinacea | Camphor | Pectin |
| Echinacea | Camphor | *Eucalyptus* Oil |
| Echinacea | Camphor | Peppermint Oil |
| Echinacea | Camphor | Spearmint Oil |
| Echinacea | Pectin | *Eucalyptus* Oil |
| Echinacea | Pectin | Peppermint Oil |
| Echinacea | Pectin | Spearmint Oil |
| Echinacea | *Eucalyptus* Oil | Peppermint Oil |
| Echinacea | *Eucalyptus* Oil | Spearmint Oil |
| Echinacea | Peppermint Oil | Spearmint Oil |
| Olive leaf (*olea europaea*) | Wild indigo (*baptisia tinctoria*) | Goldenseal (*hydrastis canadensis*) |

TABLE 3-continued

Three Ingredient Combinations

| First Ingredient | Second Ingredient | Third Ingredient |
| --- | --- | --- |
| Olive leaf (*olea europaea*) | Wild indigo (*baptisia tinctoria*) | Fenugreek |
| Olive leaf (*olea europaea*) | Wild indigo (*baptisia tinctoria*) | Mullein |
| Olive leaf (*olea europaea*) | Wild indigo (*baptisia tinctoria*) | Phenol |
| Olive leaf (*olea europaea*) | Wild indigo (*baptisia tinctoria*) | Camphor |
| Olive leaf (*olea europaea*) | Wild indigo (*baptisia tinctoria*) | Pectin |
| Olive leaf (*olea europaea*) | Wild indigo (*baptisia tinctoria*) | *Eucalyptus* Oil |
| Olive leaf (*olea europaea*) | Wild indigo (*baptisia tinctoria*) | Peppermint Oil |
| Olive leaf (*olea europaea*) | Wild indigo (*baptisia tinctoria*) | Spearmint Oil |
| Olive leaf (*olea europaea*) | Goldenseal (*hydrastis canadensis*) | Fenugreek |
| Olive leaf (*olea europaea*) | Goldenseal (*hydrastis canadensis*) | Mullein |
| Olive leaf (*olea europaea*) | Goldenseal (*hydrastis canadensis*) | Phenol |
| Olive leaf (*olea europaea*) | Goldenseal (*hydrastis canadensis*) | Camphor |
| Olive leaf (*olea europaea*) | Goldenseal (*hydrastis canadensis*) | Pectin |
| Olive leaf (*olea europaea*) | Goldenseal (*hydrastis canadensis*) | *Eucalyptus* Oil |
| Olive leaf (*olea europaea*) | Goldenseal (*hydrastis canadensis*) | Peppermint Oil |
| Olive leaf (*olea europaea*) | Goldenseal (*hydrastis canadensis*) | Spearmint Oil |
| Olive leaf (*olea europaea*) | Fenugreek | Mullein |
| Olive leaf (*olea europaea*) | Fenugreek | Phenol |
| Olive leaf (*olea europaea*) | Fenugreek | Camphor |
| Olive leaf (*olea europaea*) | Fenugreek | Pectin |
| Olive leaf (*olea europaea*) | Fenugreek | *Eucalyptus* Oil |
| Olive leaf (*olea europaea*) | Fenugreek | Peppermint Oil |
| Olive leaf (*olea europaea*) | Fenugreek | Spearmint Oil |
| Olive leaf (*olea europaea*) | Mullein | Phenol |
| Olive leaf (*olea europaea*) | Mullein | Camphor |
| Olive leaf (*olea europaea*) | Mullein | Pectin |
| Olive leaf (*olea europaea*) | Mullein | *Eucalyptus* Oil |
| Olive leaf (*olea europaea*) | Mullein | Peppermint Oil |
| Olive leaf (*olea europaea*) | Mullein | Spearmint Oil |
| Olive leaf (*olea europaea*) | Phenol | Camphor |
| Olive leaf (*olea europaea*) | Phenol | Pectin |
| Olive leaf (*olea europaea*) | Phenol | *Eucalyptus* Oil |
| Olive leaf (*olea europaea*) | Phenol | Peppermint Oil |
| Olive leaf (*olea europaea*) | Phenol | Spearmint Oil |
| Olive leaf (*olea europaea*) | Camphor | Pectin |
| Olive leaf (*olea europaea*) | Camphor | *Eucalyptus* Oil |
| Olive leaf (*olea europaea*) | Camphor | Peppermint Oil |
| Olive leaf (*olea europaea*) | Camphor | Spearmint Oil |
| Olive leaf (*olea europaea*) | Pectin | *Eucalyptus* Oil |
| Olive leaf (*olea europaea*) | Pectin | Peppermint Oil |
| Olive leaf (*olea europaea*) | Pectin | Spearmint Oil |
| Olive leaf (*olea europaea*) | *Eucalyptus* Oil | Peppermint Oil |
| Olive leaf (*olea europaea*) | *Eucalyptus* Oil | Spearmint Oil |
| Olive leaf (*olea europaea*) | Peppermint Oil | Spearmint Oil |
| Wild indigo (*baptisia tinctoria*) | Goldenseal (*hydrastis canadensis*) | Fenugreek |
| Wild indigo (*baptisia tinctoria*) | Goldenseal (*hydrastis canadensis*) | Mullein |
| Wild indigo (*baptisia tinctoria*) | Goldenseal (*hydrastis canadensis*) | Phenol |
| Wild indigo (*baptisia tinctoria*) | Goldenseal (*hydrastis canadensis*) | Camphor |
| Wild indigo (*baptisia tinctoria*) | Goldenseal (*hydrastis canadensis*) | Pectin |
| Wild indigo (*baptisia tinctoria*) | Goldenseal (*hydrastis canadensis*) | *Eucalyptus* Oil |
| Wild indigo (*baptisia tinctoria*) | Goldenseal (*hydrastis canadensis*) | Peppermint Oil |
| Wild indigo (*baptisia tinctoria*) | Goldenseal (*hydrastis canadensis*) | Spearmint Oil |
| Wild indigo (*baptisia tinctoria*) | Fenugreek | Mullein |
| Wild indigo (*baptisia tinctoria*) | Fenugreek | Phenol |
| Wild indigo (*baptisia tinctoria*) | Fenugreek | Camphor |
| Wild indigo (*baptisia tinctoria*) | Fenugreek | Pectin |
| Wild indigo (*baptisia tinctoria*) | Fenugreek | *Eucalyptus* Oil |
| Wild indigo (*baptisia tinctoria*) | Fenugreek | Peppermint Oil |
| Wild indigo (*baptisia tinctoria*) | Fenugreek | Spearmint Oil |
| Wild indigo (*baptisia tinctoria*) | Mullein | Phenol |
| Wild indigo (*baptisia tinctoria*) | Mullein | Camphor |
| Wild indigo (*baptisia tinctoria*) | Mullein | Pectin |
| Wild indigo (*baptisia tinctoria*) | Mullein | *Eucalyptus* Oil |
| Wild indigo (*baptisia tinctoria*) | Mullein | Peppermint Oil |
| Wild indigo (*baptisia tinctoria*) | Mullein | Spearmint Oil |
| Wild indigo (*baptisia tinctoria*) | Phenol | Camphor |
| Wild indigo (*baptisia tinctoria*) | Phenol | Pectin |
| Wild indigo (*baptisia tinctoria*) | Phenol | *Eucalyptus* Oil |
| Wild indigo (*baptisia tinctoria*) | Phenol | Peppermint Oil |
| Wild indigo (*baptisia tinctoria*) | Phenol | Spearmint Oil |
| Wild indigo (*baptisia tinctoria*) | Camphor | Pectin |
| Wild indigo (*baptisia tinctoria*) | Camphor | *Eucalyptus* Oil |
| Wild indigo (*baptisia tinctoria*) | Camphor | Peppermint Oil |
| Wild indigo (*baptisia tinctoria*) | Camphor | Spearmint Oil |
| Wild indigo (*baptisia tinctoria*) | Pectin | *Eucalyptus* Oil |
| Wild indigo (*baptisia tinctoria*) | Pectin | Peppermint Oil |

TABLE 3-continued

Three Ingredient Combinations

| First Ingredient | Second Ingredient | Third Ingredient |
|---|---|---|
| Wild indigo (*baptisia tinctoria*) | Pectin | Spearmint Oil |
| Wild indigo (*baptisia tinctoria*) | *Eucalyptus* Oil | Peppermint Oil |
| Wild indigo (*baptisia tinctoria*) | *Eucalyptus* Oil | Spearmint Oil |
| Wild indigo (*baptisia tinctoria*) | Peppermint Oil | Spearmint Oil |
| Goldenseal (*hydrastis canadensis*) | Fenugreek | Mullein |
| Goldenseal (*hydrastis canadensis*) | Fenugreek | Phenol |
| Goldenseal (*hydrastis canadensis*) | Fenugreek | Camphor |
| Goldenseal (*hydrastis canadensis*) | Fenugreek | Pectin |
| Goldenseal (*hydrastis canadensis*) | Fenugreek | *Eucalyptus* Oil |
| Goldenseal (*hydrastis canadensis*) | Fenugreek | Peppermint Oil |
| Goldenseal (*hydrastis canadensis*) | Fenugreek | Spearmint Oil |
| Goldenseal (*hydrastis canadensis*) | Mullein | Phenol |
| Goldenseal (*hydrastis canadensis*) | Mullein | Camphor |
| Goldenseal (*hydrastis canadensis*) | Mullein | Pectin |
| Goldenseal (*hydrastis canadensis*) | Mullein | *Eucalyptus* Oil |
| Goldenseal (*hydrastis canadensis*) | Mullein | Peppermint Oil |
| Goldenseal (*hydrastis canadensis*) | Mullein | Spearmint Oil |
| Goldenseal (*hydrastis canadensis*) | Phenol | Camphor |
| Goldenseal (*hydrastis canadensis*) | Phenol | Pectin |
| Goldenseal (*hydrastis canadensis*) | Phenol | *Eucalyptus* Oil |
| Goldenseal (*hydrastis canadensis*) | Phenol | Peppermint Oil |
| Goldenseal (*hydrastis canadensis*) | Phenol | Spearmint Oil |
| Goldenseal (*hydrastis canadensis*) | Camphor | Pectin |
| Goldenseal (*hydrastis canadensis*) | Camphor | *Eucalyptus* Oil |
| Goldenseal (*hydrastis canadensis*) | Camphor | Peppermint Oil |
| Goldenseal (*hydrastis canadensis*) | Camphor | Spearmint Oil |
| Goldenseal (*hydrastis canadensis*) | Pectin | *Eucalyptus* Oil |
| Goldenseal (*hydrastis canadensis*) | Pectin | Peppermint Oil |
| Goldenseal (*hydrastis canadensis*) | Pectin | Spearmint Oil |
| Goldenseal (*hydrastis canadensis*) | *Eucalyptus* Oil | Peppermint Oil |
| Goldenseal (*hydrastis canadensis*) | *Eucalyptus* Oil | Spearmint Oil |
| Goldenseal (*hydrastis canadensis*) | Peppermint Oil | Spearmint Oil |
| Fenugreek | Mullein | Phenol |
| Fenugreek | Mullein | Camphor |
| Fenugreek | Mullein | Pectin |
| Fenugreek | Mullein | *Eucalyptus* Oil |
| Fenugreek | Mullein | Peppermint Oil |
| Fenugreek | Mullein | Spearmint Oil |
| Fenugreek | Phenol | Camphor |
| Fenugreek | Phenol | Pectin |
| Fenugreek | Phenol | *Eucalyptus* Oil |
| Fenugreek | Phenol | Peppermint Oil |
| Fenugreek | Phenol | Spearmint Oil |
| Fenugreek | Camphor | Pectin |
| Fenugreek | Camphor | *Eucalyptus* Oil |
| Fenugreek | Camphor | Peppermint Oil |
| Fenugreek | Camphor | Spearmint Oil |
| Fenugreek | Pectin | *Eucalyptus* Oil |
| Fenugreek | Pectin | Peppermint Oil |
| Fenugreek | Pectin | Spearmint Oil |
| Fenugreek | *Eucalyptus* Oil | Peppermint Oil |
| Fenugreek | *Eucalyptus* Oil | Spearmint Oil |
| Fenugreek | Peppermint Oil | Spearmint Oil |
| Mullein | Phenol | Camphor |
| Mullein | Phenol | Pectin |
| Mullein | Phenol | *Eucalyptus* Oil |
| Mullein | Phenol | Peppermint Oil |
| Mullein | Phenol | Spearmint Oil |
| Mullein | Camphor | Pectin |
| Mullein | Camphor | *Eucalyptus* Oil |
| Mullein | Camphor | Peppermint Oil |
| Mullein | Camphor | Spearmint Oil |
| Mullein | Pectin | *Eucalyptus* Oil |
| Mullein | Pectin | Peppermint Oil |
| Mullein | Pectin | Spearmint Oil |
| Mullein | *Eucalyptus* Oil | Peppermint Oil |
| Mullein | *Eucalyptus* Oil | Spearmint Oil |
| Mullein | Peppermint Oil | Spearmint Oil |
| Phenol | Camphor | Pectin |
| Phenol | Camphor | *Eucalyptus* Oil |
| Phenol | Camphor | Peppermint Oil |
| Phenol | Camphor | Spearmint Oil |
| Phenol | Pectin | *Eucalyptus* Oil |
| Phenol | Pectin | Peppermint Oil |
| Phenol | Pectin | Spearmint Oil |
| Phenol | *Eucalyptus* Oil | Peppermint Oil |

TABLE 3-continued

Three Ingredient Combinations

| First Ingredient | Second Ingredient | Third Ingredient |
|---|---|---|
| Phenol | *Eucalyptus* Oil | Spearmint Oil |
| Phenol | Peppermint Oil | Spearmint Oil |
| Camphor | Pectin | *Eucalyptus* Oil |
| Camphor | Pectin | Peppermint Oil |
| Camphor | Pectin | Spearmint Oil |
| Camphor | *Eucalyptus* Oil | Peppermint Oil |
| Camphor | *Eucalyptus* Oil | Spearmint Oil |
| Camphor | Peppermint Oil | Spearmint Oil |
| Pectin | *Eucalyptus* Oil | Peppermint Oil |
| Pectin | *Eucalyptus* Oil | Spearmint Oil |
| Pectin | Peppermint Oil | Spearmint Oil |
| *Eucalyptus* Oil | Peppermint Oil | Spearmint Oil |

Methods of Use

When the mouthpiece is coated with candy (e.g., to create a lollipop), the safety handle finds use for delivering candy and active agents in the dissolving candy to a subject. For example, the safety handle finds use in delivering fentanyl or other orally administrable active agents to a subject. In varying embodiments, the safety handle finds use in treating ear infections in a subject in need thereof.

Subjects Who May Benefit

Generally, the subject is suffering ear pain or experiencing pressure within the inner ear. For example, the subject may have excess fluid in the inner ear canal or fluid that is clogging the Eustachian tubes or the inner ear canal. The subject may or may not have an ear infection. In various embodiments, the subject has, or has been diagnosed as having, acute otitis media (AOM); otitis media with effusion (OME); chronic otitis media (COM); or acute otitis externa (AOE). Usually, the subject, patient or individual is a human.

Lollipops having the present safety handles have utility in the treatment of AOM ear infections and the pain associated with AOM ear infections in human children. In order to ensure the effectiveness of the candy coating the mouthpiece of the safety handle lollipop described herein to small children, the candy is intended to be as palatable as possible to small children in a mode of administration that is easily administrable to small children. It is to be understood; however, that the use of the safety handle lollipops is not limited to the treatment of AOM in human children and that the safety handle lollipops may also find utility in the treatment of ear infections in adolescents and adults suffering from AOM. The safety handle lollipops are also intended to have utility in the treatment of ear infections other than AOM, such as for example, OME, COM, and AOE, in children, adolescents, and adults.

The methods are particularly effective in small children because the Eustachian tubes of small children are more horizontally positioned than those of adults. As a human individual ages, the position of the Eustachian tubes shifts from a horizontal position to a more vertical position. In this way, the effect of the sucking and pulling on the Eustachian tube (e.g., by sucking and swallowing) is more pronounced in small children than in adolescents and adults. Notwithstanding the foregoing, use of a lollipop having the present safety handle is capable of treating ear infections and its associated pain in adults.

Methods of Treating Ear Infections

In practicing the present methods, the individual sucks on a lollipop having the safety handle described herein lying down with the affected ear facing up. Sucking on the safety handle lollipops compels the production of saliva and the action of swallowing. It is believed that the present methods help clear the Eustachian tubes (ET) by the swallowing associated with sucking on the salivary producing composition because the swallowing motion contracts the muscles around the ET and causes opening of the ET. The negative pressure created by sucking coupled with the contraction of the muscles to cause opening of the tube by swallowing, assisted by gravity where the infected ear or ear with a clogged or blocked ET is facing up all combine to drain the tubes. In addition, in certain embodiments, i.e., where the composition includes one or more anti-inflammatory ingredients, the anti-inflammatory characteristics of the composition can help reduce the swelling around the opening of the ET thereby making it easier for the ET to open during swallowing.

The present safety handle lollipops can be in any suitable shape and is generally of a size to fit comfortably within the oral cavity of the subject. In various embodiments, the candy coating around the mouthpiece is disc shaped, spherically shaped, elliptically shaped, oblong, polyhedral (e.g., octahedral) or octagonal. In various embodiments, the candy coating around the mouthpiece is in the shape of the oral cavity, e.g., flat on the surface that contacts the tongue, convex on the surface that contacts the roof of the mouth, and of a size that fits comfortably within the oral cavity of the subject.

The shape of the candy-coated mouthpiece can influence the strength of the negative pressure achieved within the oral cavity. In addition, sucking on a candy-coated mouthpiece in the form or shape of a human oral cavity can increase the amount of saliva production in the oral cavity, thereby facilitating the effectiveness of clearing blocked fluid from the inner ear canal or ET. Determination of the amount of saliva production can be measured using any method known in the art. In one embodiment, saliva production can be measured with the Saxon test, a simple gauze-chewing procedure. See, e.g., Kohler and Winter, Arthritis Rheum. (1985) 28(10):1128-32; and Stevens, et al., Am J Dis Child. (1990) 144(5):570-1. In some embodiments, sucking on a candy-coated mouthpiece described herein can increase the amount of saliva production in the oral cavity by at least about 5%, 10%, 15%, 20% or 25%, e.g., in comparison to a baseline, e.g., the amount of saliva produced when the subject is not sucking on anything. Including ingredients such as sugar, peppermint oil and/or citric acid can facilitate production of saliva. Determination of negative pressure within the oral cavity can also be measured using any method known in the art. In one embodiment, negative pressure within the oral cavity is measured by atmospheric pressure monitoring simultaneously carried out with a digital manometer in the vestibular inter-occlusal space (IOS) and at the palatal vault (sub-palatal space, SPS). See, e.g., Engelke, et al., Clin Oral Investig. (2011) 15(2):165-76. Intra-oral pressure can also be measured using oral end fittings connected to a piezo-resistive relative pressure sensor. See, e.g., Knosel, et al., Eur J Orthod. (2010) 32(5): 535-41. In some embodiments, sucking on a candy-coated mouthpiece described herein can increase the amount of negative pressure in the oral cavity by at least about 5%, 10%, 15%, 20% or 25%, e.g., in comparison to a baseline, e.g., the amount of negative pressure formed in the oral cavity when the subject is sucking on a candy composition that is not in the shape of a human oral cavity.

With respect to the posture and position of the subject for practicing the methods, in various embodiments, the subject is lying down with the affected ear facing up. The subject may be lying horizontally or substantially horizontally sufficient to allow gravity to facilitate clearing of the inner ear canal, or clogged or blocked ET, with formation of negative pressure in the oral cavity. For example, in some embodiments, the subject may be lying down but have their upper body slightly elevated, e.g., lying on a pillow or a lap. In some embodiments, it can be sufficient for the subject to tilt their head sufficiently horizontally to allow gravity to facilitate clearing of the inner ear canal, or clogged or blocked ET, with formation of negative pressure in the oral cavity. In this case, the subject may be standing or seated. In various embodiments, the affected ear is held 180° in relation to the ground, where the position of the ear on a head held upright is defined as 0 degrees in relation to the ground. In some embodiments, the affected ear is held about 135-180° in relation to the ground. As long as the position of the head and the affected ear is held sufficiently horizontally, facing up, to allow gravity to facilitate clearing of the inner ear canal, or clogged or blocked ET, with formation of negative pressure in the oral cavity, the rest of the subject's body can be in any position, including standing, seated or lying down.

In various embodiments, the candy coating the mouthpiece of the safety handle is dissolvable. The subject can suck on one or more of the candy-coated mouthpieces (e.g., in sequence), described herein, for a time sufficient for clearing of the inner ear canal, or clogged or blocked ET, with formation of negative pressure in the oral cavity. In some embodiments, sucking on and consuming the candy of one candy-coated mouthpiece will be sufficient to clear fluid from the ET or inner ear canal. In other instances, successful clearing of fluid from the ET or inner ear canal will require sucking on and consuming two or more compositions. Should the ET or inner ear canal again become clogged or blocked with excess fluid, the subject can suck on and consume the candy of additional candy-coated mouthpieces, as needed, to again clear fluid from the ET or inner ear canal.

Lollipops having the present safety handles further find use in methods of treating pain associated with an ear infection comprising administering to an individual suffering with pain from an ear infection an antibiotic-free salivary-producing candy coating the mouthpiece comprising an internal analgesic. Generally, the subject's posture and duration of performing this embodiment of the method are as described above. The internal analgesic may be any pain reliever or non-steroidal anti-inflammatory drug (NSAID). Pain relievers include without limitation, paracetamol, also known as acetaminophen. NSAIDs include without limitation, acetaminophen, aspirin, choline and magnesium salicylates, choline salicylate, celecoxib, diclofenac, diclofenac potassium, diclofenac sodium, diclofenac sodium with misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, and mixtures thereof.

NSAIDs generally are known agents, and their appropriate dosages are known in the art. Appropriate dosage can depend on various factors, including without limitation, the level of pain, age, weight and general health condition of the subject. In various embodiments, the present methods and compositions deliver a dose of active agent that is equivalent or less than the recommended daily dose provided in standard texts, e.g., Brunton, et al., Goodman and Gilman's The Pharmacological Basis of Therapeutics, Twelfth Edition, 2010, McGraw-Hill Professional; or Physicians' Desk Reference 2014, 68th Edition, PDR Network. Dosages may also be determined by routine experimentation. For example, in determining an appropriate dosage, a lower dose can first be administered and then incrementally increased until an efficacious effect is observed with minimal or no undesirable side effects. Such known or determined dosages of NSAIDs may be used as a guideline for determining the amount of NSAID, or a pharmaceutically acceptable salt thereof, to include in the lollipop, typically taking into account various patient characteristics (e.g., level of pain, age, weight, and overall health) in a manner known to those skilled in the medical arts, as well as the characteristics of the lollipop (e.g., rate of dissolution) and the transmucosal delivery characteristics of the NSAID, or a pharmaceutically acceptable salt thereof.

Where the internal analgesic is acetaminophen, the dosage may be up to 150 mg for children and up to 300 mg for adults. Where the internal analgesic is ibuprofen, the dosage may be up to 100 mg for children and up to 200 mg for adults.

Kits

Further provided are kits comprising one or more safety handle lollipops, as described herein. For example, the kit can comprise one or more safety handles with a candy coated mouthpiece. The candy coated mouthpiece can be in any appropriate shape to fit in a human oral cavity e.g., in the shape of an oral cavity, round, ellipsoid, or octahedral. In various embodiments, the number of safety handle lollipops in the kit is sufficient for administration to or consumption by the subject until the ear infection or blocked inner ear canal is cleared, e.g., 2, 4, 5, 6, 7, 8, 9, 10, 11, 12, 15, 20, or more safety handle lollipops.

The kit may also contain instructions for effective administration of the composition in order to drain fluid and relieve pain of the inner ear. For example, the instructions may advise or illustrate a body posture or position for the subject to assume with the affected ear facing upward to allow the combined actions of gravity and sucking to produce negative pressure within the oral cavity to release excess fluid from the inner ear canal.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device for promoting drainage of fluid from a Eustachian tube of an individual, comprising:
 a handle portion configured to be held by the individual;
 a mouthpiece portion comprising a concave surface and a convex surface; and
 a hard candy composition affixed to the mouthpiece portion and configured to promote a negative pressure within an oral cavity of the individual when used by the individual, the hard candy composition comprising:
  a flat first surface; and
  a convex second surface, opposite the flat first surface, wherein the flat first surface of the mouthpiece portion and the convex second surface of the mouthpiece portion are arranged such that the hard candy composition fits within the oral cavity of the individual with the flat first surface in contact with the individual's tongue, with the convex second surface in contact with a roof of the individual's mouth, and with the handle portion projecting out from the individual's mouth, and
 wherein the hard candy composition is dissolvable and antibiotic-free, and comprises:
  a sweetening agent;
  an extract; and
  a natural flavoring agent.

2. The device of claim 1, wherein the concave surface of the mouthpiece portion comprises:
 one or more grooves; and
 one or more apertures.

3. The device of claim 2, wherein the one or more grooves have a curved or arc shape.

4. The device of claim 1, wherein the concave surface of the mouthpiece portion further comprises: two pairs of concentric grooves arcing around or tracing a curvature of an aperture, and wherein the arc angles of the concentric grooves is from about 20° to about 80°.

5. The device of claim 4, wherein the aperture is beveled up to about 15°, such that an opening of the aperture on the concave surface of the mouthpiece portion is narrower than the opening of the aperture on the convex surface of the mouthpiece portion.

6. The device of claim 1, wherein an angle of the handle portion relative to the mouthpiece portion is in a range of about 5° to about 45°.

7. The device of claim 1, wherein the mouthpiece portion is oval or round.

8. The device of claim 1, wherein the handle portion comprises a length of about 4.25 inches and an average width in a range of about 0.35 to about 0.90 inches.

9. The device of claim 1, wherein proportions of the handle portion are configured to be held by a full human child hand.

10. The device of claim 1, wherein the handle portion comprises a bulbous end opposite the mouthpiece portion.

11. The device of claim 1, wherein the handle portion and the mouthpiece portion are comprised of a material that does not melt at a temperature of about 325° F.

12. The device of claim 1, wherein the handle portion and the mouthpiece portion are made of a polymer material.

13. The device of claim 12, wherein the polymer material is selected from the group consisting of polyamide-imide, polyether ether ketone, polytetrafluoroethylene, polypropylene, polyethylene, low density polyethylene, filled polypropylene, silicone, polysulfone, polyethersulfone, polyphenylsulfone, and mixtures thereof.

14. The device of claim 1, wherein the handle portion is substantially parallel to the flat first surface of the hard candy composition.

15. The device of claim 1, wherein:
 the sweetening agent comprises isomalt and xylitol;
 the extract comprises lemon oil; and
 the natural flavoring agent comprises citric acid.

16. The device of claim 1, wherein the sweetening agent is selected from the group consisting of aspartame, cyclamate, saccharin, *stevia*, sucralose, glucose, arabitol, erythritol, glycerol, hydrogenated starch hydrosylate, lactitol, maltitol, honey, maple syrup, evaporated cane juice, concentrated fruit juice, dextrose, fructose, sucrose, mannitol, sorbitol, isomalt, and xylitol.

17. The device of claim 1, wherein the hard candy composition further comprises: a homeopathic agent.

18. The device of claim 17, wherein the homeopathic agent is selected from the group consisting of *Acontum Napellus, Allium Ceia, Amica, Mullein, Belladona, Bellis Perennis, Calendula, Calcarea Carbonica, Chamomilla, Ferum Phosphorilum, Hamamelis, Hepar Sulphuris, Hypericum Perforatum* (Saint John's Wort), *Kau Bichromicum, Kau Iodatum, Kau Muriaticum, Kau Sulphuricum, Lycopodium, Mercurius Solubilis, Mezereum, Millefolium, Natrum Sulphuricum, Phytolacca Decandra, Phosphorus, Pulsatilla, Sulphur, Symphytum Officinale* and combinations thereof.

* * * * *